(12) United States Patent
Ma et al.

(10) Patent No.: US 9,242,012 B2
(45) Date of Patent: Jan. 26, 2016

(54) METHODS FOR KILLING PSMA-EXPRESSING, TAXANE-RESISTANT CANCER CELLS

(75) Inventors: Dangshe Ma, Millwood, NY (US); William C. Olson, Yorktown Heights, NY (US); Stephen Morris, Croton on Hudson, NY (US); Robert J. Israel, Suffern, NY (US)

(73) Assignee: PSMA Development Company, LLC, Tarrytown, NY (US)

( * ) Notice: Subject to any disclaimer, the term of this patent is extended or adjusted under 35 U.S.C. 154(b) by 791 days.

(21) Appl. No.: 13/030,105

(22) Filed: Feb. 17, 2011

(65) Prior Publication Data

US 2011/0250216 A1      Oct. 13, 2011

Related U.S. Application Data

(63) Continuation-in-part of application No. PCT/US2009/005064, filed on Sep. 8, 2009.

(60) Provisional application No. 61/095,300, filed on Sep. 8, 2008, provisional application No. 61/205,395, filed on Jan. 20, 2009.

(51) Int. Cl.
*A61K 47/48* (2006.01)
*A61K 39/395* (2006.01)

(52) U.S. Cl.
CPC ..... *A61K 47/48415* (2013.01); *A61K 47/48638* (2013.01)

(58) Field of Classification Search
CPC ............ A61K 47/48; A61K 47/48348; A61K 47/48715; A61K 39/00; A61K 38/17
USPC .............. 424/181.1, 178.1; 530/391.9, 391.7, 530/350
See application file for complete search history.

(56) References Cited

U.S. PATENT DOCUMENTS

| | | |
|---|---|---|
| 5,538,866 A | 7/1996 | Israeli et al. |
| 5,773,292 A | 6/1998 | Bander |
| 5,788,963 A | 8/1998 | Murphy et al. |
| 5,804,602 A | 9/1998 | Slusher et al. |
| 5,935,818 A | 8/1999 | Israeli et al. |
| 6,107,090 A | 8/2000 | Bander |
| 6,136,311 A | 10/2000 | Bander |
| 6,150,508 A | 11/2000 | Murphy et al. |
| 6,200,765 B1 | 3/2001 | Murphy et al. |
| 6,383,759 B1 | 5/2002 | Murphy et al. |
| 6,569,432 B1 | 5/2003 | Israeli et al. |
| 6,649,163 B1 | 11/2003 | Bander |
| 6,653,129 B1 | 11/2003 | Bander et al. |
| 6,770,450 B1 | 8/2004 | Bander |
| 6,884,869 B2 | 4/2005 | Senter et al. |
| 6,953,668 B1 | 10/2005 | Israeli et al. |
| 6,962,981 B1 | 11/2005 | Murphy |
| 7,037,647 B1 | 5/2006 | Israeli et al. |
| 7,045,605 B2 | 5/2006 | Bander et al. |
| 7,070,782 B1 | 7/2006 | Israeli et al. |
| 7,091,186 B2 | 8/2006 | Senter et al. |
| 7,098,308 B2 | 8/2006 | Senter et al. |
| 7,105,159 B1 | 9/2006 | Israeli et al. |
| 7,112,412 B1 | 9/2006 | Bander et al. |
| 7,163,680 B2 | 1/2007 | Bander et al. |
| 7,192,586 B2 | 3/2007 | Bander et al. |
| 7,201,900 B2 | 4/2007 | Murphy et al. |
| 7,256,257 B2 | 8/2007 | Doronina et al. |
| 7,381,407 B1 | 6/2008 | Murphy et al. |
| 7,423,116 B2 | 9/2008 | Doronina et al. |
| 7,476,513 B2 | 1/2009 | Murphy et al. |
| 7,498,298 B2 | 3/2009 | Doronina et al. |
| 7,514,078 B2 | 4/2009 | Bander et al. |
| 7,553,816 B2 | 6/2009 | Senter et al. |
| 7,659,241 B2 | 2/2010 | Senter et al. |
| 7,666,414 B2 | 2/2010 | Bander |
| 7,666,425 B1 | 2/2010 | Bander |
| 7,750,116 B1 | 7/2010 | Doronina et al. |
| 7,850,971 B2 | 12/2010 | Maddon et al. |
| 8,114,965 B2 | 2/2012 | Maddon et al. |
| 8,470,330 B2 | 6/2013 | Maddon et al. |
| 2002/0015704 A1 | 2/2002 | Bander |
| 2003/0003101 A1 | 1/2003 | Bander |
| 2003/0031673 A1 | 2/2003 | Bander |
| 2003/0161832 A1 | 8/2003 | Bander |
| 2004/0001846 A1 | 1/2004 | Israeli et al. |
| 2004/0024188 A1 | 2/2004 | Murphy et al. |

(Continued)

FOREIGN PATENT DOCUMENTS

| | | |
|---|---|---|
| AU | 717937 B2 | 7/2000 |
| EP | 1 512 755 A2 | 3/2005 |

(Continued)

OTHER PUBLICATIONS

Moreno et al. (Urology. 2001, 58: 386-92).*
Wang et al. (Mol Cancer Ther., 2011, 10: 1728-1739).*
[No Author Listed] "Medarex Announces Filing of Investigational New Drug Application for MDX-070; Fully Human Anti-PSMA Antibody Candidate for Prostate Cancer." Press Release. PR Newswire. Monday, Jan. 6, 2003, 4:36 P.M. 2 pages.
[No Author Listed] "Medarex: Pipeline." Available at http://www.medarex.com/Development/Pipeline.html. Last accessed Mar. 17, 2009.
[No Author Listed] "Promising Findings" from Novel Antibody-Chemotherapeutic MLN2704 Prostate Cancer Clinical Trial . . . PSA Rising. Feb. 22, 2005. Available at http://www.psa-rising.com/med/chemo/millennium05.html. Last accessed Jan. 19, 2010. 8 pages.

(Continued)

*Primary Examiner* — Yan Xiao
(74) *Attorney, Agent, or Firm* — Wolf, Greenfield & Sacks, P.C.

(57) ABSTRACT

Methods of killing prostate-specific membrane antigen (PSMA)-expressing, taxane-resistant cancer cells are provided. In particular, PSMA-expressing, taxane-resistant cancer cells are contacted with an antibody-drug conjugate (ADC) that comprises an antibody or antigen-binding fragment thereof that specifically binds to PSMA conjugated to monomethylauristatin norephedrine or monomethylauristatin phenylalanine.

32 Claims, 16 Drawing Sheets

(56) References Cited

U.S. PATENT DOCUMENTS

| | | | |
|---|---|---|---|
| 2004/0033229 A1 | 2/2004 | Maddon et al. |
| 2004/0105865 A1 | 6/2004 | Bander |
| 2004/0120958 A1 | 6/2004 | Bander et al. |
| 2004/0136998 A1 | 7/2004 | Bander et al. |
| 2004/0161776 A1 | 8/2004 | Maddon et al. |
| 2004/0213791 A1 | 10/2004 | Bander |
| 2004/0253246 A1 | 12/2004 | Israeli et al. |
| 2005/0009751 A1 | 1/2005 | Senter et al. |
| 2005/0215472 A1 | 9/2005 | Schulke et al. |
| 2005/0238649 A1 | 10/2005 | Doronina et al. |
| 2006/0074008 A1 | 4/2006 | Senter et al. |
| 2006/0088539 A1 | 4/2006 | Bander |
| 2006/0177450 A1 | 8/2006 | Israeli et al. |
| 2006/0234271 A1 | 10/2006 | Su et al. |
| 2006/0275212 A1 | 12/2006 | Bander et al. |
| 2007/0128671 A1 | 6/2007 | Murphy et al. |
| 2007/0148662 A1 | 6/2007 | Israeli et al. |
| 2007/0160617 A1 | 7/2007 | Ma et al. |
| 2008/0226657 A1 | 9/2008 | Doronina et al. |
| 2008/0248051 A1 | 10/2008 | Doronina et al. |
| 2008/0248053 A1 | 10/2008 | Doronina et al. |
| 2008/0286284 A1 | 11/2008 | Maddon et al. |
| 2008/0300192 A1 | 12/2008 | Doronina et al. |
| 2009/0018086 A1 | 1/2009 | Doronina et al. |
| 2009/0047296 A1 | 2/2009 | Doronina et al. |
| 2009/0111756 A1 | 4/2009 | Doronina et al. |
| 2009/0238755 A1 | 9/2009 | Bander |
| 2009/0311225 A1 | 12/2009 | Koduri |
| 2010/0303715 A1 | 12/2010 | Israeli et al. |
| 2011/0165081 A1 | 7/2011 | Schulke et al. |
| 2011/0250216 A1 | 10/2011 | Ma et al. |
| 2014/0286859 A1 | 9/2014 | Maddon et al. |

FOREIGN PATENT DOCUMENTS

| | | | | |
|---|---|---|---|---|
| EP | 1 553 414 A1 | 7/2005 | | |
| EP | 1 710 256 A1 | 10/2006 | | |
| WO | WO 94/09820 A1 | 5/1994 | | |
| WO | WO 96/26272 A1 | 8/1996 | | |
| WO | WO 96/39185 A1 | 12/1996 | | |
| WO | WO 97/04802 A1 | 2/1997 | | |
| WO | WO 97/35616 A1 | 10/1997 | | |
| WO | WO 98/02463 A1 | 1/1998 | | |
| WO | WO 98/03873 A1 | 1/1998 | | |
| WO | WO 99/47554 A1 | 9/1999 | | |
| WO | WO 99/56779 A1 | 11/1999 | | |
| WO | WO 99/61097 A1 | 12/1999 | | |
| WO | WO 00/14257 A1 | 3/2000 | | |
| WO | WO 01/09192 A1 | 7/2000 | | |
| WO | WO 00/61605 A1 | 10/2000 | | |
| WO | WO 00/62063 A1 | 10/2000 | | |
| WO | WO 01/09192 A1 | 2/2001 | | |
| WO | WO 01/19956 A2 | 3/2001 | | |
| WO | WO 01/85798 A2 | 11/2001 | | |
| WO | WO 01/87325 A1 | 11/2001 | | |
| WO | WO 02/43661 A2 | 6/2002 | | |
| WO | WO 02/088172 A2 | 11/2002 | | |
| WO | WO 02/096460 A1 | 12/2002 | | |
| WO | WO 02/098897 A2 | 12/2002 | | |
| WO | WO 03/024388 A2 | 3/2003 | | |
| WO | WO 03/026577 A2 | 4/2003 | | |
| WO | WO 03/040169 A2 | 5/2003 | | |
| WO | WO 03/057921 A1 | 7/2003 | | |
| WO | WO 03/064606 A2 | 8/2003 | | |
| WO | WO 03/064612 A2 | 8/2003 | | |
| WO | WO 2004/010957 A2 | 2/2004 | | |
| WO | WO 2004/063701 A2 | 7/2004 | | |
| WO | WO 2004/072262 A2 | 8/2004 | | |
| WO | WO 2004/073656 A2 | 9/2004 | | |
| WO | WO 2004/098535 A2 | 11/2004 | | |
| WO | WO 2005/001038 A2 | 1/2005 | | |
| WO | WO 2005/070456 A2 | 8/2005 | | |
| WO | WO 2005/081711 A2 | 9/2005 | | |
| WO | WO 2005/084390 A2 | 9/2005 | | |
| WO | WO 2005/094882 A1 | 10/2005 | | |
| WO | WO 2006/002438 A2 | 1/2006 | | |
| WO | WO 2006/028999 A2 | 3/2006 | | |
| WO | WO 2006/039418 A2 | 4/2006 | | |
| WO | WO 2006/076525 A2 | 7/2006 | | |
| WO | WO 2006/089230 A2 | 8/2006 | | |
| WO | WO 2006/089231 A2 | 8/2006 | | |
| WO | WO 2006/110745 A2 | 10/2006 | | |
| WO | WO 2006/132670 A2 | 12/2006 | | |
| WO | WO 2007/002222 | * | 1/2007 | ............ A61K 47/48 |
| WO | WO 2007/008603 A1 | 1/2007 | | |
| WO | WO 2007/008848 A2 | 1/2007 | | |
| WO | WO 2007/011968 A2 | 1/2007 | | |
| WO | WO 2007/038658 A2 | 4/2007 | | |
| WO | WO 2007/103288 A2 | 9/2007 | | |

OTHER PUBLICATIONS

[No Author Listed] Latest Cancer Findings Presented at ASCO Meeting by Physician-scientists. Medical News Today. http://www.medicalnewstoday.com/articles/109424.php. Jun. 2, 2008. 3 pages. Last accessed online Oct. 29, 2008.

[No Author Listed] New York-Presbyterian/Weill Cornell Physician-Scientists Present Latest Cancer Findings at American Society of Clinical Oncology (ASCO) Meeting http://www.nyp.org/news/hospital/nypwc-presents-asco.html. May 30, 2008. 3 pages. Last accessed Oct. 29, 2008.

[No Author Listed] NYP/ Weill Cornell physician-scientists present latest cancer findings at ASCO meeting. Bio-Medicine. http://biomedicine.org/medicine-news-1/NYP-Weill-Cornell-physician-scientists-p . . . May 31, 2008. 4 pages. Last accessed Oct. 29, 2008.

[No Author Listed] Physician-Scientists Present Latest Cancer Findings at ASCO Meeting. Newswise. http://www.newswise.com/articles/view/541288. Released: May 30, 2008. 08:00 ET. 3 pages. Last accessed Oct. 28, 2008.

[No Author Listed] Progenics and Cytogen Report Positive Preclinical Results for Experimental Prostate Cancer Drug—In laboratory studies, human monoclonal antibody killed prost. Progenics Pharmaceuticals, Inc. Press Release. Washington, D.C. Sep. 23, 2002. Available at http://www.lifesciencesworld.com/life-science-news/view/535?page=1495. Last accessed Jul. 26, 2011. 1 page.

[No Author Listed] Progenics Initiates Phase 1 Clinical Study of Targeted Therapy for Prostate Cancer. Progenics Pharmaceuticals Press Release. Sep. 8, 2008. 3 pages.

[No Author Listed] Radiolabeled J591 Antibody Delivers Lethal Hit to Advanced Prostate Cancers in Phase 1 Trial. Cancer Biol & Ther. 2004;3(8):699-700.

[No Author Listed] Seattle Genetics and PSMA Development Company Announce Antibody-Drug Conjugate Collaboration. Business Wire. Jun. 20, 2005. Available at http://www.thefreelibrary.com/Seattle+Genetics+and+PSMA+Development+Company+Announce+Antibody-Drug . . . -a0133363839. Last accessed Jan. 24, 2011. 4 pages.

[No Author Listed], FDA: Pfizer voluntarily withdraws cancer treatment Mylotarg from U.S. market. FDA News Release. Jun. 21, 2010. Retrieved from http://www.fda.gov/NewsEvents/Newsroom/PressAnnouncements/ucm216448.htm on Aug. 10, 2012. Last updated Jun. 22, 2010.

[No author listed], Progenics Pharmaceuticals initiates Phase 2 clinical trial of PSMA ADC in prostate cancer patients. Press Release Sep. 28, 2012. 2 pages.

Abdel-Nabi et al., Monoclonal antibodies and radioimmunoconjugates in the diagnosis and treatment of prostate cancer. Semin Urol. Feb. 1992;10(1):45-54.

Ablin "Immunotherapy for prostatic cancer. Previous and Prospective Considerations[1]", *Oncology* (1975) vol. 31, 177-202.

Allen, Ligand-targeted therapeutics in anticancer therapy. Nat Rev Cancer. Oct. 2002;2(10):750-63.

Arlen et al., Therapeutic vaccines for prostate cancer: a review of clinical data. Curr Opin Investig Drugs. Jun. 2005;6(6):592-6.

Axelrod et al., "Preclinical results and human immunohistochemical studies with $^{90}$Y-CYT-356: A new prosate cancer therapeutic agent". AUA 87th Annual Meeting. 1992:Abstract #596.

(56) References Cited

OTHER PUBLICATIONS

Bander et al., Phase I radioimmunotherapy (RIT) trial of humanized monoclonal (mAb) antibody J591 to the extracellular domain of prostate specific membrane antigen (PSMAext) radiolabeled with 171eutetium (177Lu) in advanced prostate cancer (Pca). 2003 ASCO Annual Meeting. Proc Am Soc Clin Oncol. 2003;22. Abstract 1612.

Bander et al., Phase I radioimmunotherapy (RIT) trials of humanized monoclonal antibody (mAb) J591 to the extracellular domain of prostate specific membrane antigen (PSMA ext) radiolabeled with 90Y or 177Lu in advanced prostate cancer (Pca). 2002 ASCO Annual Meeting. Biologic and Targeted Therapies; Antibodies. Abstract No. 18.

Bander et al., Phase II trial of 177Lutetium radiolabeled anti-prostate-specific membrane antigen (PSMA) monoclonal antibody J591 (177Lu-J591) in patients (pts) with metastatic androgen-independent prostate cancer (AIPC). J Clin Oncol. 2007 ASCO Annual Meeting Proceedings Part 1. 2007;25(18S). Abstract 15523.

Bander et al., Targeted systemic therapy of prostate cancer with a monoclonal antibody to prostate-specific membrane antigen. Semin Oncol. Oct. 2003;30(5):667-77.

Bander, Current status of monoclonal antibodies for imaging and therapy of prostate cancer Semin Oncol. Oct. 1994;21(5):607-12.

Bander, Immunotherapy of Prostate Cancer. State of the Science. Genitourinary. Dec. 13-14, 2002. 9 pages.

Basler et al., Advances in prostate cancer immunotherapies. Drugs Aging. 2007;24(3):197-221.

Bhaskar et al., E-selectin up-regulation allows for targeted drug delivery in prostate cancer. Cancer Res. Oct. 1, 2003;63(19):6387-94.

Bocchia et al., Antitumor vaccination: where we stand. Haematologica. Nov. 2000;85(11):1172-206.

Bodey et al., Failure of cancer vaccines: the significant limitations of this approach to immunotherapy. Anticancer Res. Jul.-Aug. 2000;20(4):2665-76.

Carter, Improving the efficacy of antibody-based cancer therapies. Nat Rev Cancer. Nov. 2001;1(2):118-29.

Chang et al., Monoclonal antibodies: will they become an integral part of the evaluation and treatment of prostate cancer—focus on prostate-specific membrane antigen? Review Article. Curr Opin Urology. 1999;9(5):391-95.

Chen et al., Antibody-cytotoxic agent conjugates for cancer therapy. Expert Opin Drug Deliv. Sep. 2005;2(5):873-90.

Damle, Tumour-targeted chemotherapy with immunoconjugates of calicheamicin. Expert Opin Biol Ther. Sep. 2004;4(9):1445-52.

Darshan et al., Taxanes inhibit AR nuclear accumulation and signaling in cells and metastatic prostate cancer patients. Novel Drug Targets, Agents, and Mechanisms: Poster Presentations—Proffered Abstracts. 99th AACR Annual Meeting. Apr. 12-16, 2008. Abstract 2808.

Donovan et al., Antibody and vaccine therapies targeting prostate specific membrane antigen (PSMA). Proceedings of the Annual Meeting of the AACR. New York, NY. Mar. 24, 2001;42:818. Abstract 4389.

Donovan et al., Clinical development of immunotherapies targeting prostate specific membrane antigen. 38th Annual Meeting American Society of Clinical Oncology. Alexandria, VA. May 18-21, 2002. Presentation. PSMA Development Company, LLC. Tarrytown, NY (joint venture between Progenics Pharmaceuticals, Inc. and Cytogen Corporation) and The Cleveland Clinic, Cleveland, OH. Proceedings of ASCO. 2002;21:25b. Abstract #1909.

Donovan et al., Development of PSMA-based immunotherapies for prostate cancer. AACR Meeting. San Francisco, CA. Apr. 6-10, 2002. PSMA Development Company, LLC. Tarrytown, NY (joint venture between Progenics Pharmaceuticals, Inc. and Cytogen Corporation) and The Cleveland Clinic, Cleveland, OH. Abstract 456.

Doronina et al., Development of potent monoclonal antibody auristatin conjugates for cancer therapy. Nat Biotechnol. Jul. 2003;21(7):778-84. Epub Jun. 1, 2003. Erratum.

Doronina et al., Enhanced activity of monomethylauristatin F through monoclonal antibody delivery: effects of linker technology on efficacy and toxicity. Bioconjug Chem. Jan.-Feb. 2006;17(1):114-24.

Doronina et al., Immunoconjugates comprised of drugs with impaired cellular permeability: A new approach to targeted therapy. Abstracts of papers. ACS National Meeting. Aug. 2004;228:U908. Cited as AACR meeting abstracts online, Pro Amer Assoc Cancer Res v45 Experimental and Molecular Therapeutics 6: Novel Delivery Strategies, Abstract #623.

Doronina et al., Novel linkers for monoclonal antibody-mediated delivery of anticancer agents AACR. Anaheim, CA. Apr. 16-20, 2005. Abstract No. 1421.

Doronina et al., Novel peptide linkers for highly potent antibody-auristatin conjugate. Bioconjug Chem. Oct. 2008;19(10):1960-3. Epub Sep. 20, 2008.

Francisco et al., cAC10-vcMMAE, an anti-CD30-monomethyl auristatin E conjugate with potent and selective antitumor activity. Blood. Aug. 15, 2003;102(4):1458-65. Epub Apr. 24, 2003.

Galsky et al., Phase I trial of the prostate-specific membrane antigen-directed immunoconjugate MLN2704 in patients with progressive metastatic castration-resistant prostate cancer. J Clin Oncol. May 1, 2008;26(13):2147-54. Epub Mar. 24, 2008.

Ghose et al., The design of cytotoxic-agent-antibody conjugates. CRC Critical Reviews in Therapeutic Drug Carrier Systems. 2000;3:263-359.

Gong et al., Prostate-specific membrane antigen (PSMA)-specific monoclonal antibodies in the treatment of prostate and other cancers. Cancer Metastasis Rev. 1999;18(4):483-90

Graves et al., Molecular modeling and preclinical evaluation of the humanized NR-LU-13 antibody. Clin Cancer Res. Apr. 1999;5(4):899-908.

Harada et al., Target molecules in specific immunotherapy against prostate cancer. Int J Clin Oncol. Aug. 2003;8(4):193-9.

Holmes, PSMA specific antibodies and their diagnostic and therapeutic use. Expert Opin Investig Drugs. Mar. 2001;10(3):511-9.

Huang et al., Anti-tumor effects and lack of side effects in mice of an immunotoxin directed against human and mouse prostate-specific membrane antigen. Prostate. Sep. 15, 2004;61(1):1-11.

Huang et al., Inhibition of growth and metastasis of orthotopic human prostate cancer in athymic mice by combination therapy with pegylated interferon-alpha-2b and docetaxel. Cancer Res. Oct. 15, 2002;62(20):5720-6.

Hynecek et al., $^{177}$Lu-J591 monoclonal antibody (Lu-J591) therapy in metastatic castrate-resistant prostate cancer (metCRPC): Correlation of antibody-tumor targeting and treatment response Oncology-Basic Science: Therapy, Metrics & Intervention Imaging for Assessment of Response Therapy Planning. J Nucl Med. 2008;49(Supplement 1):144P. 2 pages.

Jacobs et al., Clinical use of tumor markers in oncology. Curr Probl Cancer. Nov.-Dec. 1991;15(6):299-350.

Jain et al., Optimization of radioimmunotherapy of solid tumors: biological impediments and their modulation. Clin Cancer Res. Mar. 1, 2007;13(5):1374-82. Epub Feb. 19, 2007.

Jaracz et al., Recent advances in tumor-targeting anticancer drug conjugates. Bioorg Med Chem. Sep. 1, 2005;13(17):5043-54.

Jayaprakash et al., Design and synthesis of a PSMA inhibitor-doxorubicin conjugate for targeted prostate cancer therapy. ChemMedChem. Mar. 2006;1(3):299-302.

Lambert, Drug-conjugated monoclonal antibodies for the treatment of cancer. Curr Opin Pharmacol. Oct. 2005;5(5):543-9.

Lapidus et al., Prostate-specific membrane antigen (PSMA) enzyme activity is elevated in prostate cancer cells. Prostate. Dec. 1, 2000;45(4):350-4.

Law et al., Efficient elimination of B-lineage lymphomas by anti-CD20-auristatin conjugates. Clin Cancer Res. Dec. 1, 2004;10(23):7842-51.

Li et al., Trastuzumab-auristatin immunoconjugates inhibit growth and induce apoptosis of human breast cancer cells in vitro. Department of Translational Oncology. Genentech, Inc. South San Francisco, CA. Department of Biochemistry, Seattle Genetics, Inc. Bothell, WA. Poster#6184, 2005.

(56) References Cited

OTHER PUBLICATIONS

Lin et al., A functional role of prostate-specific membrane antigen in prostate cancer metastasis Tumor Biology 30: Proteases: Protease Inhibitors and Cancer. Proc Amer Assoc Cancer Res. 2006;47. Abstract 4373.
Ma et al., Fully human anti-PSMA antibodies for prostate cancer therapy. Proc AACR. Jul. 2003;44(2):1295. Abstract #6471.
Ma et al., Fully human monoclonal antibodies to PSMA selectively target cytotoxins, radiotoxins and host immunity to prostate cancer. J Clin Oncol. ASCO Annual Meeting Proceedings. 2004;22:14S. Abstract No. 2546. Abstract Only.
Ma et al., Potent antitumor activity of an auristatin-conjugated, fully human monoclonal antibody to prostate-specific membrane antigen. Clin Cancer Res. Apr. 15, 2006;12(8):2591-6.
Ma et al., PSMA targeted toxin and radio-labelled antibody therapies for prostate cancer. J Urology. 2003;169:211. Poster 817.
Mays et al., MDX-070, a human anti-plasma antibody, administered as either a single dose or as multiple doses to patients with hormone-refractory prostate cancer. ASCO Annual Meeting, 2006. Abstract #14549.
McDevitt et al., An alpha-particle emitting antibody ([213Bi]J591) for radioimmunotherapy of prostate cancer. Cancer Res. Nov. 1, 2000;60(21):6095-100.
Mega et al., Prostate specific membrane antigen antibody drug conjugate (PSMA ADC): A Phase I trial in subjects with castration-resistant metastatic prostate cancer (CRMPC) previously treated with taxane. Poster presented Feb. 2012 Genitourinary Cancers Symposium.
Milowsky et al., Phase I trial of yttrium-90-labeled anti-prostate-specific membrane antigen monoclonal antibody J591 for androgen-independent prostate cancer. J Clin Oncol. Jul. 1, 2004;22(13):2522-31. Epub Jun. 1, 2004.
Milowsky et al., Phase I trial results of yttrium-90 ($^{90}$Y)-labeled anti-prostate specific membrane antigen (PSMA) monoclonal antibody (mAb) J591 in the treatment of patients with advanced prostate cancer (PC). 2003 ASCO Annual Meeting. Proc Am Soc Clin Oncol. 2003;22. Abstract 1583.
Monson, Recent progress in the use of monoclonal antibodies for imaging and therapy. Curr Opin Gen Surg. 1993:334-9.
Morris et al., Phase I evaluation of J591 as a vascular targeting agent in progressive solid tumors. Clin Cancer Res. May 1, 2007;13(9):2707-13.
Morris et al., Pilot trial of unlabeled and indium-111-labeled anti-prostate-specific membrane antigen antibody J591 for castrate metastatic prostate cancer. Clin Cancer Res. Oct. 15, 2005;11(20):7454-61.
Muprhy et al., Comparison of prostate specific membrane antigen, and prostate specific antigen levels in prostatic cancer patients. Anticancer Res. Jul.-Aug. 1995;15(4):1473-9.
Nanus et al., Clinical use of monoclonal antibody HuJ591 therapy: targeting prostate specific membrane antigen. J Urol. Dec. 2003;170(6 Pt 2):S84-8; discussion S88-9. Abstract only.
Olson et al., Clinical trials of cancer therapies targeting prostate-specific membrane antigen. Rev Recent Clin Trials. Sep. 2007;2(3):182-90.
Partin et al., The clinical usefulness of prostate specific antigen: update 1994. Urol. Nov. 1994;152(5 Pt 1):1358-68. Review.
Pastuskovas et al., Tissue distribution, metabolism, and excretion of the antibody-drug conjugate herceptin-monomethyl auristatin E in rats. Department of Pharmacokinetic and Pharmacodynamic Sciences, Genentech, Inc. South San Francisco, CA. Seattle Genetics, Bothell, WA. Poster #5063, 2005.
Petrylak et al., Prostate-specific membrane antigen antibody drug conjugate (PSMA ADC): a phase I trial in taxane-refractory prostate cancer. Poster presented Feb. 17, 2011 Genitourinary Cancers Symposium General Poster Session B. Abstract published ASCO Meeting Abstracts Mar. 29, 2011:158. J Clin Oncol 29: Mar. 2011 (suppl 7; abstr 158).
Petrylak, BRD E18: A phase II trial of prostate-specific membrane antigen antibody drug conjugate (PSMA ADC) in taxane-refractory metastatic castration-resistant prostate cancer (mCRPC). 2014 Genitourinary Cancers Symposium (abstract 83).
Riechmann et al., Reshaping human antibodies for therapy. Nature. Mar. 4, 1988;332(6162):323-7.
Saijo, What are the reasons for negative phase III trials of molecular-target-based drugs? Cancer Sci. Oct. 2004;95(10):772-6.
Sanderson et al., In vivo drug-linker stability of an anti-CD30 dipeptide-linked auristatin immunoconjugate. Clin Cancer Res. Jan. 15, 2005;11(2 Pt 1):843-52.
Schuelke et al., Human prostate specific membrane antigen (PSMA) is expressed as a non-covalent dimer and provides an attractive target for cancer immunotherapy. Eur J Cancer. Nov. 2002;38:S153. Poster 510.
Schulke et al., The homodimer of prostate-specific membrane antigen is a functional target for cancer therapy. Proc Natl Acad Sci USA. Oct. 28, 2003;100(22):12590-95.
Senter, Potent antibody drug conjugates for cancer therapy. Curr Opin Chem Biol. Jun. 2009;13(3):235-44. Epub May 4, 2009.
Sharkey et al., Targeted therapy of cancer: new prospects for antibodies and immunoconjugates. CA Cancer J Clin. Jul.-Aug. 2006;56(4):226-43.
Small, Monoclonal antibody therapy for prostate cancer: finally a reality? J Clin Oncol. Jul. 1, 2004;22(13):2515-6. Epub Jun. 1, 2004.
Smith-Jones et al., In vitro characterization of radiolabeled monoclonal antibodies specific for the extracellular domain of prostate-specific membrane antigen. Cancer Res. Sep. 15, 2000;60(18):5237-43.
Smith-Jones et al., Radiolabeled monoclonal antibodies specific to the extracellular domain of prostate-specific membrane antigen: preclinical studies in nude mice bearing LNCaP human prostate tumor. J Nucl Med. Apr. 2003;44(4):610-7.
Su et al., Alternatively spliced variants of prostate-specific membrane antigen RNA: ratio of expression as a potential measurement of progression. Cancer Res. Apr. 1, 1995;55(7):1441-3.
Sweat et al., Prostate-specific membrane antigen expression is greatest in prostate adenocarcinoma and lymph node metastatses. Urology. Oct. 1998;52(4):637-40.
Tagawa et al., Phase II trial of 177Lutetium radio-labeled anti-prostate-specific membrane antigen (PSMA) monoclonal antibody J591 (177Lu-J591) in patients (pts) with metastatic castrate-resistant prostate cancer (metCRPC). 2008 ASCO Annual Meeting. J Clin Oncol. 2008;26(May 20 Suppl.). Abstract 5140.
Trail et al., Monoclonal antibody drug immunoconjugates for targeted treatment of cancer. Cancer Immunol Immunother. May 2003;52(5):328-37. Epub Jan. 16, 2003.
Tralongo et al., Vinorelbine and prednisone in older cancer patients with hormone-refractory metastatic prostate cancer. A phase II study. Tumori. Jan.-Feb. 2003;89(1):26-30. Abstract only.
Vitetta et al., Immunotoxins. Annu Rev Immunol. 1985;3:197-212.
Vriesendorp et al., Radiolabeled immunoglobulin therapy: old barriers and new opportunities. Expert Rev Anticancer Ther. Oct. 2001;1(3):461-78.
Wang et al. In vitro and in vivo responses of advanced prostate tumors to PSMA ADC, an auristatin-conjugated antibody to prostate-specific membrane antigen. Mol Cancer Ther. Sep. 2011;10(9):1728-39.
Webb et al., Rationale for immunotoxin therapy of metastatic prostate carcinoma formatted as a multi-stage delivery system. J Urol. Aug. 1989;142(2 Pt 1):425-32.
Weill Medical College of Cornell University: "177 Lu Radiolabeled Monoclonal Antibody HuJ591 (177 Lu-J591) and Ketoconazole in Patients with Prostate Cancer". ClinicalTrials.gov, Mar. 10, 2008, XP055139382.
Weill Medical College of Cornell University: "Docetaxel/Prednisone Plus Fractionated177 Lu-J591 Antibody for metastatic, castrate-resistant prostate cancer" ClinicalTrials.gov, Jun. 5, 2009, pp. 1-6, XP055139381.
Weiner et al., New approaches to antibody therapy. Oncogene. Dec. 11, 2000;19(53):6144-51.

(56) References Cited

OTHER PUBLICATIONS

Williams et al., Discontinued drugs in 2006: oncology drugs. Expert Opin Investig Drugs. Mar. 2008;17(3):269-83.
Wolf, Herstellung und Charakterisierung rekombinanter Immunotoxine aus anti-PSMA single-chain-Antikörperfragmenten zur Therapie des Prostatakarzinoms. Ph.D. Thesis. Dec. 2005. 33 pages. 2 page German abstract. 31 page English translation.
Wood et al., Past and future of the mitotic spindle as an oncology target. Curr Opin Pharmacol. Aug. 2001;1(4):370-7.
US 6,290,956, 09/2001, Bander (withdrawn)

* cited by examiner

| CELL LINES | MFI[1] | IC$_{50}$ (nM) | POTENCY (nM)[2] | SELECTIVITY[3] |
|---|---|---|---|---|
| PSMA-POSITIVE | | | | |
| C4-2 (PROSTATE) | 88 ± 50 (n = 2) | 0.10 ± 0.01 (n = 3) | 0.26 ± 0.20 | 1,131 |
| LNCaP (PROSTATE) | 140 (n = 1) | 0.20 ± 0.07 (n = 3) | | |
| 3T3-PSMA (FIBROBLAST) | 314 ± 53 (n = 2) | 0.49 ± 0.20 (n = 3) | | |
| PSMA-NEGATIVE | | | | |
| RAMOS (B LYMPHOCYTE) | 10.6 ± 10.4 (n = 2) | 46 ± 13 (n = 2) | 299 ± 355 | 1,131 |
| IMR-90 (LUNG FIBROBLAST) | 1.9 ± 0.6 (n = 2) | 62 ± 55 (n = 3) | | |
| PC-3 (PROSTATE) | 6.6 ± 6.1 (n = 2) | 74 ± 10 (n = 3) | | |
| Hep 3B (LIVER) | 5.5 (n = 1) | 113 ± 87 (n = 3) | | |
| HeLa (CERVIX) | 3.3 ± 1.2 (n = 2) | 173 ± 61 (n = 3) | | |
| MCF7 (BREAST) | 2.2 (n = 1) | 192 ± 87 (n = 3) | | |
| 3T3 (FIBROBLAST) | 10.2 ± 8.7 (n = 2) | 822 ± 151 (n = 3) | | |
| Caco-2 (COLON) | 8.4 ± 2.5 (n = 2) | 912 (n = 1) | | |

[1] MEAN FLUORESCENCE INTENSITY OF PSMA STAINING BY FLOW CYTOMETRY

[2] AVERAGE OF IC$_{50}$s (CONCENTRATION REQUIRED FOR 50% CELL KILLING) OF ALL PSMA-POSITIVE OR PSMA-NEGATIVE CELL LINES

[3] SELECTIVITY EQUALS THE RATIO OF POTENCIES DETERMINED FOR THE PSMA-NEGATIVE AND PSMA-POSITIVE CELL LINES

```
SEQUENCE LISTING

<160> NUMBER OF SEQ ID NOS: 33

<210> SEQ ID NO 1
<211> LENGTH: 750
<212> TYPE: PRT
<213> ORGANISM: Homo sapiens

<400> SEQUENCE: 1

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140
```

```
Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
            165                 170                 175

Val Asn Tyr Ala Arg Thr Glu Asp Phe Phe Lys Leu Glu Arg Asp Met
        180                 185                 190

Lys Ile Asn Cys Ser Gly Lys Ile Val Ile Ala Arg Tyr Gly Lys Val
    195                 200                 205

Phe Arg Gly Asn Lys Val Lys Asn Ala Gln Leu Ala Gly Ala Lys Gly
210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
        435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
        515                 520                 525

Gly Ile Ala Ser Gly Arg Ala Arg Tyr Thr Lys Asn Trp Glu Thr Asn
530                 535                 540

Lys Phe Ser Gly Tyr Pro Leu Tyr His Ser Val Tyr Glu Thr Tyr Glu
545                 550                 555                 560
```

| | | | | | | | | | | | |
|---|---|---|---|---|---|---|---|---|---|---|---|
|Leu|Val|Glu|Lys|Phe|Tyr|Asp|Pro|Met|Phe|Lys|Tyr|His|Leu|Thr|Val|
| | | | |565| | | |570| | | |575|

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
            610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
            645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
            725                 730                 735

Phe Thr Val Gln Ala Ala Ala Glu Thr Leu Ser Glu Val Ala
            740                 745                 750

<210> SEQ ID NO 2
<211> LENGTH: 7570
<212> TYPE: DNA
<213> ORGANISM: Artificial Sequence
<220> FEATURE:
<223> OTHER INFORMATION: Plasmid

<400> SEQUENCE: 2

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta caactccgcc ccattgacgc aaatgggcg     780
gtaggcgtgt acggtgggag gtctatataa gcagagctct ctggctaact agagaaccca    840
ctgcttactg gcttatcgaa attaatacga ctcactatag ggagacccaa gctggctaga    900
ggtaccaagc ttgatctca ccatggagtt gggactgcgc tggggcttcc tcgttgctct    960
tttaagaggt gtccagtgtc aggtgcaatt ggtggagtct gggggaggcg tggtccagcc   1020
```

```
tgggaggtcc ctgagactct cctgtgcagc gtctggattc gccttcagta gatatggcat    1080
gcactgggtc cgccaggctc caggcaaggg gctggagtgg gtggcagtta tatggtatga    1140
tggaagtaat aaatactatg cagactccgt gaagggccga ttcaccatct ccagagacaa    1200
ttccaagaac acgcagtatc tgcaaatgaa cagcctgaga gccgaggaca cggctgtgta    1260
ttactgtgcg agaggcggtg acttcctcta ctactactat tacggtatgg acgtctgggg    1320
ccaagggacc acggtcaccg tctcctcagc ctccaccaag ggcccatcgg tcttccccct    1380
ggcaccctct agcaagagca cctctggggg cacagcggcc ctgggctgcc tggtcaagga    1440
ctacttcccc gaaccggtga cggtgtcgtg gaactcaggc gccctgacca gcggcgtgca    1500
caccttcccg gctgtcctac agtcctcagg actctactcc ctcagcagcg tggtgaccgt    1560
gccctccagc agcttgggca cccagaccta catctgcaac gtgaatcaca agcccagcaa    1620
caccaaggtg gacaagagag ttggtgagag gccagcacag gagggagggt gtctgctgg     1680
aagccaggct cagcgctcct gcctggacgc atcccggcta tgcagtccca gtccagggca    1740
gcaaggcagg ccccgtctgc ctcttcaccc ggaggcctct gcccgcccca ctcatgctca    1800
gggagagggt cttctggctt ttccccagg ctctgggcag gcacaggcta ggtgccccta    1860
acccaggccc tgcacacaaa ggggcaggtg ctgggctcag acctgccaag agccatatcc    1920
gggaggaccc tgcccctgac ctaagcccac cccaaaggcc aaactctcca ctccctcagc    1980
tcggacacct tctctcctcc cagattccag taactcccaa tcttctctct gcagagccca    2040
aatcttgtga caaaactcac acatgcccac cgtgcccagg taagccagcc caggcctcgc    2100
cctccagctc aaggcgggac aggtgcccta gagtagcctg catccaggga caggccccag    2160
ccgggtgctg acacgtccac ctccatctct cctcagcac ctgaactcct gggggaccg    2220
tcagtcttcc tcttccccc aaacccaag acaccctca tgatctcccg gacccctgag    2280
gtcacatgcg tggtggtgga cgtgagccac gaagaccctg aggtcaagtt caactggtac    2340
gtggacggcg tggaggtgca taatgccaag acaaagccgc gggaggagca gtacaacagc    2400
acgtaccgtg tggtcagcgt cctcaccgtc ctgcaccagg actggctgaa tggcaaggag    2460
tacaagtgca aggtctccaa caaagccctc ccagccccca tcgagaaaac catctccaaa    2520
gccaaaggtg ggacccgtgg ggtgcgaggg ccacatggac agaggccggc tcggcccacc    2580
ctctgccctg agagtgaccg ctgtaccaac ctctgtccct acagggcagc cccgagaacc    2640
acaggtgtac accctgcccc catcccggga ggagatgacc aagaaccagg tcagcctgac    2700
ctgcctggtc aaaggcttct atcccagcga catcgccgtg gagtgggaga gcaatgggca    2760
gccggagaac aactacaaga ccacgcctcc cgtgctggac tccgacggct ccttcttcct    2820
ctatagcaag ctcaccgtgg acaagagcag gtggcagcag gggaacgtct tctcatgctc    2880
cgtgatgcat gaggctctgc acaaccacta cacgcagaag agcctctccc tgtctccggg    2940
taaatgagaa ttcctcgagt ctagagggcc gtttaaaccc gctgatcag cctcgactgt    3000
gccttctagt tgccagccat ctgttgtttg ccctcccc gtgccttcct tgaccctgga    3060
aggtgccact cccactgtcc tttcctaata aaatgaggaa attgcatcgc attgtctgag    3120
taggtgtcat tctattctgg ggggtgggt ggggcaggac agcaagggg aggattggga    3180
agacaatagc aggcatgctg gggatgcggt gggctctatg gcttctgagg cggaaagaac    3240
cagctggggc tctagggggt atccccacgc gccctgtagc ggcgcattaa gcgcggcggg    3300
tgtggtggtt acgcgcagcg tgaccgctac acttgccagc gccctagcgc ccgctccttt    3360
```

```
cgctttcttc ccttcctttc tcgccacgtt cgccggcttt ccccgtcaag ctctaaatcg       3420
gggcatccct ttagggttcc gatttagtgc tttacggcac ctcgacccca aaaaacttga       3480
ttagggtgat ggttcacgta gtgggccatc gccctgatag acggttttc gcccttgac         3540 gttggagtcc acgttcttta atagtggact cttgttccaa actggaacaa cactcaaccc       3600
tatctcggtc tattcttttg atttataagg gattttgggg atttcggcct attggttaaa      3660
aaatgagctg atttaacaaa aatttaacgc gaattaattc tgtggaatgt gtgtcagtta       3720
gggtgtggaa agtccccagg ctccccaggc aggcagaagt atgcaaagca tgcatctcaa       3780
ttagtcagca accaggtgtg gaaagtcccc aggctcccca gcaggcagaa gtatgcaaag       3840
catgcatctc aattagtcag caaccatagt cccgccccta actccgccca tcccgcccct       3900
aactccgccc agtccgccc attctccgcc ccatggctga ctaattttt ttatttatgc         3960 agaggccgag gccgcctctg cctctgagct attccagaag tagtgaggag gcttttttgg       4020
aggcctaggc ttttgcaaaa agctcccggg agcttgtata tccattttcg gatctgatca       4080
gcacgtgatg aaaaagcctg aactcaccgc gacgtctgtc gagaagtttc tgatcgaaaa       4140
gttcgacagc gtctccgacc tgatgcagct ctcggagggc gaagaatctc gtgctttcag       4200
cttcgatgta ggagggcgtg gatatgtcct gcgggtaaat agctgcgccg atggtttcta       4260
caaagatcgt tatgtttatc ggcactttgc atcggccgcg ctcccgattc cggaagtgct       4320
tgacattggg gaattcagcg agagcctgac ctattgcatc tcccgccgtg cacgggtgt        4380 cacgttgcaa gacctgcctg aaaccgaact gcccgctgtt ctgcagccgg tcgcggaggc       4440
catggatgcg atcgctgcgg ccgatcttag ccagacgagc gggttcggcc cattcggacc       4500
gcaaggaatc ggtcaataca ctacatggcg tgatttcata tgcgcgattg ctgatcccca       4560
tgtgtatcac tggcaaactg tgatggacga caccgtcagt gcgtccgtcg cgcaggctct       4620
cgatgagctg atgctttggg ccgaggactg ccccgaagtc cggcacctcg tgcacgcgga       4680
tttcggctcc aacaatgtcc tgacggacaa tggccgcata acagcggtca ttgactggag       4740
cgaggcgatg ttcggggatt cccaatacga ggtcgccaac atcttcttct ggaggccgtg       4800
gttggcttgt atggagcagc agacgcgcta cttcgagcgg aggcatccgg agcttgcagg       4860
atcgccgcgg ctccgggcgt atatgctccg cattggtctt gaccaactct atcagagctt       4920
ggttgacggc aatttcgatg atgcagcttg ggcgcagggt cgatgcgacg caatcgtccg       4980
atccggagcc gggactgtcg gcgtacaca aatcgcccgc agaagcgcgg ccgtctggac        5040
cgatggctgt gtagaagtac tcgccgatag tggaaaccga cgccccagca ctcgtccgag       5100
ggcaaaggaa tagcacgtgc tacgagattt cgattccacc gccgccttct atgaaaggtt       5160
gggcttcgga atcgttttcc gggacgccgg ctggatgatc ctccagcgcg ggatctcat       5220 gctggagttc ttcgcccacc ccaacttgtt tattgcagct tataatggtt acaaataaag       5280
caatagcatc acaaatttca caaataaagc attttttca ctgcattcta gttgtggttt       5340
gtccaaactc atcaatgtat cttatcatgt ctgtataccg tcgacctcta gctagagctt       5400
ggcgtaatca tggtcatagc tgtttcctgt gtgaaattgt tatccgctca caattccaca       5460
caacatacga gccggaagca taaagtgtaa agcctgggt gcctaatgag tgagctaact       5520
cacattaatt gcgttgcgct cactgcccgc tttccagtcg ggaaacctgt cgtgccagct       5580
gcattaatga atcggccaac gcgcggggag aggcggtttg cgtattggc gctcttccgc       5640 ttcctcgctc actgactcgc tgcgctcggt cgttcggctg cggcgagcgg tatcagctca      5700
ctcaaaggcg gtaatacggt tatccacaga atcagggat aacgcaggaa agaacatgtg       5760
```

```
agcaaaaggc cagcaaaagg ccaggaaccg taaaaaggcc gcgttgctgg cgttttttcca    5820 taggctccgc ccccctgacg agcatcacaa aaatcgacgc tcaagtcaga ggtggcgaaa    5880
cccgacagga ctataaagat accaggcgtt tccccctgga agctccctcg tgcgctctcc    5940
tgttccgacc ctgccgctta ccggatacct gtccgccttt ctcccttcgg aagcgtggc    6000 gctttctcaa tgctcacgct gtaggtatct cagttcggtg taggtcgttc gctccaagct    6060
gggctgtgtg cacgaacccc ccgttcagcc cgaccgctgc gccttatccg gtaactatcg    6120
tcttgagtcc aacccggtaa gacacgactt atcgccactg gcagcagcca ctggtaacag    6180
gattagcaga gcgaggtatg taggcggtgc tacagagttc ttgaagtggt ggcctaacta    6240
cggctacact agaaggacag tatttggtat ctgcgctctg ctgaagccag ttaccttcgg    6300
aaaaagagtt ggtagctctt gatccggcaa acaaaccacc gctggtagcg gtggtttttt    6360
tgtttgcaag cagcagatta cgcgcagaaa aaaaggatct caagaagatc ctttgatctt    6420
ttctacgggg tctgacgctc agtggaacga aaactcacgt taagggattt tggtcatgag    6480
attatcaaaa aggatcttca cctagatcct tttaaattaa aaatgaagtt ttaaatcaat    6540
ctaaagtata tatgagtaaa cttggtctga cagttaccaa tgcttaatca gtgaggcacc    6600
tatctcagcg atctgtctat ttcgttcatc catagttgcc tgactccccg tcgtgtagat    6660
aactacgata cgggagggct taccatctgg ccccagtgct gcaatgatac cgcgagaccc    6720
acgctcaccg gctccagatt tatcagcaat aaaccagcca gccggaaggg ccgagcgcag    6780
aagtggtcct gcaactttat ccgcctccat ccagtctatt aattgttgcc gggaagctag    6840
agtaagtagt tcgccagtta atagtttgcg caacgttgtt gccattgcta caggcatcgt    6900
ggtgtcacgc tcgtcgtttg gtatggcttc attcagctcc ggttcccaac gatcaaggcg    6960
agttacatga tcccccatgt tgtgcaaaaa agcggttagc tccttcggtc ctccgatcgt    7020
tgtcagaagt aagttggccg cagtgttatc actcatggtt atggcagcac tgcataattc    7080
tcttactgtc atgccatccg taagatgctt ttctgtgact ggtgagtact caaccaagtc    7140
attctgagaa tagtgtatgc ggcgaccgag ttgctcttgc ccggcgtcaa tacgggataa    7200
taccgcgcca catagcagaa ctttaaaagt gctcatcatt ggaaaacgtt cttcggggcg    7260
aaaactctca aggatcttac cgctgttgag atccagttcg atgtaaccca ctcgtgcacc    7320
caactgatct tcagcatctt ttactttcac cagcgtttct gggtgagcaa aaacaggaag    7380
gcaaaatgcc gcaaaaaagg gaataagggc gacacggaaa tgttgaatac tcatactctt    7440 ccttttcaa tattattgaa gcatttatca gggttattgt ctcatgagcg gatacatatt    7500
tgaatgtatt tagaaaaata aacaaatagg ggttccgcgc acatttcccc gaaaagtgcc    7560
acctgacgtc                                                          7570
```

<210> SEQ ID NO 3
<211> LENGTH: 7597
<212> TYPE: DNA
<213> ORGANISM: Artificial Sequence
<220> FEATURE:
<223> OTHER INFORMATION: Plasmid

<400> SEQUENCE: 3

```
gacggatcgg gagatctccc gatccccat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
```

```
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
ggtaccaagc ttggatctca ccatgggtc aaccgccatc ctcaccatgg agttgggct     960
gcgctgggtt ctcctcgttg ctcttttaag aggtgtccag tgtcaggtgc agctggtgga   1020
gtctggggga ggcgtggtcc agcctgggag gtccctgaga ctctcctgtg cagcgtctgg   1080
attcaccttc agtaactatg tcatgcactg ggtccgccag gctccaggca aggggctgga   1140
gtgggtggca attatatggt atgatggaag taataaatac tatgcagact ccgtgaaggg   1200
ccgattcacc atctccagag acaattccaa gaacacgctg tatctgcaaa tgaacagcct   1260
gagagccgag gacacggctg tgtattactg tgcgggtgga tataactgga actacgagta   1320
ccactactac ggtatggacg tctggggcca agggaccacg gtcaccgtct cctcagcctc   1380
caccaagggc ccatcggtct tccccctggc accctctagc aagagcacct ctgggggcac   1440
agcggccctg ggctgcctgg tcaaggacta cttccccgaa ccggtgacgg tgtcgtggaa   1500
ctcaggcgcc ctgaccagcg gcgtgcacac cttcccggct gtcctacagt cctcaggact   1560
ctactccctc agcagcgtgg tgaccgtgcc ctccagcagc ttgggcaccc agacctacat   1620
ctgcaacgtg aatcacaagc ccagcaacac caaggtggac aagagagttg gtgagaggcc   1680
agcacaggga gggagggtgt ctgctggaag ccaggctcag cgctcctgcc tggacgcatc   1740
ccggctatgc agtcccagtc agggcagca aggcaggccc cgtctgcctc ttcacccgga   1800
ggcctctgcc cgccccactc atgctcaggg agagggtctt ctggcttttt ccccaggctc   1860
tgggcaggca caggctaggt gcccctaacc caggccctgc acacaaaggg gcaggtgctg   1920
ggctcagacc tgccaagagc catatccggg aggaccctgc cctgacctaa gcccacccc   1980
aaaggccaaa ctctccactc cctcagctcg acaccttct ctcctcccag attccagtaa   2040
ctcccaatct tctctctgca gagcccaaat cttgtgacaa aactcacaca tgcccaccgt   2100
gcccaggtaa gccagcccag gcctcgccct ccagctcaag gcgggacagg tgccctagag   2160
tagcctgcat ccagggacag gccccagccg ggtgctgaca cgtccacctc catctcttcc   2220
tcagcacctg aactcctggg gggaccgtca gtcttcctct tccccccaaa acccaaggac   2280
accctcatga tctcccggac ccctgaggtc acatgcgtgg tggtggacgt gagccacgaa   2340
gaccctgagg tcaagttcaa ctggtacgtg gacggcgtgg aggtgcataa tgccaagaca   2400
aagccgcggg aggagcagta caacagcacg taccgtgtgg tcagcgtcct caccgtcctg   2460
caccaggact ggctgaatgg caaggagtac aagtgcaagg tctccaacaa agccctccca   2520
gcccccatcg agaaaaccat ctccaaagcc aaaggtggga cccgtggggt gcgagggcca   2580
```

```
catggacaga ggccggctcg gcccaccctc tgccctgaga gtgaccgctg taccaacctc    2640
tgtccctaca gggcagcccc gagaaccaca ggtgtacacc ctgcccccat cccgggagga    2700
gatgaccaag aaccaggtca gcctgacctg cctggtcaaa ggcttctatc ccagcgacat    2760
cgccgtggag tgggagagca atgggcagcc ggagaacaac tacaagacca cgcctcccgt    2820
gctggactcc gacggctcct tcttcctcta tagcaagctc accgtggaca gagcaggtg    2880 gcagcagggg aacgtcttct catgctccgt gatgcatgag gctctgcaca accactacac    2940
gcagaagagc ctctccctgt ctccgggtaa atgagaattc ctcgagtcta gagggcccgt    3000
ttaaacccgc tgatcagcct cgactgtgcc ttctagttgc cagccatctg ttgtttgccc    3060
ctcccccgtg ccttccttga ccctggaagg tgccactccc actgtccttt cctaataaaa    3120
tgaggaaatt gcatcgcatt gtctgagtag gtgtcattct attctggggg gtggggtggg    3180
gcaggacagc aagggggagg attgggaaga caatagcagg catgctgggg atgcggtggg    3240
ctctatggct tctgaggcgg aaagaaccag ctggggctct aggggggtatc cccacgcgcc    3300 ctgtagcggc gcattaagcg cggcgggtgt ggtggttacg cgcagcgtga ccgctacact    3360
tgccagcgcc ctagcgcccg ctcctttcgc tttcttccct tcctttctcg ccacgttcgc    3420
cggctttccc cgtcaagctc taaatcgggg catccctta gggttccgat ttagtgcttt    3480
acggcacctc gaccccaaaa aacttgatta gggtgatggt tcacgtagtg gccatcgcc    3540 ctgatagacg ttttttcgcc ctttgacgtt ggagtccacg ttctttaata gtggactctt    3600
gttccaaact ggaacaacac tcaacccctat ctcggtctat tcttttgatt tataagggat    3660
tttggggatt tcggcctatt ggttaaaaaa tgagctgatt taacaaaaat ttaacgcgaa    3720
ttaattctgt ggaatgtgtg tcagttaggg tgtggaaagt ccccaggctc cccaggcagg    3780
cagaagtatg caaagcatgc atctcaatta gtcagcaacc aggtgtggaa agtccccagg    3840
ctccccagca ggcagaagta tgcaaagcat gcatctcaat tagtcagcaa ccatagtccc    3900
gcccctaact ccgcccatcc cgcccctaac tccgcccagt tccgcccatt ctccgcccca    3960
tggctgacta atttttttta tttatgcaga ggccgaggcc gcctctgcct ctgagctatt    4020
ccagaagtag tgaggaggct ttttggagg cctaggcttt tgcaaaaagc tcccgggagc    4080
ttgtatatcc attttcggat ctgatcagca cgtgatgaaa aagcctgaac tcaccgcgac    4140
gtctgtcgag aagtttctga tcgaaaagtt cgacagcgtc tccgacctga tgcagctctc    4200
ggagggcgaa gaatctcgtg ctttcagctt cgatgtagga gggcgtggat atgtcctgcg    4260
ggtaaatagc tgcgccgatg gtttctacaa agatcgttat gtttatcggc actttgcatc    4320
ggccgcgctc ccgattccgg aagtgcttga cattggggaa ttcagcgaga gcctgaccta    4380
ttgcatctcc cgccgtgcac agggtgtcac gttgcaagac ctgcctgaaa ccgaactgcc    4440
cgctgttctg cagccggtcg cggaggccat ggatgcgatc gctgcggccg atcttagcca    4500
gacgagcggg ttcggcccat tcggaccgca aggaatcggt caatacacta catggcgtga    4560
tttcatatgc gcgattgctg atccccatgt gtatcactgg caaactgtga tggacgacac    4620
cgtcagtgcg tccgtcgcgc aggctctcga tgagctgatg ctttgggccg aggactgccc    4680
cgaagtccgg cacctcgtgc acgcggattt cggctccaac aatgtcctga cggacaatgg    4740
ccgcataaca gcggtcattg actggagcga ggcgatgttc gggattccc aatacgaggt    4800 cgccaacatc ttcttctgga ggccgtggtt ggcttgtatg gagcagcaga cgcgctactt    4860
cgagcggagg catccggagc ttgcaggatc gccgcggctc cgggcgtata tgctccgcat    4920
```

```
tggtcttgac caactctatc agagcttggt tgacggcaat ttcgatgatg cagcttgggc    4980
gcagggtcga tgcgacgcaa tcgtccgatc cggagccggg actgtcgggc gtacacaaat    5040
cgcccgcaga agcgcggccg tctggaccga tggctgtgta aagtactcg ccgatagtgg     5100 aaaccgacgc cccagcactc gtccgagggc aaaggaatag cacgtgctac gagatttcga    5160
ttccaccgcc gccttctatg aaaggttggg cttcggaatc gttttccggg acgccggctg    5220
gatgatcctc cagcgcgggg atctcatgct ggagttcttc gcccacccca acttgtttat    5280
tgcagcttat aatggttaca ataaagcaa  tagcatcaca aatttcacaa ataaagcatt    5340
tttttcactg cattctagtt gtggtttgtc caaactcatc aatgtatctt atcatgtctg    5400
tataccgtcg acctctagct agagcttggc gtaatcatgg tcatagctgt ttcctgtgtg    5460
aaattgttat ccgctcacaa ttccacacaa catacgagcc ggaagcataa agtgtaaagc    5520
ctggggtgcc taatgagtga gctaactcac attaattgcg ttgcgctcac tgcccgcttt    5580
ccagtcggga acctgtcgt gccagctgca ttaatgaatc ggccaacgcg cggggagagg     5640
cggtttgcgt attgggcgct cttccgcttc ctcgctcact gactcgctgc gctcggtcgt    5700
tcggctgcgg cgagcggtat cagctcactc aaaggcggta atacggttat ccacagaatc    5760
aggggataac gcaggaaaga acatgtgagc aaaaggccag caaaaggcca ggaaccgtaa    5820
aaaggccgcg ttgctggcgt ttttccatag gctccgcccc cctgacgagc atcacaaaaa    5880
tcgacgctca agtcagaggt ggcgaaaccc gacaggacta taaagatacc aggcgtttcc    5940
ccctggaagc tccctcgtgc gctctcctgt tccgaccctg ccgcttaccg gatacctgtc    6000
cgcctttctc ccttcgggaa gcgtggcgct ttctcaatgc tcacgctgta ggtatctcag    6060
ttcggtgtag gtcgttcgct ccaagctggg ctgtgtgcac gaaccccccg ttcagcccga    6120
ccgctgcgcc ttatccggta actatcgtct tgagtccaac ccggtaagac acgacttatc    6180
gccactggca gcagccactg gtaacaggat tagcagagcg aggtatgtag cggtgctac     6240 agagttcttg aagtggtggc ctaactacgg ctacactaga aggacagtat ttggtatctg    6300
cgctctgctg aagccagtta ccttcggaaa aagagttggt agctcttgat ccggcaaaca    6360
aaccaccgct ggtagcggtg ttttttttgt ttgcaagcag cagattacgc gcagaaaaaa    6420
aggatctcaa gaagatcctt tgatctttc  tacggggtct gacgctcagt ggaacgaaaa    6480
ctcacgttaa gggattttgg tcatgagatt atcaaaaagg atcttcacct agatcctttt    6540
aaattaaaaa tgaagtttta atcaatcta  aagtatatat gagtaaactt ggtctgacag    6600
ttaccaatgc ttaatcagtg aggcaccta  tctcagcgatc tgtctatttc gttcatccat    6660
agttgcctga ctccccgtcg tgtagataac tacgatacgg gagggcttac catctggccc    6720
cagtgctgca atgataccgc gagacccacg ctcaccggct ccagatttat cagcaataaa    6780
ccagccagcc ggaagggccg agcgcagaag tggtcctgca actttatccg cctccatcca    6840
gtctattaat tgttgccggg aagctagagt aagtagttcg ccagttaata gtttgcgcaa    6900
cgttgttgcc attgctacag gcatcgtggt gtcacgctcg tcgtttggta tggcttcatt    6960
cagctccggt tcccaacgat caaggcgagt tacatgatcc cccatgttgt gcaaaaaagc    7020
ggttagctcc ttcggtcctc cgatcgttgt cagaagtaag ttggccgcag tgttatcact    7080
catggttatg gcagcactgc ataattctct tactgtcatg ccatccgtaa gatgcttttc    7140
tgtgactggt gagtactcaa ccaagtcatt ctgagaatag tgtatgcggc gaccgagttg    7200
ctcttgcccg gcgtcaatac gggataatac cgcgccacat agcagaactt taaaagtgct    7260
catcattgga aaacgttctt cggggcgaaa actctcaagg atcttaccgc tgttgagatc    7320
```

```
cagttcgatg taacccactc gtgcacccaa ctgatcttca gcatctttta ctttcaccag    7380
cgtttctggg tgagcaaaaa caggaaggca aaatgccgca aaaaagggaa taagggcgac    7440
acggaaatgt tgaatactca tactcttcct ttttcaatat tattgaagca tttatcaggg    7500
ttattgtctc atgagcggat acatatttga atgtatttag aaaaataaac aaatagggt     7560 tccgcgcaca tttccccgaa aagtgccacc tgacgtc                             7597
```

<210> SEQ ID NO 4
<211> LENGTH: 7579
<212> TYPE: DNA
<213> ORGANISM: Artificial Sequence
<220> FEATURE:
<223> OTHER INFORMATION: Plasmid

<400> SEQUENCE: 4

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctaga     900
ggtaccaagc ttggatctca ccatggagtt gggacttagc tgggttttcc tcgttgctct     960
tttaagaggt gtccagtgtc aggtccagct ggtggagtct ggggggaggcg tggtccagcc    1020 tgggaggtcc ctgagactct cctgtgcagc gtctggattc accttcagta gctatggcat    1080
gcactgggtc cgccaggctc aggcaaggg ctggactgg gtggcaatta tttggcatga     1140
tggaagtaat aaatactatg cagactccgt gaagggccga ttcaccatct ccagagacaa    1200
ttccaagaag acgctgtacc tgcaaatgaa cagtttgaga gccgaggaca cggctgtgta    1260
ttactgtgcg agagcttggg cctatgacta cggtgactat gaatactact cggtatgga     1320 cgtctggggc caaggaccca ccgtcaccgt ctcctcagcc tccaccaagg gcccatcggt    1380
cttccccctg gcaccctcta gcaagagcac ctctggggc acagcggccc tgggctgcct    1440
ggtcaaggac tacttccccg aaccggtgac ggtgtcgtgg aactcaggcg ccctgaccag    1500
cggcgtgcac accttcccgg ctgtcctaca gtcctcagga ctctactccc tcagcagcgt    1560
ggtgaccgtg ccctccagca gcttgggcac ccagacctac atctgcaacg tgaatcacaa    1620
gcccagcaac accaaggtgg acaagagagt tggtgagagg ccagcacagg gagggagggt    1680
gtctgctgga agccaggctc agcgctcctg cctggacgca tcccggctat gcagtcccag    1740
```

```
tccagggcag caaggcaggc cccgtctgcc tcttcacccg gaggcctctg cccgcccac    1800 tcatgctcag ggagagggtc ttctggcttt ttccccaggc tctgggcagg cacaggctag   1860
gtgcccctaa cccaggccct gcacacaaag gggcaggtgc tgggctcaga cctgccaaga   1920
gccatatccg ggaggaccct gcccctgacc taagcccacc ccaaaggcca aactctccac   1980
tccctcagct cggacaccct tctcctccc agattccagt aactcccaat cttctctctg    2040
cagagcccaa atcttgtgac aaaactcaca catgcccacc gtgcccaggt aagccagccc   2100
aggcctcgcc ctccagctca aggcgggaca ggtgccctag agtagcctgc atccagggac   2160
aggccccagc cgggtgctga cacgtccacc tccatctctt cctcagcacc tgaactcctg   2220
gggggaccgt cagtcttcct cttcccccca aacccaagg acaccctcat gatctcccgg    2280
acccctgagg tcacatgcgt ggtggtggac gtgagccacg aagaccctga ggtcaagttc   2340
aactggtacg tggacggcgt ggaggtgcat aatgccaaga caaagccgcg ggaggagcag   2400
tacaacagca cgtaccgtgt ggtcagcgtc ctcaccgtcc tgcaccagga ctggctgaat   2460
ggcaaggagt acaagtgcaa ggtctccaac aaagccctcc cagcccccat cgagaaaacc   2520
atctccaaag ccaaaggtgg acccgtgggg gtgcgagggc cacatggaca gaggccggct   2580
cggcccaccc tctgccctga gagtgaccgc tgtaccaacc tctgtcccta cagggcagcc   2640
ccgagaacca caggtgtaca ccctgccccc atcccgggag gagatgacca agaaccaggt   2700
cagcctgacc tgcctggtca aaggcttcta tcccagcgac atcgccgtgg agtgggagag   2760
caatgggcag ccggagaaca actacaagac cacgcctccc gtgctggact ccgacggctc   2820
cttcttcctc tatagcaagc tcaccgtgga caagagcagg tggcagcagg gaacgtcttc   2880
ctcatgctcc gtgatgcatg aggctctgca caaccactac acgcagaaga gcctctccct   2940
gtctccgggt aaatgagaat tcctcgagtc tagagggccc gtttaaaccc gctgatcagc   3000
ctcgactgtg ccttctagtt gccagccatc tgttgtttgc ccctccccg tgccttcctt    3060 gaccctggaa ggtgccactc ccactgtcct ttcctaataa aatgaggaaa ttgcatcgca   3120
ttgtctgagt aggtgtcatt ctattctggg gggtggggtg ggcaggaca gcaaggggga    3180 ggattgggaa gacaatagca ggcatgctgg ggatgcggtg ggctctatgg cttctgaggc   3240
ggaaagaacc agctggggct ctaggggta tccccacgcg ccctgtagcg gcgcattaag    3300
cgcggcgggt gtggtggtta cgcgcagcgt gaccgctaca cttgccagcg ccctagcgcc   3360
cgctcctttc gctttcttcc cttcctttct cgccacgttc gccggctttc cccgtcaagc   3420
tctaaatcgg ggcatccctt tagggttccg atttagtgct ttacggcacc tcgaccccaa   3480
aaaacttgat tagggtgatg gttcacgtag tgggccatcg ccctgataga cggtttttcg   3540
ccctttgacg ttggagtcca cgttctttaa tagtggactc ttgttccaaa ctggaacaac   3600
actcaaccct atctcggtct attcttttga tttataaggg attttgggga tttcggccta   3660
ttggttaaaa aatgagctga tttaacaaaa atttaacgcg aattaattct gtggaatgtg   3720
tgtcagttag ggtgtggaaa gtccccaggc tccccaggca ggcagaagta tgcaaagcat   3780
gcatctcaat tagtcagcaa ccaggtgtgg aaagtcccca ggctcccccag caggcagaag  3840 tatgcaaagc atgcatctca attagtcagc aaccatagtc cgcccctaa ctccgcccat    3900 cccgccccta actccgccca gttccgccca ttctccgccc catggctgac taattttttt   3960
tatttatgca gaggccgagg ccgcctctgc ctctgagcta ttccagaagt agtgaggagg   4020
cttttttgga ggcctaggct tttgcaaaaa gctcccggga gcttgtatat ccattttcgg   4080
atctgatcag cacgtgatga aaaagcctga actcaccgcg acgtctgtcg agaagtttct   4140
```

```
gatcgaaaag ttcgacagcg tctccgacct gatgcagctc tcggagggcg aagaatctcg    4200
tgctttcagc ttcgatgtag gagggcgtgg atatgtcctg cgggtaaata gctgcgccga    4260
tggtttctac aaagatcgtt atgtttatcg gcactttgca tcggccgcgc tcccgattcc    4320
ggaagtgctt gacattgggg aattcagcga gagcctgacc tattgcatct cccgccgtgc    4380
acagggtgtc acgttgcaag acctgcctga aaccgaactg cccgctgttc tgcagccggt    4440
cgcggaggcc atggatgcga tcgctgcggc cgatcttagc cagacgagcg ggttcggccc    4500
attcggaccg caaggaatcg gtcaatacac tacatggcgt gatttcatat gcgcgattgc    4560
tgatccccat gtgtatcact ggcaaactgt gatggacgac accgtcagtg cgtccgtcgc    4620
gcaggctctc gatgagctga tgctttgggc cgaggactgc cccgaagtcc ggcacctcgt    4680
gcacgcggat ttcggctcca acaatgtcct gacgacaat ggccgcataa cagcggtcat     4740
tgactggagc gaggcgatgt tcggggattc ccaatacgag gtcgccaaca tcttcttctg    4800
gaggccgtgg ttggcttgta tggagcagca gacgcgctac ttcgagcgga ggcatccgga    4860
gcttgcagga tcgccgcggc tccgggcgta tatgctccgc attggtcttg accaactcta    4920
tcagagcttg gttgacggca atttcgatga tgcagcttgg gcgcagggtc gatgcgacgc    4980
aatcgtccga tccggagccg ggactgtcgg gcgtacacaa atcgcccgca gaagcgcggc    5040
cgtctggacc gatggctgtg tagaagtact cgccgatagt ggaaaccgac gcccagcac     5100 tcgtccgagg gcaaaggaat agcacgtgct acgagatttc gattccaccg ccgccttcta    5160
tgaaaggttg ggcttcggaa tcgttttccg ggacgccggc tggatgatcc tccagcgcgg    5220
ggatctcatg ctggagttct tcgcccaccc caacttgttt attgcagctt ataatggtta    5280
caaataaagc aatagcatca caaatttcac aaataaagca ttttttttcac tgcattctag    5340 ttgtggtttg tccaaactca tcaatgtatc ttatcatgtc tgtataccgt cgacctctag    5400
ctagagcttg gcgtaatcat ggtcatagct gtttcctgtg tgaaattgtt atccgctcac    5460
aattccacac aacatacgag ccggaagcat aaagtgtaaa gcctggggtg cctaatgagt    5520
gagctaactc acattaattg cgttgcgctc actgcccgct ttccagtcgg gaaacctgtc    5580
gtgccagctg cattaatgaa tcggccaacg cgcggggaga ggcggtttgc gtattgggcg    5640
ctcttccgct tcctcgctca ctgactcgct gcgctcggtc gttcggctgc ggcgagcggt    5700
atcagctcac tcaaaggcgg taatacggtt atccacagaa tcaggggata acgcaggaaa    5760
gaacatgtga gcaaaaggcc agcaaaaggc caggaaccgt aaaaaggccg cgttgctggc    5820 gttttccat aggctccgcc cccctgacga gcatcacaaa aatcgacgct caagtcagag      5880
gtggcgaaac ccgacaggac tataaagata ccaggcgttt ccccctggaa gctccctcgt    5940
gcgctctcct gttccgaccc tgccgcttac cggatacctg tccgcctttc tcccttcggg    6000
aagcgtggcg ctttctcaat gctcacgctg taggtatctc agttcggtgt aggtcgttcg    6060
ctccaagctg ggctgtgtgc acgaaccccc cgttcagccc gaccgctgcg ccttatccgg    6120
taactatcgt cttgagtcca acccggtaag acacgactta tcgccactgg cagcagccac    6180
tggtaacagg attagcagag cgaggtatgt aggcggtgct acagagttct tgaagtggtg    6240
gcctaactac ggctacacta aggacagt atttggtatc tgcgctctgc tgaagccagt       6300
taccttcgga aaaagagttg gtagctcttg atccggcaaa caaaccaccg ctggtagcgg    6360
tggttttttt gtttgcaagc agcagattac gcgcagaaaa aaaggatctc aagaagatcc    6420
tttgatcttt tctacggggt ctgacgctca gtggaacgaa aactcacgtt aagggatttt    6480
```

```
ggtcatgaga ttatcaaaaa ggatcttcac ctagatcctt ttaaattaaa aatgaagttt      6540
taaatcaatc taaagtatat atgagtaaac ttggtctgac agttaccaat gcttaatcag      6600
tgaggcacct atctcagcga tctgtctatt tcgttcatcc atagttgcct gactccccgt      6660
cgtgtagata actacgatac gggagggctt accatctggc cccagtgctg caatgatacc      6720
gcgagaccca cgctcaccgg ctccagattt atcagcaata aaccagccag ccggaagggc      6780
cgagcgcaga gtggtcctg caactttatc cgcctccatc cagtctatta attgttgccg      6840
ggaagctaga gtaagtagtt cgccagttaa tagtttgcgc aacgttgttg ccattgctac      6900
aggcatcgtg gtgtcacgct cgtcgtttgg tatggcttca ttcagctccg gttcccaacg      6960
atcaaggcga gttacatgat cccccatgtt gtgcaaaaaa gcggttagct ccttcggtcc      7020
tccgatcgtt gtcagaagta agttggccgc agtgttatca ctcatggtta tggcagcact      7080
gcataattct cttactgtca tgccatccgt aagatgcttt tctgtgactg gtgagtactc      7140
aaccaagtca ttctgagaat agtgtatgcg gcgaccgagt tgctcttgcc cggcgtcaat      7200
acgggataat accgcgccac atagcagaac tttaaaagtg ctcatcattg gaaaacgttc      7260
ttcggggcga aaactctcaa ggatcttacc gctgttgaga tccagttcga tgtaacccac      7320
tcgtgcaccc aactgatctt cagcatcttt tactttcacc agcgtttctg ggtgagcaaa      7380
aacaggaagg caaaatgccg caaaaaaggg aataagggcg acacggaaat gttgaatact      7440
catactcttc ctttttcaat attattgaag catttatcag ggttattgtc tcatgagcgg      7500
atacatattt gaatgtattt agaaaaataa acaaataggg gttccgcgca catttccccg      7560
aaaagtgcca cctgacgtc                                                   7579

<210> SEQ ID NO 5
<211> LENGTH: 7558
<212> TYPE: DNA
<213> ORGANISM: Artificial Sequence
<220> FEATURE:
<223> OTHER INFORMATION: Plasmid

<400> SEQUENCE: 5
gacggatcgg gagatctccc gatcccctat ggtcgactct cagtacaatc tgctctgatg        60
ccgcatagtt aagccagtat ctgctccctg cttgtgtgtt ggaggtcgct gagtagtgcg       120
cgagcaaaat ttaagctaca acaaggcaag gcttgaccga caattgcatg aagaatctgc       180
ttagggttag gcgttttgcg ctgcttcgcg atgtacgggc cagatatacg cgttgacatt       240
gattattgac tagttattaa tagtaatcaa ttacggggtc attagttcat agcccatata       300
tggagttccg cgttacataa cttacggtaa atggcccgcc tggctgaccg cccaacgacc       360
cccgcccatt gacgtcaata atgacgtatg ttcccatagt aacgccaata gggactttcc       420
attgacgtca atgggtggac tatttacggt aaactgccca cttggcagta catcaagtgt       480
atcatatgcc aagtacgccc cctattgacg tcaatgacgg taaatggccc gcctggcatt       540
atgcccagta catgacctta tgggactttc ctacttggca gtacatctac gtattagtca       600
tcgctattac catggtgatg cggttttggc agtacatcaa tgggcgtgga tagcggtttg       660
actcacgggg atttccaagt ctccacccca ttgacgtcaa tgggagtttg ttttggcacc       720
aaaatcaacg ggactttcca aaatgtcgta acaactccgc cccattgacg caaatgggcg       780
gtaggcgtgt acggtgggag gtctatataa gcagagctct ctggctaact agagaaccca       840
ctgcttactg gcttatcgaa attaatacga ctcactatag ggagacccaa gctggctaga       900
ggtaccaagc ttggatccca ccatggggtc aaccgtcatc ctcgccctcc tcctggctgt       960
```

```
tctccaagga gtctgtgccg aggtgcagct ggtgcagtct ggagcagagg tgaaaaagcc    1020
cggggagtct ctgaagatct cctgtaaggg ttctggatac agctttacca gttactggat    1080
cggctgggtg cgccagatgc ccgggaaagg cctggagtgg atggggatca tctatcctgg    1140
tgactctgat accagataca gcccgtcctt ccaaggccag gtcaccatct cagccgacaa    1200
gtccatcagc accgcctacc tgcagtggag cagcctgaag gcctcggaca ccgccatgta    1260
ttactgtgcg agacggatgg cagcagctgg ccccttttgac tactgggcc agggaaccct    1320 ggtcaccgtc tcctcagcct ccaccaaggg cccatcggtc ttccccctgg caccctctag    1380
caagagcacc tctgggggca gcggcccct gggctgcctg gtcaaggact acttccccga    1440
accggtgacg gtgtcgtgga actcaggcgc cctgaccagc ggcgtgcaca ccttcccggc    1500
tgtcctacag tcctcaggac tctactccct cagcagcgtg gtgaccgtgc cctccagcag    1560
cttgggcacc cagacctaca tctgcaacgt gaatcacaag cccagcaaca ccaaggtgga    1620
caagagagtt ggtgagaggc cagcacaggg agggagggtg tctgctggaa gccaggctca    1680
gcgctcctgc ctggacgcat cccggctatg cagtcccagt ccagggcagc aaggcaggcc    1740
ccgtctgcct cttcacccgg aggcctctgc ccgccccact catgctcagg gagagggtct    1800
tctggctttt tccccaggct ctgggcaggc acaggctagg tgcccctaac ccaggccctg    1860
cacacaaagg ggcaggtgct gggctcagac ctgccaagag ccatatccgg gaggaccctg    1920
cccctgacct aagcccaccc caaaggccaa actctccact ccctcagctc ggacaccttc    1980
tctcctccca gattccagta actcccaatc ttctctctgc agagcccaaa tcttgtgaca    2040
aaactcacac atgcccaccg tgcccaggta agccagccca ggcctcgccc tccagctcaa    2100
ggcgggacag gtgccctaga gtagcctgca tccaggaca ggccccagcc gggtgctgac    2160
acgtccacct ccatctcttc ctcagcacct gaactcctgg ggggaccgtc agtcttcctc    2220
ttccccccaa aacccaagga caccctcatg atctcccgga cccctgaggt cacatgcgtg    2280
gtggtggacg tgagccacga agaccctgag gtcaagttca actggtacgt ggacggcgtg    2340
gaggtgcata atgccaagac aaagccgcgg gaggagcagt acaacagcac gtaccgtgtg    2400
gtcagcgtcc tcaccgtcct gcaccaggac tggctgaatg gcaaggagta caagtgcaag    2460
gtctccaaca aagccctccc agcccccatc gagaaaacca tctccaaagc caaaggtggg    2520
acccgtgggg tgcgagggcc acatggacag aggccggctc ggcccaccct ctgccctgag    2580
agtgaccgct gtaccaacct ctgtccctac agggcagccc cgagaaccac aggtgtacac    2640 cctgcccca tcccgggagg agatgaccaa gaaccaggtc agcctgacct gcctggtcaa    2700
aggcttctat cccagcgaca tcgccgtgga gtgggagagc aatgggcagc cggagaacaa    2760
ctacaagacc acgcctcccg tgctggactc cgacggctcc ttcttcctct atagcaagct    2820
caccgtggac aagagcaggt ggcagcaggg gaacgtcttc tcatgctccg tgatgcatga    2880
ggctctgcac aaccactaca cgcagaagag cctctccctg tctccgggta atgagaatt    2940 cctcgagtct agagggcccg tttaaacccg ctgatcagcc tcgactgtgc cttctagttg    3000
ccagccatct gttgtttgcc cctcccccgt gccttccttg accctggaag gtgccactcc    3060
cactgtcctt tcctaataaa atgaggaaat tgcatcgcat tgtctgagta ggtgtcattc    3120
tattctgggg ggtgggggtgg ggcaggacag caagggggag gattgggaag acaatagcag    3180
gcatgctggg gatgcggtgg gctctatggc ttctgaggcg gaaagaacca gctgggctc    3240 tagggggtat ccccacgcgc cctgtagcgg cgcattaagc gcggcgggtg tggtggttac    3300
```

-continued

```
gcgcagcgtg accgctacac ttgccagcgc cctagcgccc gctcctttcg ctttcttccc      3360
ttcctttctc gccacgttcg ccggcttttcc ccgtcaagct ctaaatcggg gcatcccttt      3420
agggttccga tttagtgctt tacggcacct cgaccccaaa aaacttgatt agggtgatgg      3480
ttcacgtagt gggccatcgc cctgatagac ggttttttcgc cctttgacgt tggagtccac     3540
gttctttaat agtggactct tgttccaaac tggaacaaca ctcaacccta tctcggtcta      3600
ttcttttgat ttataaggga ttttggggat ttcggcctat tggttaaaaa atgagctgat      3660
ttaacaaaaa tttaacgcga attaattctg tggaatgtgt gtcagttagg gtgtggaaag     3720
tccccaggct ccccaggcag gcagaagtat gcaaagcatg catctcaatt agtcagcaac    3780
caggtgtgga aagtccccag gctccccagc aggcagaagt atgcaaagca tgcatctcaa    3840
ttagtcagca accatagtcc cgcccctaac tccgcccatc ccgccccctaa ctccgcccag   3900
ttccgcccat tctccgcccc atggctgact aatttttttt atttatgcag aggccgaggc    3960
cgcctctgcc tctgagctat tccagaagta gtgaggaggc tttttggag gcctaggctt      4020
ttgcaaaaag ctcccgggag cttgtatatc cattttcgga tctgatcagc acgtgatgaa    4080
aaagcctgaa ctcaccgcga cgtctgtcga agtttctg atcgaaaagt cgacagcgt       4140
ctccgacctg atgcagctct cggagggcga agaatctcgt gctttcagct tcgatgtagg   4200
agggcgtgga tatgtcctgc gggtaaatag ctgcgccgat ggtttctaca agatcgtta     4260
tgtttatcgg cactttgcat cggccgcgct cccgattccg gaagtgcttg acattgggga   4320
attcagcgag agcctgacct attgcatctc ccgccgtgca cagggtgtca cgttgcaaga   4380
cctgcctgaa accgaactgc ccgctgttct gcagccggtc gcggaggcca tggatgcgat   4440
cgctgcggcc gatcttagcc agacgagcgg gttcggccca ttcggaccgc aaggaatcgg   4500
tcaatacact acatggcgtg atttcatatg cgcgattgct gatccccatg tgtatcactg   4560
gcaaactgtg atggacgaca ccgtcagtgc gtccgtcgcg caggctctcg atgagctgat   4620
gctttgggcc gaggactgcc ccgaagtccg gcacctcgtg cacgcggatt tcggctccaa   4680
caatgtcctg acggacaatg gccgcataac agcggtcatt gactggagcg aggcgatgtt   4740
cggggattcc caatacgagg tcgccaacat cttcttctgg aggccgtggt tggcttgtat   4800
ggagcagcag acgcgctact tcgagcggag gcatccggag cttgcaggat cgccgcggct   4860
ccgggcgtat atgctccgca ttggtcttga ccaactctat cagagcttgg ttgacgcaa   4920
tttcgatgat gcagcttggg cgcagggtcg atgcgacgca atcgtccgat ccggagccgg   4980
gactgtcggg cgtacacaaa tcgcccgcag aagcgcggcc gtctggaccg atggctgtgt   5040
agaagtactc gccgatagtg gaaaccgacg ccccagcact cgtccgaggg caaaggaata   5100
gcacgtgcta cgagatttcg attccaccgc cgccttctat gaaaggttgg gcttcggaat   5160
cgttttccgg gacgccggct ggatgatcct ccagcgcggg gatctcatgc tggagttctt   5220
cgcccacccc aacttgttta ttgcagctta taatggttac aaataaagca atagcatcac   5280
aaatttcaca aataaagcat ttttttcact gcattctagt tgtggtttgt ccaaactcat   5340
caatgtatct tatcatgtct gtataccgtc gacctctagc tagagcttgg cgtaatcatg   5400
gtcatagctg tttcctgtgt gaaattgtta tccgctcaca attccacaca acatacgagc   5460
cggaagcata aagtgtaaag cctggggtgc ctaatgagtg agctaactca cattaattgc   5520
gttgcgctca ctgcccgctt tccagtcggg aaacctgtcg tgccagctgc attaatgaat   5580
cggccaacgc gcggggagag gcggtttgcg tattgggcgc tcttccgctt cctcgctcac   5640
tgactcgctg cgctcggtcg ttcggctgcg gcgagcggta tcagctcact caaaggcggt   5700
```

-continued

| | |
|---|---|
| aatacggtta tccacagaat caggggataa cgcaggaaag aacatgtgag caaaaggcca | 5760 |
| gcaaaaggcc aggaaccgta aaaaggccgc gttgctggcg ttttccata ggctccgccc | 5820 |
| ccctgacgag catcacaaaa atcgacgctc aagtcagagg tggcgaaacc cgacaggact | 5880 |
| ataaagatac caggcgtttc ccctggaag ctccctcgtg cgctctcctg ttccgaccct | 5940 |
| gccgcttacc ggatacctgt ccgcctttct cccttcggga agcgtggcgc tttctcaatg | 6000 |
| ctcacgctgt aggtatctca gttcggtgta ggtcgttcgc tccaagctgg gctgtgtgca | 6060 |
| cgaaccccc gttcagcccg accgctgcgc cttatccggt aactatcgtc ttgagtccaa | 6120 |
| cccggtaaga cacgacttat cgccactggc agcagccact ggtaacagga ttagcagagc | 6180 |
| gaggtatgta ggcggtgcta cagagttctt gaagtggtgg cctaactacg gctacactag | 6240 |
| aaggacagta tttggtatct gcgctctgct gaagccagtt accttcggaa aaagagttgg | 6300 |
| tagctcttga tccggcaaac aaaccaccgc tggtagcggt ggtttttttg tttgcaagca | 6360 |
| gcagattacg cgcagaaaaa aaggatctca agaagatcct ttgatctttt ctacggggtc | 6420 |
| tgacgctcag tggaacgaaa actcacgtta agggattttg gtcatgagat tatcaaaaag | 6480 |
| gatcttcacc tagatccttt taaattaaaa atgaagtttt aaatcaatct aaagtatata | 6540 |
| tgagtaaact tggtctgaca gttaccaatg cttaatcagt gaggcaccta tctcagcgat | 6600 |
| ctgtctattt cgttcatcca tagttgcctg actccccgtc gtgtagataa ctacgatacg | 6660 |
| ggagggctta ccatctggcc ccagtgctgc aatgataccg cgagacccac gctcaccggc | 6720 |
| tccagattta tcagcaataa accagccagc cggaagggcc gagcgcagaa gtggtcctgc | 6780 |
| aactttatcc gcctccatcc agtctattaa ttgttgccgg gaagctagag taagtagttc | 6840 |
| gccagttaat agtttgcgca acgttgttgc cattgctaca ggcatcgtgg tgtcacgctc | 6900 |
| gtcgtttggt atggcttcat tcagctccgg ttcccaacga tcaaggcgag ttacatgatc | 6960 |
| ccccatgttg tgcaaaaaag cggttagctc cttcggtcct ccgatcgttg tcagaagtaa | 7020 |
| gttggccgca gtgttatcac tcatggttat ggcagcactg cataattctc ttactgtcat | 7080 |
| gccatccgta agatgctttt ctgtgactgg tgagtactca accaagtcat tctgagaata | 7140 |
| gtgtatgcgg cgaccgagtt gctcttgccc ggcgtcaata cggataata ccgcgccaca | 7200 |
| tagcagaact ttaaaagtgc tcatcattgg aaaacgttct cggggcgaa aactctcaag | 7260 |
| gatcttaccg ctgttgagat ccagttcgat gtaacccact cgtgcaccca actgatcttc | 7320 |
| agcatctttt actttcacca gcgtttctgg gtgagcaaaa acaggaaggc aaaatgccgc | 7380 |
| aaaaaggga ataagggcga cacggaaatg ttgaatactc atactcttcc tttttcaata | 7440 |
| ttattgaagc atttatcagg gttattgtct catgagcgga tacatatttg aatgtattta | 7500 |
| gaaaaataaa caataggggg ttccgcgcac atttccccga aagtgccac ctgacgtc | 7558 |

<210> SEQ ID NO 6
<211> LENGTH: 7576
<212> TYPE: DNA
<213> ORGANISM: Artificial Sequence
<220> FEATURE:
<223> OTHER INFORMATION: Plasmid

<400> SEQUENCE: 6

| | |
|---|---|
| gacggatcgg gagatctccc gatccccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |

```
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggac tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctaga      900
ggtaccaagc ttggatctca ccatggagtt tgggctgtgc tggattttcc tcgttgctct      960
tttaagaggt gtccagtgtc aggtgcagct ggtggagtct gggggaggcg tggtccagcc     1020
tgggaggtcc ctgagactct cctgtgcagc ctctggattc accttcatta gctatggcat     1080
gcactgggtc cgccaggctc aggcaaggg gctggagtgg gtggcagtta tcatatga     1140 tggaagtaat aaatactatg cagactccgt gaagggccga ttcaccatct ccagagacaa     1200
ttccaagaac acgctgtatc tgcaaatgaa cagcctgaga gctgaggaca cggctgtgta     1260
ttactgtgcg agagtattag tgggagcttt atattattat aactactacg gatggacgt     1320 ctggggccaa gggaccacgg tcaccgtctc ctcagcctcc accaagggcc catcggtctt     1380 cccccctggca ccctctagca agagcacctc tgggggcaca gcggccctgg gctgcctggt     1440
caaggactac ttccccgaac cggtgacggt gtcgtggaac tcaggcgccc tgaccagcgg     1500
cgtgcacacc ttcccggctg tcctacagtc ctcaggactc tactccctca gcagcgtggt     1560
gaccgtgccc tccagcagct tgggcaccca gacctacatc tgcaacgtga atcacaagcc     1620
cagcaacacc aaggtggaca agagagttgg tgagaggcca gcacagggag ggagggtgtc     1680
tgctggaagc caggctcagc gctcctgcct ggacgcatcc cggctatgca gtcccagtcc     1740
agggcagcaa gcaggcccc gtctgcctct tcacccggag gcctctgccc gccccactca     1800
tgctcaggga gagggtcttc tggctttttc cccaggctct gggcaggcac aggctaggtg     1860
cccctaaccc aggccctgca cacaaagggg caggtgctgg gctcagacct gccaagagcc     1920
atatccggga ggaccctgcc cctgacctaa gcccacccca aaggccaaac tctccactcc     1980
ctcagctcgg acaccttctc tcctcccaga ttccagtaac tcccaatctt ctctctgcag     2040
agcccaaatc ttgtgacaaa actcacacat gcccaccgtg cccaggtaag ccagcccagg     2100
cctcgccctc cagctcaagg cgggacaggt gccctagagt agcctgcatc cagggacagg     2160
ccccagccgg gtgctgacac gtccacctcc atctcttcct cagcacctga actcctgggg     2220
ggaccgtcag tcttcctctt ccccccaaaa cccaaggaca cctcatgat ctcccggacc     2280 cctgaggtca catgcgtggt ggtggacgtg agccacgaag accctgaggt caagttcaac     2340
tggtacgtgg acggcgtgga ggtgcataat gccaagacaa agccgcggga ggagcagtac     2400
aacagcacgt accgtgtggt cagcgtcctc accgtcctgc accaggactg gctgaatggc     2460
aaggagtaca agtgcaaggt ctccaacaaa gccctcccag cccccatcga gaaaaccatc     2520
tccaaagcca aggtgggac ccgtggggtg cgagggccac atggacagag gccggctcgg     2580
```

```
cccaccctct gccctgagag tgaccgctgt accaacctct gtccctacag ggcagccccg    2640
agaaccacag gtgtacaccc tgcccccatc ccgggaggag atgaccaaga accaggtcag    2700
cctgacctgc ctggtcaaag gcttctatcc cagcgacatc gccgtggagt gggagagcaa    2760
tgggcagccg gagaacaact acaagaccac gcctcccgtg ctggactccg acggctcctt    2820
cttcctctat agcaagctca ccgtggacaa gagcaggtgg cagcagggga acgtcttctc    2880
atgctccgtg atgcatgagg ctctgcacaa ccactacacg cagaagagcc tctccctgtc    2940
tccgggtaaa tgagaattcc tcgagtctag agggcccgtt taaacccgct gatcagcctc    3000
gactgtgcct tctagttgcc agccatctgt tgtttgcccc tcccccgtgc cttccttgac    3060
cctggaaggt gccactccca ctgtcctttc ctaataaaat gaggaaattg catcgcattg    3120
tctgagtagg tgtcattcta ttctgggggg tggggtgggg caggacagca agggggagga    3180
ttgggaagac aatagcaggc atgctgggga tgcggtgggc tctatggctt ctgaggcgga    3240
aagaaccagc tggggctcta gggggtatcc ccacgcgccc tgtagcggcg cattaagcgc    3300
ggcgggtgtg gtggttacgc gcagcgtgac cgctacactt gccagcgccc tagcgcccgc    3360
tcctttcgct ttcttccctt cctttctcgc cacgttcgcc ggctttcccc gtcaagctct    3420
aaatcggggc atccctttag ggttccgatt tagtgcttta cggcacctcg accccaaaaa    3480
acttgattag ggtgatggtt cacgtagtgg gccatcgccc tgatagacgg ttttcgccc    3540 tttgacgttg gagtccacgt tctttaatag tggactcttg ttccaaactg gaacaacact    3600
caaccctatc tcggtctatt cttttgattt ataagggatt ttgggqattt cggcctattg    3660 gttaaaaaat gagctgattt aacaaaaatt taacgcgaat taattctgtg aatgtgtgt    3720 cagttagggt gtggaaagtc cccaggctcc ccaggcaggc agaagtatgc aaagcatgca    3780
tctcaattag tcagcaacca ggtgtggaaa gtccccaggc tccccagcag gcagaagtat    3840
gcaaagcatg catctcaatt agtcagcaac catagtcccg cccctaactc cgcccatccc    3900
gcccctaact ccgcccagtt ccgcccattc tccgccccat ggctgactaa ttttttttat    3960
ttatgcagag gccgaggccg cctctgcctc tgagctattc cagaagtagt gaggaggctt    4020
ttttggaggc ctaggctttt gcaaaaagct cccgggagct tgtatatcca ttttcggatc    4080
tgatcagcac gtgatgaaaa agcctgaact caccgcgacg tctgtcgaga agtttctgat    4140
cgaaaagttc gacagcgtct ccgacctgat gcagctctcg gagggcgaag aatctcgtgc    4200
tttcagcttc gatgtaggag ggcgtggata tgtcctgcgg gtaaatagct gcgccgatgg    4260
tttctacaaa gatcgttatg tttatcggca ctttgcatcg gccgcgctcc cgattccgga    4320
agtgcttgac attggggaat tcagcgagag cctgacctat tgcatctccc gccgtgcaca    4380
gggtgtcacg ttgcaagacc tgcctgaaac cgaactgccc gctgttctgc agccggtcgc    4440
ggaggccatg gatgcgatcg ctgcggccga tcttagccag acgagcgggt tcggcccatt    4500
cggaccgcaa ggaatcggtc aatacactac atggcgtgat ttcatatgcg cgattgctga    4560
tccccatgtg tatcactggc aaactgtgat ggacgacacc gtcagtgcgt ccgtcgcgca    4620
ggctctcgat gagctgatgc tttgggccga ggactgcccc gaagtccggc acctcgtgca    4680
cgcggatttc ggctccaaca atgtcctgac ggacaatggc cgcataacag cggtcattga    4740
ctggagcgag gcgatgttcg ggattcccca atacgaggtc gccaacatct tcttctggag    4800
gccgtggttg gcttgtatgg agcagcagac gcgctacttc gagcggaggc atccggagct    4860
tgcaggatcg ccgcggctcc gggcgtatat gctccgcatt ggtcttgacc aactctatca    4920
```

```
gagcttggtt gacggcaatt tcgatgatgc agcttgggcg cagggtcgat gcgacgcaat    4980
cgtccgatcc ggagccggga ctgtcgggcg tacacaaatc gcccgcagaa gcgcggccgt    5040
ctggaccgat ggctgtgtag aagtactcgc cgatagtgga aaccgacgcc ccagcactcg    5100
tccgagggca aaggaatagc acgtgctacg agatttcgat tccaccgccg ccttctatga    5160
aaggttgggc ttcggaatcg ttttccggga cgccggctgg atgatcctcc agcgcgggga    5220
tctcatgctg gagttcttcg cccaccccaa cttgtttatt gcagcttata atggttacaa    5280
ataaagcaat agcatcacaa atttcacaaa taaagcattt ttttcactgc attctagttg    5340
tggtttgtcc aaactcatca atgtatctta tcatgtctgt ataccgtcga cctctagcta    5400
gagcttggcg taatcatggt catagctgtt tcctgtgtga aattgttatc cgctcacaat    5460
tccacacaac atacgagccg gaagcataaa gtgtaaagcc tggggtgcct aatgagtgag    5520
ctaactcaca ttaattgcgt tgcgctcact gcccgctttc cagtcgggaa acctgtcgtg    5580
ccagctgcat taatgaatcg gccaacgcgc ggggagaggc ggtttgcgta ttgggcgctc    5640
ttccgcttcc tcgctcactg actcgctgcg ctcggtcgtt cggctgcggc gagcggtatc    5700
agctcactca aaggcggtaa tacggttatc cacagaatca ggggataacg caggaaagaa    5760
catgtgagca aaaggccagc aaaaggccag gaaccgtaaa aaggccgcgt tgctggcgtt    5820
tttccatagg ctccgccccc ctgacgagca tcacaaaaat cgacgctcaa gtcagaggtg    5880
gcgaaacccg acaggactat aaagatacca ggcgtttccc cctggaagct ccctcgtgcg    5940
ctctcctgtt ccgaccctgc cgcttaccgg atacctgtcc gcctttctcc cttcgggaag    6000
cgtggcgctt tctcaatgct cacgctgtag gtatctcagt tcggtgtagg tcgttcgctc    6060
caagctgggc tgtgtgcacg aaccccccgt tcagcccgac cgctgcgcct tatccggtaa    6120
ctatcgtctt gagtccaacc cggtaagaca cgacttatcg ccactggcag cagccactgg    6180
taacaggatt agcagagcga ggtatgtagg cggtgctaca gagttcttga agtggtggcc    6240
taactacggc tacactagaa ggacagtatt tggtatctgc gctctgctga agccagttac    6300
cttcggaaaa agagttggta gctcttgatc cggcaaacaa accaccgctg gtagcggtgg    6360
tttttttgtt tgcaagcagc agattacgcg cagaaaaaaa ggatctcaag aagatccttt    6420
gatcttttct acggggtctg acgctcagtg gaacgaaaac tcacgttaag ggattttggt    6480
catgagatta tcaaaaagga tcttcaccta gatcctttta aattaaaaat gaagttttaa    6540
atcaatctaa agtatatatg agtaaacttg gtctgacagt taccaatgct taatcagtga    6600
ggcacctatc tcagcgatct gtctatttcg ttcatccata gttgcctgac tccccgtcgt    6660
gtagataact acgatacggg agggcttacc atctggcccc agtgctgcaa tgataccgcg    6720
agacccacgc tcaccggctc cagatttatc agcaataaac cagccagccg aagggccga    6780
gcgcagaagt ggtcctgcaa ctttatccgc ctccatccag tctattaatt gttgccggga    6840
agctagagta agtagttcgc cagttaatag tttgcgcaac gttgttgcca ttgctacagg    6900
catcgtggtg tcacgctcgt cgtttggtat ggcttcattc agctccggtt cccaacgatc    6960
aaggcgagtt acatgatccc ccatgttgtg caaaaaagcg gttagctcct tcggtcctcc    7020
gatcgttgtc agaagtaagt tggccgcagt gttatcactc atggttatgg cagcactgca    7080
taattctctt actgtcatgc catccgtaag atgcttttct gtgactggtg agtactcaac    7140
caagtcattc tgagaatagt gtatgcggcg accgagttgc tcttgcccgg cgtcaatacg    7200
ggataatacc gcgccacata gcagaacttt aaaagtgctc atcattggaa aacgttcttc    7260
ggggcgaaaa ctctcaagga tcttaccgct gttgagatcc agttcgatgt aacccactcg    7320
```

| | | |
|---|---|---|
| tgcacccaac tgatcttcag catcttttac tttcaccagc gtttctgggt gagcaaaaac | 7380 | |
| aggaaggcaa aatgccgcaa aaagggaat aagggcgaca cggaaatgtt gaatactcat | 7440 | |
| actcttcctt tttcaatatt attgaagcat ttatcagggt tattgtctca tgagcggata | 7500 | |
| catatttgaa tgtatttaga aaataaaca aatagggggtt ccgcgcacat ttccccgaaa | 7560 | |
| agtgccacct gacgtc | 7576 | |

<210> SEQ ID NO 7
<211> LENGTH: 7561
<212> TYPE: DNA
<213> ORGANISM: Artificial Sequence
<220> FEATURE:
<223> OTHER INFORMATION: Plasmid

<400> SEQUENCE: 7

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctaga | 900 |
| ggtaccggat ctcaccatgg agttggggct gagctgggtt ttcctcgttg ctcttttaag | 960 |
| aggtgtccag tgtcaggagc agctggtgga gtctggggga ggcgtggtcc agcctgggag | 1020 |
| gtccctgaga ctctcctgtg cagcgtctgg attcaccttc agtacctatg catgcactg | 1080 |
| ggtccgccag gctccaggca aggggctgga gtgggtggca gttacatggc atgatggaag | 1140 |
| taataaatac tatgcagact ccgtgaaggg ccgattcacc atctccagag acaactccaa | 1200 |
| gaacacgctg tatctgcaaa tgaacagcct gagagccgag gacacggctg tgtattactg | 1260 |
| tgcgagagga ggagtgggag caacttacta ctactactac ggtatggacg tctggggcca | 1320 |
| agggaccacg gtcaccgtct cctcagcctc caccaagggc ccatcggtct tccccctggc | 1380 |
| accctctagc aagagcacct ctgggggcac agcggccctg ggctgcctgg tcaaggacta | 1440 |
| cttccccgaa ccggtgacgg tgtcgtggaa ctcaggcgcc ctgaccagcg gcgtgcacac | 1500 |
| cttcccggct gtcctacagt cctcaggact ctactccctc agcagcgtgg tgaccgtgcc | 1560 |
| ctccagcagc ttgggcaccc agacctacat ctgcaacgtg aatcacaagc ccagcaacac | 1620 |
| caaggtggac aagagagttg gtgagaggcc agcacaggga gggagggtgt ctgctggaag | 1680 |
| ccaggctcag cgctcctgcc tggacgcatc ccggctatgc agtcccagtc cagggcagca | 1740 |

```
aggcaggccc cgtctgcctc ttcacccgga ggcctctgcc cgccccactc atgctcaggg    1800
agagggtctt ctggctttt ccccaggctc tgggcaggca caggctaggt gcccctaacc    1860
caggccctgc acacaaaggg gcaggtgctg ggctcagacc tgccaagagc catatccggg    1920
aggaccctgc ccctgaccta agcccacccc aaaggccaaa ctctccactc cctcagctcg    1980
gacaccttct ctcctcccag attccagtaa ctcccaatct tctctctgca gagcccaaat    2040
cttgtgacaa aactcacaca tgcccaccgt gcccaggtaa gccagcccag gcctcgccct    2100
ccagctcaag gcgggacagg tgccctagag tagcctgcat ccagggacag gccccagccg    2160
ggtgctgaca cgtccacctc catctcttcc tcagcacctg aactcctggg gggaccgtca    2220
gtcttcctct tccccccaaa acccaaggac accctcatga tctcccggac ccctgaggtc    2280
acatgcgtgg tggtggacgt gagccacgaa gaccctgagg tcaagttcaa ctggtacgtg    2340
gacggcgtgg aggtgcataa tgccaagaca aagccgcggg aggagcagta acagcacg    2400 taccgtgtgg tcagcgtcct caccgtcctg caccaggact ggctgaatgg caaggagtac    2460
aagtgcaagg tctccaacaa agccctccca gcccccatcg agaaaaccat ctccaaagcc    2520
aaaggtggga cccgtggggt gcgagggcca catggacaga ggccggctcg gcccaccctc    2580
tgccctgaga gtgaccgctg taccaacctc tgtccctaca gggcagcccc gagaaccaca    2640
ggtgtacacc ctgcccccat cccgggagga gatgaccaag aaccaggtca gcctgacctg    2700
cctggtcaaa ggcttctatc ccagcgacat cgccgtggag tgggagagca atgggcagcc    2760
ggagaacaac tacaagacca cgcctcccgt gctggactcc gacggctcct tcttcctcta    2820
tagcaagctc accgtggaca agagcaggtg gcagcagggg aacgtcttct catgctccgt    2880
gatgcatgag gctctgcaca accactacac gcagaagagc ctctccctgt ctccgggtaa    2940
atgactcaga tctagagggc ccgtttaaac ccgctgatca gcctcgactg tgccttctag    3000
ttgccagcca tctgttgttt gcccctcccc cgtgccttcc ttgaccctgg aaggtgccac    3060
tcccactgtc ctttcctaat aaaatgagga aattgcatcg cattgtctga gtaggtgtca    3120
ttctattctg ggggtgggg tggggcagga cagcaagggg gaggattggg aagacaatag    3180
caggcatgct ggggatgcgg tgggctctat ggcttctgag gcggaaagaa ccagctgggg    3240
ctctaggggg tatccccacg cgccctgtag cggcgcatta agcgcggcgg gtgtggtggt    3300
tacgcgcagc gtgaccgcta cacttgccag cgccctagcg cccgctcctt tcgctttctt    3360
cccttccttt ctcgccacgt tcgccggctt tccccgtcaa gctctaaatc ggggcatccc    3420
tttagggttc cgatttagtg ctttacggca cctcgacccc aaaaaacttg attagggtga    3480
tggttcacgt agtgggccat cgccctgata gacggttttt cgccctttga cgttggagtc    3540
cacgttcttt aatagtggac tcttgttcca aactggaaca acactcaacc ctatctcggt    3600
ctattctttt gatttataag ggattttggg gatttcggcc tattggttaa aaaatgagct    3660
gatttaacaa aaatttaacg cgaattaatt ctgtggaatg tgtgtcagtt agggtgtgga    3720
aagtccccag gctccccagg caggcagaag tatgcaaagc atgcatctca attagtcagc    3780
aaccaggtgt ggaaagtccc caggctcccc agcaggcaga agtatgcaaa gcatgcatct    3840
caattagtca gcaaccatag tcccgcccct aactccgccc atcccgcccc taactccgcc    3900
cagttccgcc cattctccgc cccatggctg actaattttt tttatttatg cagaggccga    3960
ggccgcctct gcctctgagc tattccagaa gtagtgagga ggcttttttg gaggcctagg    4020
cttttgcaaa aagctcccgg gagcttgtat atccattttc ggatctgatc agcacgtgat    4080
gaaaaagcct gaactcaccg cgacgtctgt cgagaagttt ctgatcgaaa agttcgacag    4140
```

```
cgtctccgac ctgatgcagc tctcggaggg cgaagaatct cgtgctttca gcttcgatgt    4200
aggagggcgt ggatatgtcc tgcgggtaaa tagctgcgcc gatggtttct acaaagatcg    4260
ttatgtttat cggcactttg catcggccgc gctcccgatt ccggaagtgc ttgacattgg    4320
ggaattcagc gagagcctga cctattgcat ctcccgccgt gcacagggtg tcacgttgca    4380
agacctgcct gaaaccgaac tgcccgctgt tctgcagccg gtcgcggagg ccatggatgc    4440
gatcgctgcg gccgatctta gccagacgag cgggttcggc ccattcggac cgcaaggaat    4500
cggtcaatac actacatggc gtgatttcat atgcgcgatt gctgatcccc atgtgtatca    4560
ctggcaaact gtgatggacg acaccgtcag tgcgtccgtc gcgcaggctc tcgatgagct    4620
gatgctttgg gccgaggact gccccgaagt ccggcacctc gtgcacgcgg atttcggctc    4680
caacaatgtc ctgacggaca atggccgcat aacagcggtc attgactgga gcgaggcgat    4740
gttcggggat tcccaatacg aggtcgccaa catcttcttc tggaggccgt ggttggcttg    4800
tatggagcag cagacgcgct acttcgagcg gaggcatccg gagcttgcag gatcgccgcg    4860
gctccgggcg tatatgctcc gcattggtct tgaccaactc tatcagagct tggttgacgg    4920
caatttcgat gatgcagctt gggcgcaggg tcgatgcgac gcaatcgtcc gatccggagc    4980
cgggactgtc gggcgtacac aaatcgcccg cagaagcgcg gccgtctgga ccgatggctg    5040
tgtagaagta ctcgccgata gtggaaaccg acgcccagc actcgtccga gggcaaagga    5100
atagcacgtg ctacgagatt tcgattccac cgccgccttc tatgaaaggt tgggcttcgg    5160
aatcgttttc cggacgccg gctggatgat cctccagcgc ggggatctca tgctggagtt    5220
cttcgcccac cccaacttgt ttattgcagc ttataatggt tacaaataaa gcaatagcat    5280
cacaaatttc acaaataaag catttttttc actgcattct agttgtggtt tgtccaaact    5340
catcaatgta tcttatcatg tctgtatacc gtcgacctct agctagagct tggcgtaatc    5400
atggtcatag ctgtttcctg tgtgaaattg ttatccgctc acaattccac acaacatacg    5460
agccggaagc ataaagtgta aagcctgggg tgcctaatga gtgagctaac tcacattaat    5520
tgcgttgcgc tcactgcccg ctttccagtc gggaaacctg tcgtgccagc tgcattaatg    5580
aatcggccaa cgcgcgggga gaggcggttt gcgtattggg cgctcttccg cttcctcgct    5640
cactgactcg ctgcgctcgg tcgttcggct gcggcgagcg gtatcagctc actcaaaggc    5700
ggtaatacgg ttatccacag aatcagggga taacgcagga agaacatgt gagcaaaagg    5760 ccagcaaaag gccaggaacc gtaaaaaggc cgcgttgctg gcgttttttcc ataggctccg    5820 cccccctgac gagcatcaca aaaatcgacg ctcaagtcag aggtggcgaa acccgacagg    5880
actataaaga taccaggcgt ttccccctgg aagctccctc gtgcgctctc ctgttccgac    5940
cctgccgctt accggatacc tgtccgcctt tctcccttcg ggaagcgtgg cgctttctca    6000
atgctcacgc tgtaggtatc tcagttcggt gtaggtcgtt cgctccaagc tgggctgtgt    6060
gcacgaaccc cccgttcagc ccgaccgctg cgccttatcc ggtaactatc gtcttgagtc    6120
caacccggta agacacgact tatcgccact ggcagcagcc actggtaaca ggattagcag    6180
agcgaggtat gtaggcggtg ctacagagtt cttgaagtgg tggcctaact acggctacac    6240
tagaaggaca gtatttggta tctgcgctct gctgaagcca gttaccttcg gaaaaagagt    6300
tggtagctct tgatccggca aacaaaccac cgctggtagc ggtggttttt tgtttgcaa    6360 gcagcagatt acgcgcagaa aaaaggatc tcaagaagat cctttgatct tttctacggg    6420
gtctgacgct cagtggaacg aaaactcacg ttaagggatt ttggtcatga gattatcaaa    6480
```

| aaggatcttc | acctagatcc | ttttaaatta | aaaatgaagt | tttaaatcaa | tctaaagtat | 6540 |
| atatgagtaa | acttggtctg | acagttacca | atgcttaatc | agtgaggcac | ctatctcagc | 6600 |
| gatctgtcta | tttcgttcat | ccatagttgc | ctgactcccc | gtcgtgtaga | taactacgat | 6660 |
| acgggagggc | ttaccatctg | gccccagtgc | tgcaatgata | ccgcgagacc | cacgctcacc | 6720 |
| ggctccagat | ttatcagcaa | taaaccagcc | agccggaagg | gccgagcgca | gaagtggtcc | 6780 |
| tgcaacttta | tccgcctcca | tccagtctat | taattgttgc | cgggaagcta | gagtaagtag | 6840 |
| ttcgccagtt | aatagtttgc | gcaacgttgt | tgccattgct | acaggcatcg | tggtgtcacg | 6900 |
| ctcgtcgttt | ggtatggctt | cattcagctc | cggttcccaa | cgatcaaggc | gagttacatg | 6960 |
| atcccccatg | ttgtgcaaaa | aagcggttag | ctccttcggt | cctccgatcg | ttgtcagaag | 7020 |
| taagttggcc | gcagtgttat | cactcatggt | tatggcagca | ctgcataatt | ctcttactgt | 7080 |
| catgccatcc | gtaagatgct | tttctgtgac | tggtgagtac | tcaaccaagt | cattctgaga | 7140 |
| atagtgtatg | cggcgaccga | gttgctcttg | cccggcgtca | atacgggata | ataccgcgcc | 7200 |
| acatagcaga | actttaaaag | tgctcatcat | tggaaaacgt | tcttcggggc | gaaaactctc | 7260 |
| aaggatctta | ccgctgttga | gatccagttc | gatgtaaccc | actcgtgcac | ccaactgatc | 7320 |
| ttcagcatct | tttactttca | ccagcgtttc | tgggtgagca | aaaacaggaa | ggcaaaatgc | 7380 |
| cgcaaaaaag | ggaataaggg | cgacacggaa | atgttgaata | ctcatactct | tcctttttca | 7440 |
| atattattga | agcatttatc | agggttattg | tctcatgagc | ggatacatat | ttgaatgtat | 7500 |
| ttagaaaaat | aaacaaatag | gggttccgcg | cacatttccc | cgaaaagtgc | cacctgacgt | 7560 |
| c | | | | | | 7561 |

<210> SEQ ID NO 8
<211> LENGTH: 6082
<212> TYPE: DNA
<213> ORGANISM: Artificial Sequence
<220> FEATURE:
<223> OTHER INFORMATION: Plasmid

<400> SEQUENCE: 8

| gacggatcgg | gagatctccc | gatccctat | ggtcgactct | cagtacaatc | tgctctgatg | 60 |
| ccgcatagtt | aagccagtat | ctgctccctg | cttgtgtgtt | ggaggtcgct | gagtagtgcg | 120 |
| cgagcaaaat | ttaagctaca | acaaggcaag | gcttgaccga | caattgcatg | aagaatctgc | 180 |
| ttagggttag | gcgttttgcg | ctgcttcgcg | atgtacgggc | cagatatacg | cgttgacatt | 240 |
| gattattgac | tagttattaa | tagtaatcaa | ttacggggtc | attagttcat | agcccatata | 300 |
| tggagttccg | cgttacataa | cttacggtaa | atggcccgcc | tggctgaccg | cccaacgacc | 360 |
| cccgcccatt | gacgtcaata | atgacgtatg | ttcccatagt | aacgccaata | gggactttcc | 420 |
| attgacgtca | atgggtggac | tatttacggt | aaactgccca | cttggcagta | catcaagtgt | 480 |
| atcatatgcc | aagtacgccc | cctattgacg | tcaatgacgg | taaatggccc | gcctggcatt | 540 |
| atgcccagta | catgacctta | tgggactttc | ctacttggca | gtacatctac | gtattagtca | 600 |
| tcgctattac | catggtgatg | cggttttggc | agtacatcaa | tgggcgtgga | tagcggtttg | 660 |
| actcacgggg | atttccaagt | ctccacccca | ttgacgtcaa | tgggagtttg | ttttggcacc | 720 |
| aaaatcaacg | ggactttcca | aaatgtcgta | acaactccgc | cccattgacg | caaatgggcg | 780 |
| gtaggcgtgt | acggtgggag | gtctatataa | gcagagctct | ctggctaact | agagaaccca | 840 |
| ctgcttactg | gcttatcgaa | attaatacga | ctcactatag | ggagacccaa | gctggctaga | 900 |
| aagcttggat | ctcaccatga | gggtccctgc | tcagctcctg | ggactcctgc | tgctctggct | 960 |

```
cccagatacc agatgtgaca tccagatgac ccagtctcca tcctccctgt ctgcatctgt    1020
aggagacaga gtcaccatca cttgccgggc gagtcagggc attagcaatt atttagcctg    1080
gtatcagcag aaaacaggga aagttcctaa gttcctgatc tatgaagcat ccactttgca    1140 atcagggtc ccatctcggt tcagtggcgg tggatctggg acagatttca ctctcaccat     1200
cagcagcctg cagcctgaag atgttgcaac ttattactgt caaaattata cagtgcccc    1260 attcactttc ggccctggga ccaaagtgga tatcaaacga actgtggctg cacccctgt    1320 cttcatcttc ccgccatctg atgagcagtt gaaatctgga actgctagcg ttgtgtgcct    1380
gctgaataac ttctatccca gagaggccaa agtacagtgg aaggtggata cgcccccca    1440 atcgggtaac tcccaggaga gtgtcacaga gcaggacagc aaggacagca cctacagcct    1500
cagcagcacc ctgacgctga gcaaagcaga ctacgagaaa cacaaagtct acgcctgcga    1560
agtcacccat cagggcctga gctcgcccgt cacaaagagc ttcaacaggg gagagtgtta    1620
ggaattcgcg gccgctcgag tctagagggc ccgtttaaac ccgctgatca gcctcgactg    1680
tgccttctag ttgccagcca tctgttgttt gcccctcccc cgtgccttcc ttgaccctgg    1740
aaggtgccac tcccactgtc ctttcctaat aaaatgagga aattgcatcg cattgtctga    1800
gtaggtgtca ttctattctg ggggtgggg tgggcagga cagcaagggg gaggattggg     1860
aagacaatag caggcatgct ggggatgcgg tgggctctat ggcttctgag gcggaaagaa    1920
ccagctgggg ctctaggggg tatccccacg cgccctgtag cggcgcatta agcgcggcgg    1980
gtgtggtggt tacgcgcagc gtgaccgcta cacttgccag cgccctagcg cccgctcctt    2040
tcgctttctt cccttccttt ctcgccacgt tcgccggctt tccccgtcaa gctctaaatc    2100
ggggcatccc tttagggttc cgatttagtg ctttacggca cctcgacccc aaaaaacttg    2160
attagggtga tggttcacgt agtgggccat cgccctgata cggttttt cgcccttga      2220 cgttggagtc cacgttcttt aatagtggac tcttgttcca aactggaaca cactcaacc     2280 ctatctcggt ctattctttt gatttataag ggattttggg gatttcggcc tattggttaa    2340
aaaatgagct gatttaacaa aaatttaacg cgaattaatt ctgtggaatg tgtgtcagtt    2400
agggtgtgga aagtccccag gctccccagg caggcagaag tatgcaaagc atgcatctca    2460
attagtcagc aaccaggtgt ggaaagtccc caggctcccc agcaggcaga agtatgcaaa    2520
gcatgcatct caattagtca gcaaccatag tcccgcccct aactccgccc atcccgcccc    2580
taactccgcc cagttccgcc cattctccgc cccatggctg actaatttt tttatttatg     2640 cagaggccga ggccgcctct gcctctgagc tattccagaa gtagtgagga ggcttttttg    2700
gaggcctagg cttttgcaaa aagctcccgg gagcttgtat atccattttc ggatctgatc    2760
aagagacagg atgaggatcg tttcgcatga ttgaacaaga tggattgcac gcaggttctc    2820
cggccgcttg ggtggagagg ctattcggct atgactgggc acaacagaca atcggctgct    2880
ctgatgccgc cgtgttccgg ctgtcagcgc aggggcgccc ggttcttttt gtcaagaccg    2940
acctgtccgg tgccctgaat gaactgcagg acgaggcagc gcggctatcg tggctggcca    3000
cgacgggcgt tccttgcgca gctgtgctcg acgttgtcac tgaagcggga agggactggc    3060
tgctattggg cgaagtgccg gggcaggatc tcctgtcatc tcaccttgct cctgccgaga    3120
aagtatccat catggctgat gcaatgcggc ggctgcatac gcttgatccg gctacctgcc    3180
cattcgacca ccaagcgaaa catcgcatcg agcgagcacg tactcggatg gaagccggtc    3240
ttgtcgatca ggatgatctg gacgaagagc atcagggget cgcgccagcc gaactgttcg    3300
```

```
ccaggctcaa ggcgcgcatg cccgacggcg aggatctcgt cgtgacccat ggcgatgcct    3360
gcttgccgaa tatcatggtg gaaaatggcc gcttttctgg attcatcgac tgtggccggc    3420
tgggtgtggc ggaccgctat caggacatag cgttggctac ccgtgatatt gctgaagagc    3480
ttggcggcga atgggctgac cgcttcctcg tgctttacgg tatcgccgct cccgattcgc    3540
agcgcatcgc cttctatcgc cttcttgacg agttcttctg agcgggactc tggggttcga    3600
aatgaccgac caagcgacgc ccaacctgcc atcacgagat ttcgattcca ccgccgcctt    3660
ctatgaaagg ttgggcttcg gaatcgtttt ccgggacgcc ggctggatga tcctccagcg    3720
cggggatctc atgctggagt tcttcgccca ccccaacttg tttattgcag cttataatgg    3780
ttacaaataa agcaatagca tcacaaattt cacaaataaa gcattttttt cactgcattc    3840
tagttgtggt ttgtccaaac tcatcaatgt atcttatcat gtctgtatac cgtcgacctc    3900
tagctagagc ttggcgtaat catggtcata gctgtttcct gtgtgaaatt gttatccgct    3960
cacaattcca cacaacatac gagccggaag cataaagtgt aaagcctggg gtgcctaatg    4020
agtgagctaa ctcacattaa ttgcgttgcg ctcactgccc gctttccagt cgggaaacct    4080
gtcgtgccag ctgcattaat gaatcggcca acgcgcgggg agaggcggtt tgcgtattgg    4140
gcgctcttcc gcttcctcgc tcactgactc gctgcgctcg tcgttcggc tgcggcgagc    4200 ggtatcagct cactcaaagg cggtaatacg gttatccaca gaatcagggg ataacgcagg    4260
aaagaacatg tgagcaaaag gccagcaaaa ggccaggaac cgtaaaaagg ccgcgttgct    4320
ggcgtttttc cataggctcc gcccccctga cgagcatcac aaaaatcgac gctcaagtca    4380
gaggtggcga aacccgacag gactataaag ataccaggcg tttccccctg gaagctccct    4440
cgtgcgctct cctgttccga ccctgccgct taccggatac ctgtccgcct ttctcccttc    4500
gggaagcgtg gcgctttctc aatgctcacg ctgtaggtat ctcagttcgg tgtaggtcgt    4560
tcgctccaag ctgggctgtg tgcacgaacc ccccgttcag cccgaccgct gcgccttatc    4620
cggtaactat cgtcttgagt ccaacccggt aagacacgac ttatcgccac tggcagcagc    4680
cactggtaac aggattagca gagcgaggta tgtaggcggt gctacagagt tcttgaagtg    4740
gtggcctaac tacggctaca ctagaaggac agtatttggt atctgcgctc tgctgaagcc    4800
agttaccttc ggaaaaagag ttggtagctc ttgatccggc aaacaaacca ccgctggtag    4860
cggtggtttt tttgtttgca agcagcagat tacgcgcaga aaaaaaggat ctcaagaaga    4920
tcctttgatc ttttctacgg ggtctgacgc tcagtggaac gaaaactcac gttaagggat    4980
tttggtcatg agattatcaa aaaggatctt cacctagatc cttttaaatt aaaaatgaag    5040
ttttaaatca atctaaagta tatatgagta aacttggtct gacagttacc aatgcttaat    5100
cagtgaggca cctatctcag cgatctgtct atttcgttca tccatagttg cctgactccc    5160
cgtcgtgtag ataactacga tacgggaggg cttaccatct ggccccagtg ctgcaatgat    5220
accgcgagac ccacgctcac cggctccaga tttatcagca ataaaccagc cagccggaag    5280
ggccgagcgc agaagtggtc ctgcaacttt atccgcctcc atccagtcta ttaattgttg    5340
ccgggaagct agagtaagta gttcgccagt taatagtttg cgcaacgttg ttgccattgc    5400
tacaggcatc gtggtgtcac gctcgtcgtt tggtatggct tcattcagct ccggttccca    5460
acgatcaagg cgagttacat gatcccccat gttgtgcaaa aaagcggtta gctccttcgg    5520
tcctccgatc gttgtcagaa gtaagttggc cgcagtgtta tcactcatgg ttatggcagc    5580
actgcataat tctcttactg tcatgccatc cgtaagatgc ttttctgtga ctggtgagta    5640
ctcaaccaag tcattctgag aatagtgtat gcggcgaccg agttgctctt gcccggcgtc    5700
```

```
aatacgggat aataccgcgc cacatagcag aactttaaaa gtgctcatca ttggaaaacg    5760
ttcttcgggg cgaaaactct caaggatctt accgctgttg agatccagtt cgatgtaacc    5820
cactcgtgca cccaactgat cttcagcatc ttttactttc accagcgttt ctgggtgagc    5880
aaaaacagga aggcaaaatg ccgcaaaaaa gggaataagg gcgacacgga aatgttgaat    5940
actcatactc ttcctttttc aatattattg aagcatttat cagggttatt gtctcatgag    6000
cggatacata tttgaatgta tttagaaaaa taaacaaata ggggttccgc gcacatttcc    6060
ccgaaaagtg ccacctgacg tc                                            6082
```

<210> SEQ ID NO 9  
<211> LENGTH: 6082  
<212> TYPE: DNA  
<213> ORGANISM: Artificial Sequence  
<220> FEATURE:  
<223> OTHER INFORMATION: Plasmid

<400> SEQUENCE: 9

```
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aatgtcgta acaactccgc cccattgacg caaatgggcg      780
gtaggcgtgt acggtgggag gtctatataa gcagagctct ctggctaact agagaaccca     840
ctgcttactg gcttatcgaa attaatacga ctcactatag ggagacccaa gctggctaga     900
aagcttggat ctcaccatga gggtccccgc tcagctcctg gggctcctgc tgctctgttt     960
cccaggtgcc agatgtgaca tccagatgac ccagtctcca tcctcactgt ctgcatctgt    1020
aggagacaga gtcaccatca cttgtcgggc gagtcagggc attaccaatt atttagcctg    1080
gtttcagcag aaaccaggga aagccctaa gtcccttatc tatgctgcat ccagtttgca     1140
aagtggggtc ccatcaaagt tcagcggcag tggatctggg acagatttca gtctcaccat    1200
cagcagcctg cagcctgaag attttgcaac ttattactgc caacagtata atagttaccc    1260
gatcaccttc ggccaaggga cacgactgga gattaaacga actgtggctg caccatctgt    1320
cttcatcttc ccgccatctg atgagcagtt gaaatctgga actgctagcg ttgtgtgcct    1380
gctgaataac ttctatccca gagaggccaa agtacagtgg aaggtggata cgcccctcca    1440
atcgggtaac tcccaggaga gtgtcacaga gcaggacagc aaggacagca cctacagcct    1500
cagcagcacc ctgacgctga gcaaagcaga ctacgagaaa cacaaagtct acgcctgcga    1560
agtcacccat cagggcctga gctcgcccgt cacaaagagc ttcaacaggg gagagtgtta    1620
```

-continued

```
ggaattcgcg gccgctcgag tctagagggc ccgtttaaac ccgctgatca gcctcgactg    1680
tgccttctag ttgccagcca tctgttgttt gcccctcccc cgtgccttcc ttgaccctgg    1740
aaggtgccac tcccactgtc ctttcctaat aaaatgagga aattgcatcg cattgtctga    1800
gtaggtgtca ttctattctg ggggtgggg tggggcagga cagcaagggg gaggattggg     1860
aagacaatag caggcatgct ggggatgcgg tgggctctat ggcttctgag gcggaaagaa    1920
ccagctgggg ctctagggggg tatcccacg cgccctgtag cggcgcatta gcgcggcgg     1980 gtgtggtggt tacgcgcagc gtgaccgcta cacttgccag cgccctagcg cccgctcctt    2040
tcgctttctt cccttccttt ctcgccacgt tcgccggctt tccccgtcaa gctctaaatc    2100
ggggcatccc tttagggttc cgatttagtg ctttacggca cctcgacccc aaaaaacttg    2160
attagggtga tggttcacgt agtgggccat cgccctgata cggttttttt cgcccttga    2220 cgttggagtc cacgttcttt aatagtggac tcttgttcca actggaaca cactcaacc     2280 ctatctcggt ctattctttt gatttataag gattttggg gattcgcc tattggttaa      2340 aaaatgagct gatttaacaa aaatttaacg cgaattaatt ctgtggaatg tgtgtcagtt   2400
agggtgtgga aagtccccag gctccccagg caggcagaag tatgcaaagc atgcatctca    2460
attagtcagc aaccaggtgt ggaaagtccc caggctcccc agcaggcaga agtatgcaaa    2520
gcatgcatct caattagtca gcaaccatag tcccgcccct aactccgccc atcccgcccc    2580
taactccgcc cagttccgcc cattctccgc cccatggctg actaatttt tttatttatg    2640 cagaggccga ggccgcctct gcctctgagc tattccagaa gtagtgagga ggcttttttg    2700
gaggcctagg cttttgcaaa aagctcccgg gagcttgtat atccattttc ggatctgatc    2760
aagagacagg atgaggatcg tttcgcatga ttgaacaaga tggattgcac gcaggttctc    2820
cggccgcttg ggtggagagg ctattcggct atgactgggc acaacagaca atcggctgct    2880
ctgatgccgc cgtgttccgg ctgtcagcgc agggcgcc ggttcttttt gtcaagaccg     2940
acctgtccgg tgccctgaat gaactgcagg acgaggcagc gcggctatcg tggctggcca    3000
cgacgggcgt tccttgcgca gctgtgctcg acgttgtcac tgaagcggga agggactggc    3060
tgctattggg cgaagtgccg gggcaggatc tcctgtcatc tcaccttgct cctgccgaga    3120
aagtatccat catggctgat gcaatgcggc ggctgcatac gcttgatccg gctacctgcc    3180
cattcgacca ccaagcgaaa catcgcatcg agcgagcacg tactcggatg aagccggtc     3240 ttgtcgatca ggatgatctg gacgaagagc atcaggggct cgcgccagcc gaactgttcg    3300
ccaggctcaa ggcgcgcatg cccgacgcg aggatctcgt cgtgacccat ggcgatgcct     3360
gcttgccgaa tatcatggtg gaaaatggcc gcttttctgg attcatcgac tgtggccggc    3420
tgggtgtggc ggaccgctat caggacatag cgttggctac ccgtgatatt gctgaagagc    3480
ttggcggcga atgggctgac cgcttcctcg tgctttacgg tatcgccgct cccgattcgc    3540
agcgcatcgc cttctatcgc cttcttgacg agttcttctg agcggactc tggggttcga    3600 aatgaccgac caagcgacgc ccaacctgcc atcacgagat ttcgattcca ccgccgcctt    3660
ctatgaaagg ttgggcttcg gaatcgtttt ccgggacgcc ggctggatga tcctccagcg    3720
cggggatctc atgctggagt tcttcgccca ccccaacttg tttattgcag cttataatgg    3780
ttacaaataa agcaatagca tcacaaattt cacaaataaa gcatttttt cactgcattc     3840 tagttgtggt ttgtccaaac tcatcaatgt atcttatcat gtctgtatac cgtcgacctc    3900
tagctagagc ttggcgtaat catggtcata gctgtttcct gtgtgaaatt gttatccgct    3960
cacaattcca cacaacatac gagccggaag cataaagtgt aaagcctggg gtgcctaatg    4020
```

```
agtgagctaa ctcacattaa ttgcgttgcg ctcactgccc gctttccagt cgggaaacct    4080
gtcgtgccag ctgcattaat gaatcggcca acgcgcgggg agaggcggtt tgcgtattgg    4140
gcgctcttcc gcttcctcgc tcactgactc gctgcgctcg gtcgttcggc tgcggcgagc    4200
ggtatcagct cactcaaagg cggtaatacg gttatccaca gaatcagggg ataacgcagg    4260
aaagaacatg tgagcaaaag gccagcaaaa ggccaggaac cgtaaaaagg ccgcgttgct    4320
ggcgtttttc cataggctcc gcccccctga cgagcatcac aaaaatcgac gctcaagtca    4380
gaggtggcga aacccgacag gactataaag ataccaggcg tttccccctg gaagctccct    4440
cgtgcgctct cctgttccga ccctgccgct taccggatac ctgtccgcct ttctcccttc    4500
gggaagcgtg gcgctttctc aatgctcacg ctgtaggtat ctcagttcgg tgtaggtcgt    4560
tcgctccaag ctgggctgtg tgcacgaacc ccccgttcag cccgaccgct gcgccttatc    4620
cggtaactat cgtcttgagt ccaacccggt aagacacgac ttatcgccac tggcagcagc    4680
cactggtaac aggattagca gagcgaggta tgtaggcggt gctacagagt tcttgaagtg    4740
gtggcctaac tacggctaca ctagaaggac agtatttggt atctgcgctc tgctgaagcc    4800
agttaccttc ggaaaaagag ttggtagctc ttgatccggc aaacaaacca ccgctggtag    4860
cggtggtttt tttgtttgca agcagcagat tacgcgcaga aaaaaggat ctcaagaaga    4920 tcctttgatc ttttctacgg ggtctgacgc tcagtggaac gaaaactcac gttaagggat    4980
tttggtcatg agattatcaa aaaggatctt cacctagatc cttttaaatt aaaaatgaag    5040
ttttaaatca atctaaagta tatatgagta aacttggtct gacagttacc aatgcttaat    5100
cagtgaggca cctatctcag cgatctgtct atttcgttca tccatagttg cctgactccc    5160
cgtcgtgtag ataactacga tacgggaggg cttaccatct ggccccagtg ctgcaatgat    5220
accgcgagac ccacgctcac cggctccaga tttatcagca ataaaccagc cagccggaag    5280
ggccgagcgc agaagtggtc ctgcaacttt atccgcctcc atccagtcta ttaattgttg    5340
ccgggaagct agagtaagta gttcgccagt taatagtttg cgcaacgttg ttgccattgc    5400
tacaggcatc gtggtgtcac gctcgtcgtt tggtatggct tcattcagct ccggttccca    5460
acgatcaagg cgagttacat gatccccat gttgtgcaaa aaagcggtta gctccttcgg    5520
tcctccgatc gttgtcagaa gtaagttggc cgcagtgtta tcactcatgg ttatggcagc    5580
actgcataat tctcttactg tcatgccatc cgtaagatgc ttttctgtga ctggtgagta    5640
ctcaaccaag tcattctgag aatagtgtat gcggcgaccg agttgctctt gcccggcgtc    5700
aatacgggat aataccgcgc cacatagcag aactttaaaa gtgctcatca ttggaaaacg    5760
ttcttcgggg cgaaaactct caaggatctt accgctgttg agatccagtt cgatgtaacc    5820
cactcgtgca cccaactgat cttcagcatc ttttactttc accagcgttt ctgggtgagc    5880
aaaaacagga aggcaaaatg ccgcaaaaaa gggaataagg gcgacacgga aatgttgaat    5940
actcatactc ttcctttttc aatattattg aagcatttat cagggttatt gtctcatgag    6000
cggatacata tttgaatgta tttagaaaaa taaacaaata ggggttccgc gcacatttcc    6060
ccgaaaagtg ccacctgacg tc                                            6082

<210> SEQ ID NO 10
<211> LENGTH: 6082
<212> TYPE: DNA
<213> ORGANISM: Artificial Sequence
<220> FEATURE:
<223> OTHER INFORMATION: Plasmid
```

<400> SEQUENCE: 10

```
gacggatcgg gagatctccc gatccctat  ggtcgactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggac tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgc ccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctaga   900
aagcttggat ctcaccatga gggtccctgc tcagctcctg ggctcctgc tgctctgttt    960
cccaggtgcc agatgtgaca tccagatgac ccagtctcca tcctcactgt ctgcatctgt  1020
aggagacaga gtcaccatca cttgtcgggc gagtcagggc attagccatt atttagcctg  1080
gtttcagcag aaaccaggga agcccctaa gtccctgatc tatgctgcat ccagtttgca  1140
aagtggggtc ccatcaaagt tcagcggcag tggatctggg acagatttca ctctcaccat  1200
cagcagccta cagcctgaag attttgcaac ttattactgc aacagtata atagtttccc  1260
gctcactttc ggcggaggga ccaaggtgga gatcaaacga actgtggctg caccatctgt  1320
cttcatcttc ccgccatctg atgagcagtt gaaatctgga actgctagcg ttgtgtgcct  1380
gctgaataac ttctatccca gagaggccaa agtacagtgg aaggtggata acgcctcca  1440
atcgggtaac tcccaggaga gtgtcacaga gcaggacagc aaggacagca cctacagcct  1500
cagcagcacc ctgacgctga gcaaagcaga ctacgagaaa cacaaagtct acgcctgcga  1560
agtcacccat caggctgga gctcgcccgt cacaaagagc ttcaacaggg gagagtgtta  1620
ggaattcgcg gccgctcgag tctagagggc ccgtttaaac ccgctgatca gcctcgactg  1680
tgccttctag ttgccagcca tctgttgttt gcccctcccc cgtgccttcc ttgaccctgg  1740
aaggtgccac tcccactgtc ctttcctaat aaaatgagga aattgcatcg cattgtctga  1800
gtaggtgtca ttctattctg ggggggtggg tggggcagga cagcaagggg gaggattggg  1860
aagacaatag caggcatgct ggggatgcgg tgggctctat ggcttctgag gcggaaagaa  1920
ccagctgggg ctctagggg tatcccacg cgccctgtag cggcgcatta agcgcggcgg  1980
gtgtggtggt tacgcgcagc gtgaccgcta cacttgccag cgccctagcg cccgctcctt  2040
tcgctttctt cccttccttt ctcgccacgt tcgccggctt tccccgtcaa gctctaaatc  2100
gggggcatccc tttagggttc cgatttagtg ctttacggca cctcgacccc aaaaaacttg  2160
attagggtga tggttcacgt agtgggccat cgccctgata gacggttttt cgccctttga  2220
cgttggagtc cacgttcttt aatagtggac tcttgttcca aactggaaca acactcaacc  2280
ctatctcggt ctattctttt gatttataag ggattttggg gatttcggcc tattggttaa  2340
```

```
aaaatgagct gatttaacaa aaatttaacg cgaattaatt ctgtggaatg tgtgtcagtt    2400
agggtgtgga aagtccccag gctcccagg caggcagaag tatgcaaagc atgcatctca    2460
attagtcagc aaccaggtgt ggaaagtccc caggctcccc agcaggcaga agtatgcaaa    2520
gcatgcatct caattagtca gcaaccatag tcccgcccct aactccgccc atcccgcccc    2580
taactccgcc cagttccgcc cattctccgc cccatggctg actaattttt tttatttatg    2640
cagaggccga ggccgcctct gcctctgagc tattccagaa gtagtgagga ggcttttttg    2700
gaggcctagg cttttgcaaa aagctcccgg gagcttgtat atccattttc ggatctgatc    2760
aagagacagg atgaggatcg tttcgcatga ttgaacaaga tggattgcac gcaggttctc    2820
cggccgcttg ggtggagagg ctattcggct atgactgggc acaacagaca atcggctgct    2880
ctgatgccgc cgtgttccgg ctgtcagcgc aggggcgccc ggttcttttt gtcaagaccg    2940
acctgtccgg tgccctgaat gaactgcagg acgaggcagc gcggctatcg tggctggcca    3000
cgacgggcgt tccttgcgca gctgtgctcg acgttgtcac tgaagcggga agggactggc    3060
tgctattggg cgaagtgccg gggcaggatc tcctgtcatc tcaccttgct cctgccgaga    3120
aagtatccat catggctgat gcaatgcggc ggctgcatac gcttgatccg gctacctgcc    3180
cattcgacca ccaagcgaaa catcgcatcg agcgagcacg tactcggatg aagccggtc    3240 ttgtcgatca ggatgatctg gacgaagagc atcaggggct cgcgccagcc gaactgttcg    3300
ccaggctcaa ggcgcgcatg cccgacggcg aggatctcgt cgtgacccat ggcgatgcct    3360
gcttgccgaa tatcatggtg gaaaatggcc gcttttctgg attcatcgac tgtggccggc    3420
tgggtgtggc ggaccgctat caggacatag cgttggctac ccgtgatatt gctgaagagc    3480
ttggcggcga atgggctgac cgcttcctcg tgctttacgg tatcgccgct cccgattcgc    3540
agcgcatcgc cttctatcgc cttcttgacg agttcttctg agcgggactc tggggttcga    3600
aatgaccgac caagcgacgc ccaacctgcc atcacgagat ttcgattcca ccgccgcctt    3660
ctatgaaagg ttgggcttcg gaatcgtttt ccggacgcc ggctggatga tcctccagcg    3720
cggggatctc atgctggagt tcttcgccca ccccaacttg tttattgcag cttataatgg    3780
ttacaaataa agcaatagca tcacaaattt cacaaataaa gcatttttt cactgcattc    3840 tagttgtggt ttgtccaaac tcatcaatgt atcttatcat gtctgtatac cgtcgacctc    3900
tagctagagc ttggcgtaat catggtcata gctgtttcct gtgtgaaatt gttatccgct    3960
cacaattcca cacaacatac gagccggaag cataaagtgt aaagcctggg gtgcctaatg    4020
agtgagctaa ctcacattaa ttgcgttgcg ctcactgccc gctttccagt cgggaaacct    4080
gtcgtgccag ctgcattaat gaatcggcca acgcgcgggg agaggcggtt tgcgtattgg    4140
gcgctcttcc gcttcctcgc tcactgactc gctgcgctcg tcgttcggc tgcggcgagc    4200 ggtatcagct cactcaaagg cggtaatacg gttatccaca gaatcagggg ataacgcagg    4260
aaagaacatg tgagcaaaag gccagcaaaa ggccaggaac cgtaaaaagg ccgcgttgct    4320
ggcgtttttc cataggctcc gcccccctga cgagcatcac aaaaatcgac gctcaagtca    4380
gaggtggcga aacccgacag gactataaag ataccaggcg tttccccctg gaagctccct    4440
cgtgcgctct cctgttccga ccctgccgct taccggatac ctgtccgcct ttctcccttc    4500
gggaagcgtg gcgctttctc aatgctcacg ctgtaggtat ctcagttcgg tgtaggtcgt    4560
tcgctccaag ctgggctgtg tgcacgaacc ccccgttcag cccgaccgct gcgccttatc    4620
cggtaactat cgtcttgagt ccaacccggt aagacacgac ttatcgccac tggcagcagc    4680
```

```
cactggtaac aggattagca gagcgaggta tgtaggcggt gctacagagt tcttgaagtg    4740
gtggcctaac tacggctaca ctagaaggac agtatttggt atctgcgctc tgctgaagcc    4800
agttaccttc ggaaaaagag ttggtagctc ttgatccggc aaacaaacca ccgctggtag    4860
cggtggtttt tttgtttgca agcagcagat tacgcgcaga aaaaaaggat ctcaagaaga    4920
tcctttgatc ttttctacgg ggtctgacgc tcagtggaac gaaaactcac gttaagggat    4980
tttggtcatg agattatcaa aaaggatctt cacctagatc cttttaaatt aaaaatgaag    5040
ttttaaatca atctaaagta tatatgagta aacttggtct gacagttacc aatgcttaat    5100
cagtgaggca cctatctcag cgatctgtct atttcgttca tccatagttg cctgactccc    5160
cgtcgtgtag ataactacga tacgggaggg cttaccatct ggccccagtg ctgcaatgat    5220
accgcgagac ccacgctcac cggctccaga tttatcagca ataaaccagc cagccggaag    5280
ggccgagcgc agaagtggtc ctgcaacttt atccgcctcc atccagtcta ttaattgttg    5340
ccgggaagct agagtaagta gttcgccagt taatagtttg cgcaacgttg ttgccattgc    5400
tacaggcatc gtggtgtcac gctcgtcgtt tggtatggct tcattcagct ccggttccca    5460
acgatcaagg cgagttacat gatccccat gttgtgcaaa aaagcggtta gctccttcgg    5520
tcctccgatc gttgtcagaa gtaagttggc cgcagtgtta tcactcatgg ttatggcagc    5580
actgcataat tctcttactg tcatgccatc cgtaagatgc ttttctgtga ctggtgagta    5640
ctcaaccaag tcattctgag aatagtgtat gcggcgaccg agttgctctt gcccggcgtc    5700
aatacgggat aataccgcgc cacatagcag aactttaaaa gtgctcatca ttggaaaacg    5760
ttcttcgggg cgaaaactct caaggatctt accgctgttg agatccagtt cgatgtaacc    5820
cactcgtgca cccaactgat cttcagcatc ttttactttc accagcgttt ctgggtgagc    5880
aaaaacagga aggcaaaatg ccgcaaaaaa gggaataagg gcgacacgga aatgttgaat    5940
actcatactc ttcctttttc aatattattg aagcatttat cagggttatt gtctcatgag    6000
cggatacata tttgaatgta tttagaaaaa taaacaaata ggggttccgc gcacatttcc    6060
ccgaaaagtg ccacctgacg tc                                             6082

<210> SEQ ID NO 11
<211> LENGTH: 6085
<212> TYPE: DNA
<213> ORGANISM: Artificial Sequence
<220> FEATURE:
<223> OTHER INFORMATION: Plasmid

<400> SEQUENCE: 11
gacggatcgg gagatctccc gatcccctat ggtcgactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggac tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
```

```
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctaga      900
aagcttggat ctcaccatga gggtccccgc tcagcttctc ttccttctgc tactctggct      960
cccagatacc actggaggaa tagtgatgac gcagtctcca gccaccctgt ctgtgtctcc     1020
aggggaaaga gccaccctct cctgcaggac cagtcagagt attggctgga acttagcctg     1080
gtaccaacag aaacctggcc aggctcccag gctcctcatc tatggtgcat cttccaggac     1140
cactggtatc ccagccaggt tcagtggcag tgggtctggg acagagttca ctctcaccat     1200
cagcagcctg cagtctgaag attctgcagt ttattactgt cagcattatg ataactggcc     1260
catgtgcagt tttggccagg ggaccgagct ggagatcaaa cgaactgtgg ctgcaccatc     1320
tgtcttcatc ttcccgccat ctgatgagca gttgaaatct ggaactgcta gcgttgtgtg     1380
cctgctgaat aacttctatc ccagagaggc caaagtacag tggaaggtgg ataacgccct     1440
ccaatcgggt aactcccagg agagtgtcac agagcaggac agcaaggaca gcacctacag     1500
cctcagcagc accctgacgc tgagcaaagc agactacgag aaacacaaag tctacgcctg     1560
cgaagtcacc catcagggcc tgagctcgcc cgtcacaaag agcttcaaca ggggagagtg     1620
ttaggaattc gcggccgctc gagtctagag ggcccgttta acccgctga tcagcctcga     1680 ctgtgccttc tagttgccag ccatctgttg tttgcccctc cccgtgcct tccttgaccc     1740 tggaaggtgc cactcccact gtcctttcct aataaaatga ggaaattgca tcgcattgtc     1800
tgagtaggtg tcattctatt ctggggggtg gggtggggca ggacagcaag ggggaggatt     1860
gggaagacaa tagcaggcat gctggggatg cggtgggctc tatggcttct gaggcggaaa     1920
gaaccagctg gggctctagg gggtatcccc acgcgccctg tagcggcgca ttaagcgcgg     1980
cgggtgtggt ggttacgcgc agcgtgaccg ctacacttgc cagcgcccta gcgcccgctc     2040
ctttcgcttt cttcccttcc tttctcgcca cgttcgccgg ctttccccgt caagctctaa     2100 atcgggcat cccctttaggg ttccgattta gtgctttacg gcacctcgac cccaaaaaac     2160
ttgattaggg tgatggttca cgtagtgggc catcgccctg atagacggtt tttcgccctt     2220
tgacgttgga gtccacgttc tttaatagtg gactcttgtt ccaaactgga acaacactca     2280
accctatctc ggtctattct tttgatttat aagggatttt ggggatttcg gcctattggt     2340
taaaaaatga gctgatttaa caaaaattta acgcgaatta attctgtgga atgtgtgtca     2400
gttagggtgt ggaaagtccc caggctcccc aggcaggcag aagtatgcaa agcatgcatc     2460
tcaattagtc agcaaccagg tgtggaaagt cccaggctc cccagcaggc agaagtatgc     2520
aaagcatgca tctcaattag tcagcaacca tagtcccgcc cctaactccg cccatcccgc     2580
ccctaactcc gcccagttcc gcccattctc cgccccatgg ctgactaatt ttttttattt     2640
atgcagaggc cgaggccgcc tctgcctctg agctattcca gaagtagtga ggaggctttt     2700
ttggaggcct aggcttttgc aaaaagctcc cgggagcttg tatatccatt ttcggatctg     2760
atcaagagac aggatgagga tcgtttcgca tgattgaaca agatggattg cacgcaggtt     2820
ctccggccgc ttgggtggag aggctattcg gctatgactg gcacaacag acaatcggct     2880 gctctgatgc cgccgtgttc cggctgtcag cgcaggggcg cccggttctt tttgtcaaga     2940
ccgacctgtc cggtgccctg aatgaactgc aggacgaggc agcgcggcta tcgtggctgg     3000
```

```
ccacgacggg cgttccttgc gcagctgtgc tcgacgttgt cactgaagcg ggaagggact    3060
ggctgctatt gggcgaagtg ccggggcagg atctcctgtc atctccctt gctcctgccg     3120 agaaagtatc catcatggct gatgcaatgc ggcggctgca tacgcttgat ccggctacct    3180
gcccattcga ccaccaagcg aaacatcgca tcgagcgagc acgtactcgg atggaagccg    3240
gtcttgtcga tcaggatgat ctggacgaag agcatcaggg gctcgcgcca gccgaactgt    3300
tcgccaggct caaggcgcgc atgcccgacg gcgaggatct cgtcgtgacc catggcgatg    3360
cctgcttgcc gaatatcatg gtggaaaatg gccgcttttc tggattcatc gactgtggcc    3420
ggctgggtgt ggcggaccgc tatcaggaca tagcgttggc tacccgtgat attgctgaag    3480
agcttggcgg cgaatgggct gaccgcttcc tcgtgcttta cggtatcgcc gctcccgatt    3540
cgcagcgcat cgccttctat cgccttcttg acgagttctt ctgagcggga ctctggggtt    3600
cgaaatgacc gaccaagcga cgcccaacct gccatcacga tttcgatt ccaccgccgc      3660 cttctatgaa aggttgggct tcggaatcgt tttccgggac gccggctgga tgatcctcca    3720
gcgcggggat ctcatgctgg agttcttcgc ccaccccaac ttgtttattg cagcttataa    3780
tggttacaaa taaagcaata gcatcacaaa tttcacaaat aaagcatttt tttcactgca    3840
ttctagttgt ggtttgtcca aactcatcaa tgtatcttat catgtctgta taccgtcgac    3900
ctctagctag agcttggcgt aatcatggtc atagctgttt cctgtgtgaa attgttatcc    3960
gctcacaatt ccacacaaca tacgagccgg aagcataaag tgtaaagcct ggggtgccta    4020
atgagtgagc taactcacat taattgcgtt gcgctcactg cccgctttcc agtcgggaaa    4080
cctgtcgtgc cagctgcatt aatgaatcgg ccaacgcgcg gggagaggcg gtttgcgtat    4140
tgggcgctct tccgcttcct cgctcactga ctcgctgcgc tcggtcgttc ggctgcggcg    4200
agcggtatca gctcactcaa aggcggtaat acgttatcc acagaatcag gggataacgc     4260
aggaaagaac atgtgagcaa aaggccagca aaaggccagg aaccgtaaaa aggccgcgtt    4320
gctgcgtttt tccataggc tccgcccccc tgacgagcat cacaaaaatc gacgctcaag     4380
tcagaggtgg cgaaacccga caggactata agataccag gcgtttcccc ctggaagctc      4440
cctcgtgcgc tctcctgttc cgaccctgcc gcttaccgga tacctgtccg cctttctccc    4500
ttcgggaagc gtggcgcttt ctcaatgctc acgctgtagg tatctcagtt cggtgtaggt    4560
cgttcgctcc aagctgggct gtgtgcacga accccccgtt cagcccgacc gctgcgcctt    4620
atccggtaac tatcgtcttg agtccaaccc ggtaagacac gacttatcgc cactggcagc    4680
agccactggt aacaggatta gcagagcgag gtatgtaggc ggtgctacag agttcttgaa    4740
gtggtggcct aactacggct acactagaag gacagtattt ggtatctgcg ctctgctgaa    4800
gccagttacc ttcggaaaaa gagttggtag ctcttgatcc ggcaaacaaa ccaccgctgg    4860
tagcggtggt ttttttgttt gcaagcagca gattacgcgc agaaaaaaag gatctcaaga    4920
agatcctttg atcttttcta cggggtctga cgctcagtgg aacgaaaact cacgttaagg    4980
gattttggtc atgagattat caaaaaggat cttcacctag atcctttaa attaaaaatg     5040 aagttttaaa tcaatctaaa gtatatatga gtaaacttgg tctgacagtt accaatgctt    5100
aatcagtgag gcacctatct cagcgatctg tctatttcgt tcatccatag ttgcctgact    5160
ccccgtcgtg tagataacta cgatacggga gggcttacca tctggcccca gtgctgcaat    5220
gataccgcga gacccacgct caccggctcc agatttatca gcaataaacc agccagccgg    5280
aagggccgag cgcagaagtg gtcctgcaac tttatccgcc tccatccagt ctattaattg    5340
ttgccgggaa gctagagtaa gtagttcgcc agttaatagt ttgcgcaacg ttgttgccat    5400
```

```
tgctacaggc atcgtggtgt cacgctcgtc gtttggtatg gcttcattca gctccggttc   5460
ccaacgatca aggcgagtta catgatcccc catgttgtgc aaaaaagcgg ttagctcctt   5520
cggtcctccg atcgttgtca gaagtaagtt ggccgcagtg ttatcactca tggttatggc   5580
agcactgcat aattctctta ctgtcatgcc atccgtaaga tgcttttctg tgactggtga   5640
gtactcaacc aagtcattct gagaatagtg tatgcggcga ccgagttgct cttgcccggc   5700
gtcaatacgg gataataccg cgccacatag cagaacttta aaagtgctca tcattggaaa   5760
acgttcttcg gggcgaaaac tctcaaggat cttaccgctg ttgagatcca gttcgatgta   5820
acccactcgt gcacccaact gatcttcagc atctttact  ttcaccagcg tttctgggtg   5880
agcaaaaaca ggaaggcaaa atgccgcaaa aaagggaata agggcgacac ggaaatgttg   5940
aatactcata ctcttccttt ttcaatatta ttgaagcatt tatcagggtt attgtctcat   6000
gagcggatac atatttgaat gtatttagaa aaataaacaa ataggggttc cgcgcacatt   6060
tccccgaaaa gtgccacctg acgtc                                          6085
```

<210> SEQ ID NO 12
<211> LENGTH: 6097
<212> TYPE: DNA
<213> ORGANISM: Artificial Sequence
<220> FEATURE:
<223> OTHER INFORMATION: Plasmid

<400> SEQUENCE: 12

```
gacggatcgg gagatctccc gatccctat  ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc  cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aagcttggat ctcaccatga gggtccctgc tcagctcctg ggctgctaa  tgctctggat    960
acctggatcc agtgcagata ttgtgatgac ccagactcca ctctctctgt ccgtcacccc   1020
tggacagccg gcctccatct cctgcaagtc tagtcagagc ctcctgcata gtgatggaaa   1080
gaccttttg  tattggtatc tgcagaagcc aggccagcct ccacagctcc tgatctatga   1140
ggtttccaac cggttctctg gagtgccaga taggttcagt ggcagcgggt cagggacaga   1200
tttcacactg aaaatcagcc gggtggaggc tgaggatgtt gggctttatt actgcatgca   1260
aagtatacag cttccgctca ctttcggcgg agggaccaag gtggagatca aacgaactgt   1320
```

```
ggctgcacca tctgtcttca tcttcccgcc atctgatgag cagttgaaat ctggaactgc    1380
tagcgttgtg tgcctgctga ataacttcta tcccagagag ccaaagtac  agtggaaggt    1440 ggataacgcc ctccaatcgg gtaactccca ggagagtgtc acagagcagg acagcaagga    1500
cagcacctac agcctcagca gcaccctgac gctgagcaaa gcagactacg agaaacacaa    1560
agtctacgcc tgcgaagtca cccatcaggg cctgagctcg cccgtcacaa agagcttcaa    1620
caggggagag tgttaggaat tcgcggccgc tcgagtctag agggcccgtt taaacccgct    1680
gatcagcctc gactgtgcct tctagttgcc agccatctgt tgtttgcccc tcccccgtgc    1740
cttccttgac cctggaaggt gccactccca ctgtcctttc ctaataaaat gaggaaattg    1800
catcgcattg tctgagtagg tgtcattcta ttctgggggg tggggtgggg caggacagca    1860
agggggagga ttgggaagac aatagcaggc atgctgggga tgcggtgggc tctatggctt    1920
ctgaggcgga aagaaccagc tggggctcta ggggtatccc cacgcgccc  tgtagcggcg    1980 cattaagcgc ggcgggtgtg gtggttacgc gcagcgtgac cgctacactt gccagcgccc    2040
tagcgcccgc tcctttcgct ttcttccctt cctttctcgc cacgttcgcc ggctttcccc    2100
gtcaagctct aaatcggggc atccctttag ggttccgatt tagtgcttta cggcacctcg    2160
accccaaaaa acttgattag ggtgatggtt cacgtagtgg gccatcgccc tgatagacgg    2220
tttttcgccc tttgacgttg gagtccacgt tctttaatag tggactcttg ttccaaactg    2280
gaacaacact caaccctatc tcggtctatt cttttgattt ataagggatt ttggggattt    2340
cggcctattg gttaaaaaat gagctgattt aacaaaaatt taacgcgaat taattctgtg    2400
gaatgtgtgt cagttagggt gtggaaagtc cccaggctcc ccaggcaggc agaagtatgc    2460
aaagcatgca tctcaattag tcagcaacca ggtgtggaaa gtccccaggc tccccagcag    2520
gcagaagtat gcaaagcatg catctcaatt agtcagcaac catagtcccg cccctaactc    2580
cgcccatccc gcccctaact ccgcccagtt ccgcccattc tccgccccat ggctgactaa    2640
ttttttttat ttatgcagag gccgaggccg cctctgcctc tgagctattc cagaagtagt    2700
gaggaggctt ttttggaggc ctaggctttt gcaaaaagct cccgggagct tgtatatcca    2760
ttttcggatc tgatcaagag acaggatgag gatcgtttcg catgattgaa caagatggat    2820
tgcacgcagg ttctccggcc gcttgggtgg agaggctatt cggctatgac tgggcacaac    2880
agacaatcgg ctgctctgat gccgccgtgt tccggctgtc agcgcagggg cgcccggttc    2940
tttttgtcaa gaccgacctg tccggtgccc tgaatgaact gcaggacgag gcagcgcggc    3000
tatcgtggct ggccacgacg ggcgttcctt gcgcagctgt gctcgacgtt gtcactgaag    3060
cgggaaggga ctggctgcta ttgggcgaag tgccggggca ggatctcctg tcatctcacc    3120
ttgctcctgc cgagaaagta tccatcatgg ctgatgcaat gcggcggctg catacgcttg    3180
atccggctac ctgcccattc gaccaccaag cgaaacatcg catcgagcga gcacgtactc    3240
ggatggaagc cggtcttgtc gatcaggatg atctggacga agagcatcag gggctcgcgc    3300
cagccgaact gttcgccagg ctcaaggcgc gcatgcccga cggcgaggat ctcgtcgtga    3360
cccatggcga tgcctgcttg ccgaatatca tggtggaaaa tggccgcttt tctggattca    3420
tcgactgtgg ccggctgggt gtggcggacc gctatcagga catagcgttg ctacccgtg    3480 atattgctga agagcttggc ggcgaatggg ctgaccgctt cctcgtgctt tacggtatcg    3540
ccgctcccga ttcgcagcgc atcgccttct atcgccttct tgacgagttc ttctgagcgg    3600
gactctgggg ttcgaaatga ccgaccaagc gacgcccaac ctgccatcac gagatttcga    3660
ttccaccgcc gccttctatg aaaggttggg cttcggaatc gttttccggg acgccggctg    3720
```

-continued

```
gatgatcctc cagcgcgggg atctcatgct ggagttcttc gcccacccca acttgtttat    3780
tgcagcttat aatggttaca ataaagcaa tagcatcaca aatttcacaa ataaagcatt     3840
ttttcactg cattctagtt gtggtttgtc caaactcatc aatgtatctt atcatgtctg     3900
tataccgtcg acctctagct agagcttggc gtaatcatgg tcatagctgt ttcctgtgtg    3960
aaattgttat ccgctcacaa ttccacacaa catacgagcc ggaagcataa agtgtaaagc    4020
ctggggtgcc taatgagtga gctaactcac attaattgcg ttgcgctcac tgcccgcttt    4080
ccagtcggga aacctgtcgt gccagctgca ttaatgaatc ggccaacgcg cggggagagg    4140
cggtttgcgt attgggcgct cttccgcttc ctcgctcact gactcgctgc gctcggtcgt    4200
tcggctgcgg cgagcggtat cagctcactc aaaggcggta atacggttat ccacagaatc    4260
aggggataac gcaggaaaga acatgtgagc aaaaggccag caaaaggcca ggaaccgtaa    4320
aaaggccgcg ttgctggcgt ttttccatag gctccgcccc cctgacgagc atcacaaaaa    4380
tcgacgctca gtcagaggt ggcgaaaccc gacaggacta taaagatacc aggcgtttcc     4440
ccctggaagc tccctcgtgc gctctcctgt tccgaccctg ccgcttaccg gatacctgtc    4500
cgcctttctc ccttcgggaa gcgtggcgct ttctcaatgc tcacgctgta ggtatctcag    4560
ttcggtgtag gtcgttcgct ccaagctggg ctgtgtgcac gaaccccccg ttcagcccga    4620
ccgctgcgcc ttatccggta actatcgtct gagtccaac ccgtaagac acgacttatc      4680
gccactggca gcagccactg gtaacaggat tagcagagcg aggtatgtag cggtgctac     4740
agagttcttg aagtggtggc ctaactacgg ctacactaga aggacagtat ttggtatctg    4800
cgctctgctg aagccagtta ccttcggaaa aagagttggt agctcttgat ccggcaaaca    4860
aaccaccgct ggtagcggtg gtttttttgt ttgcaagcag cagattacgc gcagaaaaaa    4920
aggatctcaa gaagatcctt tgatctttc tacggggtct gacgctcagt ggaacgaaaa     4980
ctcacgttaa gggattttgg tcatgagatt atcaaaaagg atcttcacct agatccttt     5040
aaattaaaaa tgaagtttta aatcaatcta agtatatat gagtaaactt ggtctgacag     5100
ttaccaatgc ttaatcagtg aggcaccat ctcagcgatc tgtctatttc gttcatccat     5160
agttgcctga ctccccgtcg tgtagataac tacgatacgg gagggcttac catctggccc    5220
cagtgctgca atgataccgc gagacccacg ctcaccggct ccagatttat cagcaataaa    5280
ccagccagcc ggaagggccg agcgcagaag tggtcctgca actttatccg cctccatcca    5340
gtctattaat tgttgccggg aagctagagt aagtagttcg ccagttaata gtttgcgcaa    5400
cgttgttgcc attgctacag gcatcgtggt gtcacgctcg tcgtttggta tggcttcatt    5460
cagctccggt tcccaacgat caaggcgagt tacatgatcc cccatgttgt gcaaaaaagc    5520
ggttagctcc ttcggtcctc cgatcgttgt cagaagtaag ttggccgcag tgttatcact    5580
catggttatg gcagcactgc ataattctct tactgtcatg ccatccgtaa gatgcttttc    5640
tgtgactggt gagtactcaa ccaagtcatt ctgagaatag tgtatgcggc gaccgagttg    5700
ctcttgcccg gcgtcaatac gggataatac cgcgccacat agcagaactt taaaagtgct    5760
catcattgga aaacgttctt cggggcgaaa actctcaagg atcttaccgc tgttgagatc    5820
cagttcgatg taacccactc gtgcacccaa ctgatcttca gcatctttta ctttcaccag    5880
cgtttctggg tgagcaaaaa caggaaggca aaatgccgca aaaagggaa taagggcgac    5940
acggaaatgt tgaatactca tactcttcct ttttcaatat tattgaagca tttatcaggg    6000
ttattgtctc atgagcggat acatatttga atgtatttag aaaaataaac aatagggt     6060
```

```
tccgcgcaca tttccccgaa aagtgccacc tgacgtc                              6097
```

<210> SEQ ID NO 13
<211> LENGTH: 6094
<212> TYPE: DNA
<213> ORGANISM: Artificial Sequence
<220> FEATURE:
<223> OTHER INFORMATION: Plasmid

<400> SEQUENCE: 13

```
gacggatcgg gagatctccc gatcccctat ggtcgactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctaga    900
aagcttggat ctcaccatgg tgttgcagac ccaggtcttc atttctctgt tactctggat    960
ctctggtgcc tacggggaca tcgtgatgac ccagtctcca gactccctgg ctgtgtctct   1020
gggcgagagg gccaccatca actgcaagtc caaccagagt gtcttacaca gctccaacaa   1080
taagaactat ttagcttggt accagcagaa accaggacag cctcctaaat tgctcattta   1140
ttgggcattc ctccgggaat ccggggtccc tgaccgcttc agtggcagcg gtctgggac   1200
agatttcact ctcaccatca gcagcctgca ggctgaagat gtggcagttt attactgtca   1260
ccaatattat tctactttat atacttcgg cggagggacc aaggtagaga tcaaacgaac   1320
ygtggctgca ccatctgtct tcatcttccc gccatctgat gagcagttga atctggaac   1380
tgctagcgtt gtgtgcctgc tgaataactt ctatcccaga gaggccaaag tacagtggaa   1440
ggtggataac gccctccaat cgggtaactc ccaggagagt gtcacagagc aggacagcaa   1500
ggacagcacc tacagcctca gcagcaccct gacgctgagc aaagcagact acgagaaaca   1560
caaagtctac gcctgcgaag tcacccatca gggcctgagc tcgcccgtca caaagagctt   1620
caacagggga gagtgttagg cggccgctcg agtctagagg gcccgtttaa acccgctgat   1680
cagcctcgac tgtgccttct agttgccagc catctgttgt ttgcccctcc cccgtgcctt   1740
ccttgaccct ggaaggtgcc actcccactg tcctttccta ataaaatgag gaaattgcat   1800
cgcattgtct gagtaggtgt cattctattc tggggggtgg ggtggggcag gacagcaagg   1860
gggaggattg ggaagacaat agcaggcatg ctggggatgc ggtgggctct atggcttctg   1920
aggcggaaag aaccagctgg ggctctaggg ggtatcccca cgcgccctgt agcggcgcat   1980
taagcgcggc gggtgtggtg gttacgcgca gcgtgaccgc tacacttgcc agcgccctag   2040
```

```
cgcccgctcc tttcgctttc ttcccttcct ttctcgccac gttcgccggc tttccccgtc    2100
aagctctaaa tcggggcatc cctttagggt tccgatttag tgctttacgg cacctcgacc    2160
ccaaaaaact tgattagggt gatggttcac gtagtgggcc atcgccctga tagacggttt    2220
ttcgcccttt gacgttggag tccacgttct ttaatagtgg actcttgttc caaactggaa    2280
caacactcaa ccctatctcg gtctattctt ttgatttata agggattttg gggatttcgg    2340
cctattggtt aaaaaatgag ctgatttaac aaaaatttaa cgcgaattaa ttctgtggaa    2400
tgtgtgtcag ttagggtgtg aaagtcccca ggctcccca ggcaggcaga agtatgcaaa    2460
gcatgcatct caattagtca gcaaccaggt gtggaaagtc cccaggctcc ccagcaggca    2520
gaagtatgca aagcatgcat ctcaattagt cagcaaccat agtcccgccc ctaactccgc    2580
ccatcccgcc cctaactccg cccagttccg cccattctcc gccccatggc tgactaattt    2640
tttttattta tgcagaggcc gaggccgcct ctgcctctga gctattccag aagtagtgag    2700
gaggcttttt tggaggccta ggcttttgca aaaagctccc gggagcttgt atatccattt    2760
tcggatctga tcaagagaca ggatgaggat cgtttcgcat gattgaacaa gatggattgc    2820
acgcaggttc tccggccgct tgggtggaga ggctattcgg ctatgactgg gcacaacaga    2880
caatcggctg ctctgatgcc gccgtgttcc ggctgtcagc gcaggggcgc ccggttcttt    2940
ttgtcaagac cgacctgtcc ggtgccctga atgaactgca ggacgaggca gcgcggctat    3000
cgtggctggc cacgacgggc gttccttgcg cagctgtgct cgacgttgtc actgaagcgg    3060
gaagggactg gctgctattg ggcgaagtgc cggggcagga tctcctgtca tctcaccttg    3120
ctcctgccga gaaagtatcc atcatggctg atgcaatgcg gcggctgcat acgcttgatc    3180
cggctacctg cccattcgac caccaagcga aacatcgcat cgagcgagca cgtactcgga    3240
tggaagccgg tcttgtcgat caggatgatc tggacgaaga gcatcagggg ctcgcgccag    3300
ccgaactgtt cgccaggctc aaggcgcgca tgcccgacgg cgaggatctc gtcgtgaccc    3360
atggcgatgc ctgcttgccg aatatcatgg tggaaaatgg ccgcttttct ggattcatcg    3420
actgtggccg ctgggtgtg gcggaccgct atcaggacat agcgttggct acccgtgata    3480
ttgctgaaga gcttggcggc gaatgggctg accgcttcct cgtgctttac ggtatcgccg    3540
ctcccgattc gcagcgcatc gccttctatc gccttcttga cgagttcttc tgagcgggac    3600 tctgggttc gaaatgaccg accaagcgac gcccaacctg ccatcacgag atttcgattc    3660
caccgccgcc ttctatgaaa ggttgggctt cggaatcgtt ttccgggacg ccggctggat    3720
gatcctccag cgcggggatc tcatgctgga gttcttcgcc cacccaact tgtttattgc    3780 agcttataat ggttacaaat aaagcaatag catcacaaat ttcacaaata aagcattttt    3840
ttcactgcat tctagttgtg gtttgtccaa actcatcaat gtatcttatc atgtctgtat    3900
accgtcgacc tctagctaga gcttggcgta atcatggtca tagctgtttc ctgtgtgaaa    3960
ttgttatccg ctcacaattc cacacaacat acgagccgga agcataaagt gtaaagcctg    4020
gggtgcctaa tgagtgagct aactcacatt aattgcgttg cgctcactgc ccgctttcca    4080
gtcgggaaac ctgtcgtgcc agctgcatta atgaatcggc caacgcgcgg ggagaggcgg    4140
tttgcgtatt gggcgctctt ccgcttcctc gctcactgac tcgctgcgct cggtcgttcg    4200
gctgcggcga gcggtatcag ctcactcaaa ggcggtaata cggttatcca cagaatcagg    4260
ggataacgca ggaaagaaca tgtgagcaaa aggccagcaa aaggccagga accgtaaaaa    4320
ggccgcgttg ctggcgtttt tccataggct ccgcccccct gacgagcatc acaaaaatcg    4380
```

-continued

```
acgctcaagt cagaggtggc gaaacccgac aggactataa agataccagg cgtttccccc      4440
tggaagctcc ctcgtgcgct ctcctgttcc gaccctgccg cttaccggat acctgtccgc      4500
ctttctccct tcgggaagcg tggcgctttc tcaatgctca cgctgtaggt atctcagttc      4560
ggtgtaggtc gttcgctcca agctgggctg tgtgcacgaa ccccccgttc agcccgaccg      4620
ctgcgcctta tccggtaact atcgtcttga gtccaacccg gtaagacacg acttatcgcc      4680
actggcagca gccactggta acaggattag cagagcgagg tatgtaggcg gtgctacaga      4740
gttcttgaag tggtggccta actacggcta cactagaagg acagtatttg gtatctgcgc      4800
tctgctgaag ccagttacct tcggaaaaag agttggtagc tcttgatccg gcaaacaaac      4860
caccgctggt agcggtggtt ttttttgttttg caagcagcag attacgcgca gaaaaaaagg      4920
atctcaagaa gatcctttga tcttttctac ggggtctgac gctcagtgga acgaaaactc      4980
acgttaaggg attttggtca tgagattatc aaaaaggatc ttcacctaga tccttttaaa      5040
ttaaaaatga agttttaaat caatctaaag tatatatgag taaacttggt ctgacagtta      5100
ccaatgctta atcagtgagg cacctatctc agcgatctgt ctatttcgtt catccatagt      5160
tgcctgactc cccgtcgtgt agataactac gatacgggag ggcttaccat ctggccccag      5220
tgctgcaatg ataccgcgag acccacgctc accggctcca gatttatcag caataaacca      5280
gccagccgga agggccgagc gcagaagtgg tcctgcaact ttatccgcct ccatccagtc      5340
tattaattgt tgccgggaag ctagagtaag tagttcgcca gttaatagtt tgcgcaacgt      5400
tgttgccatt gctacaggca tcgtggtgtc acgctcgtcg tttggtatgg cttcattcag      5460
ctccggttcc caacgatcaa ggcgagttac atgatccccc atgttgtgca aaaaagcggt      5520
tagctccttc ggtcctccga tcgttgtcag aagtaagttg gccgcagtgt tatcactcat      5580
ggttatggca gcactgcata attctcttac tgtcatgcca tccgtaagat gcttttctgt      5640
gactggtgag tactcaacca agtcattctg agaatagtgt atgcggcgac cgagttgctc      5700
ttgcccggcg tcaatacggg ataataccgc gccacatagc agaactttaa aagtgctcat      5760
cattggaaaa cgttcttcgg ggcgaaaact ctcaaggatc ttaccgctgt tgagatccag      5820
ttcgatgtaa cccactcgtg cacccaactg atcttcagca tcttttactt tcaccagcgt      5880
ttctgggtga gcaaaaacag gaaggcaaaa tgccgcaaaa aagggaataa gggcgacacg      5940
gaaatgttga atactcatac tcttcctttt tcaatattat tgaagcattt atcagggtta      6000
ttgtctcatg agcggataca tatttgaatg tatttagaaa aataaacaaa tagggggttcc      6060 gcgcacattt ccccgaaaag tgccacctga cgtc                                 6094
```

<210> SEQ ID NO 14
<211> LENGTH: 481
<212> TYPE: DNA
<213> ORGANISM: Artificial Sequence
<220> FEATURE:
<223> OTHER INFORMATION: Includes BamHI/BglII cloning junction, signal
      peptide, V region, portion of C region and 3'XbaI/NheI (heavy) or
      NheI (light) cloning junction

<400> SEQUENCE: 14

```
ggatctcacc atggagttgg gactgcgctg gggcttcctc gttgctcttt taagaggtgt       60
ccagtgtcag gtgcaattgg tggagtctgg gggaggcgtg gtccagcctg gaggtccct      120 gagactctcc tgtgcagcgt ctggattcgc cttcagtaga tatggcatgc actgggtccg      180
ccaggctcca ggcaagggc tggagtgggt ggcagttata tggtatgatg gaagtaataa      240
atactatgca gactccgtga agggccgatt caccatctcc agagacaatt ccaagaacac      300
```

```
gcagtatctg caaatgaaca gcctgagagc cgaggacacg gctgtgtatt actgtgcgag    360
aggcggtgac ttcctctact actactatta cggtatggac gtctggggcc aagggaccac    420
ggtcaccgtc tcctcagcct ccaccaaggg cccatcggtc ttccccctgg caccctctag    480
c                                                                    481
```

<210> SEQ ID NO 15
<211> LENGTH: 142
<212> TYPE: PRT
<213> ORGANISM: Homo sapiens

<400> SEQUENCE: 15

```
Met Glu Leu Gly Leu Arg Trp Gly Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Ala Phe
        35                  40                  45

Ser Arg Tyr Gly Met His Trp Val Arg Gln Ala Pro Gly Lys Gly Leu
    50                  55                  60

Glu Trp Val Ala Val Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Gln Tyr Leu Gln Met Asn Ser Leu Arg Ala Glu Asp Thr Ala Val
            100                 105                 110

Tyr Tyr Cys Ala Arg Gly Gly Asp Phe Leu Tyr Tyr Tyr Tyr Gly
        115                 120                 125

Met Asp Val Trp Gly Gln Gly Thr Thr Val Thr Val Ser Ser
    130                 135                 140
```

<210> SEQ ID NO 16
<211> LENGTH: 463
<212> TYPE: DNA
<213> ORGANISM: Artificial Sequence
<220> FEATURE:
<223> OTHER INFORMATION: Includes BamHI/BglII cloning junction, signal
      peptide, V region, portion of C region and 3'XbaI/NheI (heavy) or
      NheI (light) cloning junction

<400> SEQUENCE: 16

```
ggatctcacc atgagggtcc ctgctcagct cctgggactc ctgctgctct ggctcccaga     60
taccagatgt gacatccaga tgacccagtc tccatcctcc ctgtctgcat ctgtaggaga    120
cagagtcacc atcacttgcc gggcgagtca gggcattagc aattatttag cctggtatca    180
gcagaaaaca gggaaagttc ctaagttcct gatctatgaa gcatccactt tgcaatcagg    240
ggtcccatct cggttcagtg gcggtggatc tgggacagat ttcactctca ccatcagcag    300
cctgcagcct gaagatgttg caacttatta ctgtcaaaat tataacagtg ccccattcac    360
tttcggccct gggaccaaag tggatatcaa acgaactgtg gctgcaccct ctgtcttcat    420
cttcccgcca tctgatgagc agttgaaatc tggaactgct agc                      463
```

<210> SEQ ID NO 17
<211> LENGTH: 127
<212> TYPE: PRT
<213> ORGANISM: Homo sapiens

<400> SEQUENCE: 17

Met Arg Val Pro Ala Gln Leu Leu Gly Leu Leu Leu Leu Trp Leu Pro
1               5                   10                  15

Asp Thr Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Asn Tyr Leu Ala Trp Tyr Gln Gln Lys Thr Gly Lys Val Pro
    50                  55                  60

Lys Phe Leu Ile Tyr Glu Ala Ser Thr Leu Gln Ser Gly Val Pro Ser
65                  70                  75                  80

Arg Phe Ser Gly Gly Gly Ser Gly Thr Asp Phe Thr Leu Thr Ile Ser
                85                  90                  95

Ser Leu Gln Pro Glu Asp Val Ala Thr Tyr Tyr Cys Gln Asn Tyr Asn
            100                 105                 110

Ser Ala Pro Phe Thr Phe Gly Pro Gly Thr Lys Val Asp Ile Lys
            115                 120                 125

<210> SEQ ID NO 18
<211> LENGTH: 508
<212> TYPE: DNA
<213> ORGANISM: Artificial Sequence
<220> FEATURE:
<223> OTHER INFORMATION: Includes BamHI/BglII cloning junction, signal
      peptide, V region, portion of C region and 3'XbaI/NheI (heavy) or
      NheI (light) cloning junction

<400> SEQUENCE: 18
ggatctcacc atggggtcaa ccgccatcct caccatggag ttggggctgc gctgggttct     60
cctcgttgct cttttaagag gtgtccagtg tcaggtgcag ctggtggagt ctggggagg    120 cgtggtccag cctgggaggt ccctgagact ctcctgtgca gcgtctggat tcaccttcag    180
taactatgtc atgcactggg tccgccaggc tccaggcaag gggctggagt gggtggcaat    240
tatatggtat gatggaagta ataaatacta tgcagactcc gtgaagggcc gattcaccat    300
ctccagagac aattccaaga acacgctgta tctgcaaatg aacagcctga gagccgagga    360
cacggctgtg tattactgtg cgggtggata taactggaac tacgagtacc actactacgg    420
tatggacgtc tggggccaag ggaccacggt caccgtctcc tcagcctcca ccaagggccc    480
atcggtcttc cccctggcac cctctagc                                       508

<210> SEQ ID NO 19
<211> LENGTH: 143
<212> TYPE: PRT
<213> ORGANISM: Homo sapiens

<400> SEQUENCE: 19

Met Glu Leu Gly Leu Arg Trp Val Leu Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Val Met His Trp Val Arg Gln Ala Pro Gly Lys Gly Leu
    50                  55                  60

Glu Trp Val Ala Ile Ile Trp Tyr Asp Gly Ser Asn Lys Tyr Tyr Ala
65                  70                  75                  80

Asp Ser Val Lys Gly Arg Phe Thr Ile Ser Arg Asp Asn Ser Lys Asn 85                  90                  95
Thr Leu Tyr Leu Gln Met Asn Ser Leu Arg Ala Glu Asp Thr Ala Val
            100                 105                 110

Tyr Tyr Cys Ala Gly Gly Tyr Asn Trp Asn Tyr Glu Tyr His Tyr Tyr
        115                 120                 125

Gly Met Asp Val Trp Gly Gln Gly Thr Thr Val Thr Val Ser Ser
    130                 135                 140

<210> SEQ ID NO 20
<211> LENGTH: 463
<212> TYPE: DNA
<213> ORGANISM: Artificial Sequence
<220> FEATURE:
<223> OTHER INFORMATION: Includes BamHI/BglII cloning junction, signal
      peptide, V region, portion of C region and 3'XbaI/NheI (heavy) or
      NheI (light) cloning junction

<400> SEQUENCE: 20
ggatctcacc atgagggtcc ccgctcagct cctggggctc ctgctgctct gtttcccagg     60
tgccagatgt gacatccaga tgacccagtc tccatcctca ctgtctgcat ctgtaggaga   120
cagagtcacc atcacttgtc gggcgagtca gggcattacc aattatttag cctggtttca   180
gcagaaacca gggaaagccc ctaagtccct tatctatgct gcatccagtt tgcaaagtgg   240
ggtcccatca aagttcagcg gcagtggatc tgggacagat ttcagtctca ccatcagcag   300
cctgcagcct gaagattttg caacttatta ctgccaacag tataatagtt acccgatcac   360
cttcggccaa gggacacgac tggagattaa acgaactgtg gctgcaccat ctgtcttcat   420
cttcccgcca tctgatgagc agttgaaatc tggaactgct agc                     463

<210> SEQ ID NO 21
<211> LENGTH: 127
<212> TYPE: PRT
<213> ORGANISM: Homo sapiens

<400> SEQUENCE: 21

Met Arg Val Pro Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Thr Asn Tyr Leu Ala Trp Phe Gln Gln Lys Pro Gly Lys Ala Pro
    50                  55                  60

Lys Ser Leu Ile Tyr Ala Ala Ser Ser Leu Gln Ser Gly Val Pro Ser
65                  70                  75                  80

Lys Phe Ser Gly Ser Gly Ser Gly Thr Asp Phe Ser Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Ile Thr Phe Gly Gln Gly Thr Arg Leu Glu Ile Lys
        115                 120                 125

<210> SEQ ID NO 22
<211> LENGTH: 490
<212> TYPE: DNA
<213> ORGANISM: Artificial Sequence
<220> FEATURE:
<223> OTHER INFORMATION: Includes BamHI/BglII cloning junction, signal
      peptide, V region, portion of C region and 3'XbaI/NheI (heavy) or NheI (light) cloning junction

<400> SEQUENCE: 22

```
ggatctcacc atggagttgg acttagctg ggttttcctc gttgctcttt taagaggtgt    60
ccagtgtcag gtccagctgg tggagtctgg gggaggcgtg gtccagcctg ggaggtccct  120
gagactctcc tgtgcagcgt ctggattcac cttcagtagc tatggcatgc actgggtccg  180
ccaggctcca ggcaagggggc tggactgggt ggcaattatt tggcatgatg gaagtaataa  240
atactatgca gactccgtga agggccgatt caccatctcc agagacaatt ccaagaagac  300
gctgtacctg caaatgaaca gtttgagagc cgaggacacg gctgtgtatt actgtgcgag  360
agcttgggcc tatgactacg gtgactatga atactacttc ggtatggacg tctggggcca  420
agggaccacg gtcaccgtct cctcagcctc caccaagggc ccatcggtct tccccctggc  480
accctctagc                                                         490
```

<210> SEQ ID NO 23
<211> LENGTH: 145
<212> TYPE: PRT
<213> ORGANISM: Homo sapiens

<400> SEQUENCE: 23

```
Met Glu Leu Gly Leu Ser Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Arg Ser Leu Arg Leu Ser Cys Ala Ala Ser Gly Phe Thr Phe
        35                  40                  45

Ser Ser Tyr Gly Met His Trp Val Arg Gln Ala Pro Gly Lys Gly Leu
    50                  55                  60

Asp Trp Val Ala Ile Ile Trp His Asp Gly Ser Asn Lys Tyr Tyr Ala
65                  70                  75                  80

Asp Ser Val Lys Gly Arg Phe Thr Ile Ser Arg Asp Asn Ser Lys Lys
                85                  90                  95

Thr Leu Tyr Leu Gln Met Asn Ser Leu Arg Ala Glu Asp Thr Ala Val
            100                 105                 110

Tyr Tyr Cys Ala Arg Ala Trp Ala Tyr Asp Tyr Gly Asp Tyr Glu Tyr
        115                 120                 125

Tyr Phe Gly Met Asp Val Trp Gly Gln Gly Thr Thr Val Thr Val Ser
    130                 135                 140

Ser
145
```

<210> SEQ ID NO 24
<211> LENGTH: 463
<212> TYPE: DNA
<213> ORGANISM: Artificial Sequence
<220> FEATURE:
<223> OTHER INFORMATION: Includes BamHI/BglII cloning junction, signal peptide, V region, portion of C region and 3'XbaI/NheI (heavy) or NheI (light) cloning junction

<400> SEQUENCE: 24

```
ggatctcacc atgagggtcc ctgctcagct cctggggctc ctgctgctct gtttcccagg    60
tgccagatgt gacatccaga tgacccagtc tccatcctca ctgtctgcat ctgtaggaga  120
cagagtcacc atcacttgtc gggcgagtca gggcattagc cattatttag cctggtttca  180
gcagaaacca gggaaagccc ctaagtccct gatctatgct gcatccagtt tgcaaagtgg  240
```

```
ggtcccatca aagttcagcg gcagtggatc tgggacagat ttcactctca ccatcagcag      300
cctacagcct gaagattttg caacttatta ctgccaacag tataatagtt tcccgctcac      360
tttcggcgga gggaccaagg tggagatcaa acgaactgtg ctgcaccat ctgtcttcat       420 cttcccgcca tctgatgagc agttgaaatc tggaactgct agc                        463
```

<210> SEQ ID NO 25
<211> LENGTH: 127
<212> TYPE: PRT
<213> ORGANISM: Homo sapiens

<400> SEQUENCE: 25

```
Met Arg Val Pro Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser His Tyr Leu Ala Trp Phe Gln Gln Lys Pro Gly Lys Ala Pro
    50                  55                  60

Lys Ser Leu Ile Tyr Ala Ala Ser Ser Leu Gln Ser Gly Val Pro Ser
65                  70                  75                  80

Lys Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Phe Pro Leu Thr Phe Gly Gly Gly Thr Lys Val Glu Ile Lys
        115                 120                 125
```

<210> SEQ ID NO 26
<211> LENGTH: 469
<212> TYPE: DNA
<213> ORGANISM: Artificial Sequence
<220> FEATURE:
<223> OTHER INFORMATION: Includes BamHI/BglII cloning junction, signal
      peptide, V region, portion of C region and 3'XbaI/NheI (heavy) or
      NheI (light) cloning junction

<400> SEQUENCE: 26

```
ggatcccacc atggggtcaa ccgtcatcct cgccctcctc ctggctgttc tccaaggagt      60
ctgtgccgag gtgcagctgg tgcagtctgg agcagaggtg aaaaagcccg gggagtctct      120
gaagatctcc tgtaagggtt ctggatacag ctttaccagt tactgatcg gctgggtgcg      180 ccagatgccc gggaaaggcc tggagtggat ggggatcatc tatcctggtg actctgatac      240
cagatacagc ccgtccttcc aaggccaggt caccatctca gccgacaagt ccatcagcac      300
cgcctacctg cagtggagca gcctgaaggc ctcggacacc gccatgtatt actgtgcgag      360
acggatggca gcagctggcc ctttgactac tggggccag ggaaccctgg tcaccgtctc       420
ctcagcctcc accaagggcc catcggtctt ccccctggca ccctctagc                  469
```

<210> SEQ ID NO 27
<211> LENGTH: 138
<212> TYPE: PRT
<213> ORGANISM: Homo sapiens

<400> SEQUENCE: 27

```
Met Gly Ser Thr Val Ile Leu Ala Leu Leu Leu Ala Val Leu Gln Gly
1               5                   10                  15
```

```
Val Cys Ala Glu Val Gln Leu Val Gln Ser Gly Ala Glu Val Lys Lys
            20                  25                  30

Pro Gly Glu Ser Leu Lys Ile Ser Cys Lys Gly Ser Gly Tyr Ser Phe
        35                  40                  45

Thr Ser Tyr Trp Ile Gly Trp Val Arg Gln Met Pro Gly Lys Gly Leu
    50                  55                  60

Glu Trp Met Gly Ile Ile Tyr Pro Gly Asp Ser Asp Thr Arg Tyr Ser
65                  70                  75                  80

Pro Ser Phe Gln Gly Gln Val Thr Ile Ser Ala Asp Lys Ser Ile Ser
                85                  90                  95

Thr Ala Tyr Leu Gln Trp Ser Ser Leu Lys Ala Ser Asp Thr Ala Met
            100                 105                 110

Tyr Tyr Cys Ala Arg Arg Met Ala Ala Ala Gly Pro Phe Asp Tyr Trp
        115                 120                 125

Gly Gln Gly Thr Leu Val Thr Val Ser Ser
130                 135
```

<210> SEQ ID NO 28
<211> LENGTH: 466
<212> TYPE: DNA
<213> ORGANISM: Artificial Sequence
<220> FEATURE:
<223> OTHER INFORMATION: Includes BamHI/BglII cloning junction, signal
      peptide, V region, portion of C region and 3'XbaI/NheI (heavy) or
      NheI (light) cloning junction

<400> SEQUENCE: 28
ggatctcacc atgagggtcc ccgctcagct tctcttcctt ctgctactct ggctcccaga    60
taccactgga ggaatagtga tgacgcagtc tccagccacc ctgtctgtgt ctccagggga   120
aagagccacc ctctcctgca ggaccagtca gagtattggc tggaacttag cctggtacca   180
acagaaacct ggccaggctc ccaggctcct catctatggt gcatcttcca ggaccactgg   240
tatcccagcc aggttcagtg cagtgggtc tgggacagag ttcactctca ccatcagcag   300
cctgcagtct gaagattctg cagtttatta ctgtcagcat tatgataact ggcccatgtg   360
cagttttggc caggggaccg agctggagat caaacgaact gtggctgcac catctgtctt   420
catcttcccg ccatctgatg agcagttgaa atctggaact gctagc                  466

<210> SEQ ID NO 29
<211> LENGTH: 128
<212> TYPE: PRT
<213> ORGANISM: Homo sapiens

<400> SEQUENCE: 29

```
Met Arg Val Pro Ala Gln Leu Leu Phe Leu Leu Leu Leu Trp Leu Pro
1               5                   10                  15

Asp Thr Thr Gly Gly Ile Val Met Thr Gln Ser Pro Ala Thr Leu Ser
            20                  25                  30

Val Ser Pro Gly Glu Arg Ala Thr Leu Ser Cys Arg Thr Ser Gln Ser
        35                  40                  45

Ile Gly Trp Asn Leu Ala Trp Tyr Gln Gln Lys Pro Gly Gln Ala Pro
    50                  55                  60

Arg Leu Leu Ile Tyr Gly Ala Ser Ser Arg Thr Thr Gly Ile Pro Ala
65                  70                  75                  80

Arg Phe Ser Gly Ser Gly Ser Gly Thr Glu Phe Thr Leu Thr Ile Ser
                85                  90                  95
```

```
Ser Leu Gln Ser Glu Asp Ser Ala Val Tyr Tyr Cys Gln His Tyr Asp
                100                 105                 110

Asn Trp Pro Met Cys Ser Phe Gly Gln Gly Thr Glu Leu Glu Ile Lys
        115                 120                 125
```

<210> SEQ ID NO 30
<211> LENGTH: 487
<212> TYPE: DNA
<213> ORGANISM: Artificial Sequence
<220> FEATURE:
<223> OTHER INFORMATION: Includes BamHI/BglII cloning junction, signal peptide, V region, portion of C region and 3'XbaI/NheI (heavy) or NheI (light) cloning junction

<400> SEQUENCE: 30

```
ggatctcacc atggagtttg ggctgtgctg gattttcctc gttgctcttt taagaggtgt    60
ccagtgtcag gtgcagctgg tggagtctgg gggaggcgtg gtccagcctg ggaggtccct   120
gagactctcc tgtgcagcct ctggattcac cttcattagc tatggcatgc actgggtccg   180
ccaggctcca ggcaaggggc tggagtgggt ggcagttata tcatatgatg gaagtaataa   240
atactatgca gactccgtga agggccgatt caccatctcc agagacaatt ccaagaacac   300
gctgtatctg caaatgaaca gcctgagagc tgaggacacg gctgtgtatt actgtgcgag   360
agtattagtg ggagctttat attattataa ctactacggg atggacgtct ggggccaagg   420
gaccacggtc accgtctcct cagcctccac caagggccca tcggtcttcc ccctggcacc   480
ctctagc                                                              487
```

<210> SEQ ID NO 31
<211> LENGTH: 144
<212> TYPE: PRT
<213> ORGANISM: Homo sapiens

<400> SEQUENCE: 31

```
Met Glu Phe Gly Leu Cys Trp Ile Phe Leu Val Ala Leu Leu Arg Gly
1               5                   10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Ile Ser Tyr Gly Met His Trp Val Arg Gln Ala Pro Gly Lys Gly Leu
        50                  55                  60

Glu Trp Val Ala Val Ile Ser Tyr Asp Gly Ser Asn Lys Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Val Leu Val Gly Ala Leu Tyr Tyr Tyr Asn Tyr
        115                 120                 125

Tyr Gly Met Asp Val Trp Gly Gln Gly Thr Thr Val Thr Val Ser Ser
    130                 135                 140
```

<210> SEQ ID NO 32
<211> LENGTH: 478
<212> TYPE: DNA
<213> ORGANISM: Artificial Sequence
<220> FEATURE:
<223> OTHER INFORMATION: Includes BamHI/BglII cloning junction, signal peptide, V region, portion of C region and 3'XbaI/NheI (heavy) or

```
           NheI (light) cloning junction

<400> SEQUENCE: 32
ggatctcacc atgagggtcc ctgctcagct cctggggctg ctaatgctct ggatacctgg      60
atccagtgca gatattgtga tgacccagac tccactctct ctgtccgtca cccctggaca     120
gccggcctcc atctcctgca agtctagtca gagcctcctg catagtgatg gaaagacctt     180
tttgtattgg tatctgcaga agccaggcca gcctccacag ctcctgatct atgaggtttc     240
caaccggttc tctggagtgc cagataggtt cagtggcagc gggtcaggga cagatttcac     300
actgaaaatc agccgggtgg aggctgagga tgttgggctt tattactgca tgcaaagtat     360
acagcttccg ctcactttcg gcggagggac caaggtggag atcaaacgaa ctgtggctgc     420
accatctgtc ttcatcttcc cgccatctga tgagcagttg aaatctggaa ctgctagc      478

<210> SEQ ID NO 33
<211> LENGTH: 132
<212> TYPE: PRT
<213> ORGANISM: Homo sapiens

<400> SEQUENCE: 33

Met Arg Val Pro Ala Gln Leu Leu Gly Leu Leu Met Leu Trp Ile Pro
1               5                   10                  15

Gly Ser Ser Ala Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu His Ser Asp Gly Lys Thr Phe Leu Tyr Trp Tyr Leu Gln Lys
    50                  55                  60

Pro Gly Gln Pro Pro Gln Leu Leu Ile Tyr Glu Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Leu Tyr Tyr
            100                 105                 110

Cys Met Gln Ser Ile Gln Leu Pro Leu Thr Phe Gly Gly Gly Thr Lys
        115                 120                 125

Val Glu Ile Lys
    130
```

METHODS FOR KILLING PSMA-EXPRESSING, TAXANE-RESISTANT CANCER CELLS

RELATED APPLICATIONS

This application is a continuation-in-part of International Application No. PCT/US2009/005064 designating the United States, filed Sep. 8, 2009, which claims the benefit under 35 U.S.C. §119 of U.S. provisional application 61/095,300, filed Sep. 8, 2008 and U.S. provisional application 61/205,395, filed Jan. 20, 2009, the contents of each of which are incorporated herein by reference in their entirety.

BACKGROUND OF THE INVENTION

Prostate cancer is the most common malignancy and the second leading cause of cancer death in men in the United States (Jemal A, et al., *CA Cancer J Clin* 2005; 55:10-30). Localized prostate cancer typically is treated with surgery or radiation, and recurrent disease can be controlled temporarily with androgen ablation (Klein E A, et al., *Urol Clin North Am* 2003; 30:315-30). However, almost all prostate carcinomas eventually become hormone refractory and then rapidly progress (Denmeade S R, et al., *Nat Rev Cancer* 2002; 2:389-96). Hormone-refractory or androgen-independent prostate cancer has proven to be largely resistant to conventional chemotherapy. With the exception of palliative care, the only approved chemotherapy is docetaxel in combination with prednisone, which offers a modest (2.4 month) survival benefit (Gulley J, et al., *Am J Ther.* 2004; 351:1513-20; Petrylak D P, et al., *New Engl J Med* 2004; 351:1513-20).

SUMMARY OF THE INVENTION

The present invention relates, at least in part, to the surprising discovery that antibody-drug conjugates (ADCs) comprising an antibody or antigen-binding fragment thereof that specifically binds PSMA conjugated to a dolastatin 10 derivative, in particular auristatins such as, MMAE (also referred to herein as monomethylauristatin E or monomethylauristatin norephedrine) or MMAF (also referred to herein as monomethylauristatin F or monomethylauristatin phenylalanine) can be used to kill PSMA-expressing, taxane-resistant cancer cells and to treat PSMA-expressing, taxane-resistant cancer. Provided herein, therefore, are methods for killing PSMA-expressing, taxane-resistant cancer cells. Also provided herein, are methods for treating a subject with a PSMA-expressing, taxane-resistant cancer. In one embodiment of the latter methods, the methods involve killing PSMA-expressing, taxane-resistant cancer cells. In another embodiment of the latter methods, the methods involve delaying or inhibiting progression of the cancer. In a further embodiment of the latter methods the method involves alleviating or decreasing pain in a subject (e.g., a human patient) having progressive, castration resistant, taxane-resistant metastatic prostate cancer comprising administering PSMA ADC in an amount effective to alleviate or decrease the level of pain in the subject. In one embodiment, the pain is bone pain. In one embodiment, the amount effective to alleviate or decrease the level of pain (e.g., bone pain) in the subject is a dose of PSMA ADC of at least 1.6 mg/kg or greater. In another embodiment, the amount effective is a dose of at least 1.8 mg·kg or greater. In yet another embodiment, the amount effective is a dose of at least 2.0 mg/kg or greater. In one embodiment, the dose is administered at 1, 2, 3 or 4 week intervals or more. In another embodiment, the dose is administered intravenously at 3 week intervals. In still other embodiments, the treatment is effective to reduce pain (e.g., bone pain) and the number of CTC cells in a subject. In yet another embodiment, the treatment is effective to reduce pain (e.g., bone pain) and PSA levels in a subject. In still other embodiments, the treatment is effective to reduce pain (e.g., bone pain), the number of CTC cells and PSA levels in a subject. In still another embodiment of the latter methods, the methods involve increasing survival of the subject as compared to the median survival of subjects not been treated with the PSMA ADC and that have progressive, castration-resistant, metastatic prostate cancer that has progressed after prior taxane therapy. In yet another embodiment of the latter methods, the methods involve decreasing a circulating level of circulating tumor cells (CTCs) compared to a baseline level. In a further embodiment of the latter methods, the methods involve decreasing or stabilizing a serum level of PSA compared to a baseline level of PSA.

In one aspect, therefore, a method for killing PSMA-expressing, taxane-resistant cancer cells comprising contacting the PSMA-expressing, taxane-resistant cancer cells with an antibody-drug conjugate in an amount effective to kill the PSMA-expressing, taxane-resistant cancer cells, wherein the antibody-drug conjugate comprises a monoclonal antibody or antigen-binding fragment thereof that specifically binds to prostate-specific membrane antigen (PSMA) conjugated to monomethylauristatin norephedrine or monomethylauristatin phenylalanine, and wherein the sequence of PSMA is the sequence set forth in SEQ ID NO: 1, is provided.

In another aspect, a method for treating a subject that has a PSMA-expressing, taxane-resistant cancer comprising administering to the subject that has the PSMA-expressing, taxane-resistant cancer an antibody-drug conjugate in an amount effective to treat the PSMA-expressing, taxane-resistant cancer, wherein the antibody-drug conjugate comprises a monoclonal antibody or antigen-binding fragment thereof that specifically binds to prostate-specific membrane antigen (PSMA) conjugated to monomethylauristatin norephedrine or monomethylauristatin phenylalanine, and wherein the sequence of PSMA is the sequence set forth in SEQ ID NO: 1, is also provided. In one embodiment, the method involves killing PSMA-expressing, taxane-resistant cancer cells. In another embodiment, the method involves delaying or inhibiting progression of the cancer. In a further embodiment, the method involves alleviating or decreasing pain in a subject (e.g., a human patient) having progressive, castration resistant, taxane-resistant metastatic prostate cancer comprising administering PSMA ADC in an amount effective to alleviate or decrease the level of pain in the subject. In one embodiment, the pain is bone pain. In one embodiment, the amount effective to alleviate or decrease the level of pain (e.g., bone pain) in the subject is a dose of PSMA ADC of at least 1.6 mg/kg or greater. In another embodiment, the amount effective is a dose of at least 1.8 mg·kg or greater. In yet another embodiment, the amount effective is a dose of at least 2.0 mg/kg or greater. In one embodiment, the dose is administered at 1, 2, 3 or 4 week intervals or more. In another embodiment, the dose is administered intravenously at 3 week intervals. In still other embodiments, the treatment is effective to reduce pain (e.g., bone pain) and the number of CTC cells in a subject. In yet another embodiment, the treatment is effective to reduce pain (e.g., bone pain) and PSA levels in a subject. In still other embodiments, the treatment is effective to reduce pain (e.g., bone pain), the number of CTC cells and PSA levels in a subject. In still another embodiment, the method involves increasing survival of the subject as compared to the median survival of subjects not been treated with the PSMA ADC and that have progressive, castration-resistant, metastatic prostate cancer that has progressed after prior taxane therapy. In yet another embodiment, the method involves decreasing a circulating level of circulating tumor cells (CTCs) compared to a baseline level. In a further embodiment, the method involves decreasing or stabilizing a serum level of PSA compared to a baseline level of PSA.

In yet another aspect, a method for treating a subject having progressive, castration-resistant, metastatic prostate cancer that has progressed after prior taxane therapy, comprising administering an effective amount of an antibody-drug conjugate, wherein the antibody-drug conjugate comprises a monoclonal antibody or antigen-binding fragment thereof that specifically binds to prostate-specific membrane antigen (PSMA) conjugated to monomethylauristatin norephedrine or monomethylauristatin phenylalanine, and wherein the sequence of PSMA is the sequence set forth in SEQ ID NO: 1, is also provided. In one embodiment, the PSMA antibody drug conjugate (also referred to herein as "PSMA ADC" or "ADC") consists essentially of a human monoclonal antibody to PSMA conjugated to monomethylaurastatin norephedrine (MMAE) via a valine-citrulline linker. In one embodiment, the method involves killing PSMA-expressing, taxane-resistant cancer cells. In another embodiment, the method involves delaying or inhibiting progression of the cancer. In a further embodiment, the method involves alleviating or decreasing pain in a subject (e.g., a human patient) having progressive, castration resistant, taxane-resistant metastatic prostate cancer comprising administering PSMA ADC in an amount effective to alleviate or decrease the level of pain in the subject. In one embodiment, the pain is bone pain. In one embodiment, the amount effective to alleviate or decrease the level of pain (e.g., bone pain) in the subject is a dose of PSMA ADC of at least 1.6 mg/kg or greater. In another embodiment, the amount effective is a dose of at least 1.8 mg·kg or greater. In yet another embodiment, the amount effective is a dose of at least 2.0 mg/kg or greater. In one embodiment, the dose is administered at 1, 2, 3 or 4 week intervals or more. In another embodiment, the dose is administered intravenously at 3 week intervals. In still other embodiments, the treatment is effective to reduce pain (e.g., bone pain) and the number of CTC cells in a subject. In yet another embodiment, the treatment is effective to reduce pain (e.g., bone pain) and PSA levels in a subject. In still other embodiments, the treatment is effective to reduce pain (e.g., bone pain), the number of CTC cells and PSA levels in a subject. In still another embodiment, the method involves increasing survival of the subject as compared to the median survival of subjects not been treated with the PSMA ADC and that have progressive, castration-resistant, metastatic prostate cancer that has progressed after prior taxane therapy. In yet another embodiment, the method involves decreasing a circulating level of circulating tumor cells (CTCs) compared to a baseline level. In a further embodiment, the method involves decreasing or stabilizing a serum level of PSA compared to a baseline level of PSA.

In one embodiment of the methods provided, the effective amount of the ADC is sufficient to 1) delay or inhibit progression of the cancer, 2) increase survival of the subject as compared to the median survival of subjects who have not been treated with PSMA ADC and who have progressive, castration-resistant, metastatic prostate cancer that has progressed after prior taxane therapy, 3) decrease a circulating level of circulating tumor cells (CTCs) compared to a baseline level, 4) decrease or stabilize a serum level of prostate specific antigen (PSA) compared to a baseline level of PSA; and/or 5) alleviate or decrease a level of pain (e.g., bone pain) in a subject (e.g., human patient).

In one embodiment, the killing of the PSMA-expressing, taxane-resistant cancer cells or the delay or inhibition of progression of the cancer is demonstrated by radiographic image changes in tumor burden compared to a baseline radiographic image in the subject prior to the administration of the PSMA ADC. In one embodiment, the radiographic image change is a change of at least 10%. In another embodiment, the radiographic image change is a change of at least 20%. In still another embodiment, the radiographic image change is a change of at least 30%. In yet another embodiment, the radiographic image change is a change of at least 40%. In a further embodiment, the radiographic image change is a change of at least 50%. In still a further embodiment, the radiographic image change is a change of at least 60%.

In another embodiment of the methods provided, the killing of the PSMA-expressing, taxane-resistant cancer cells or the delay or inhibition of progression of cancer is demonstrated by a change in at least one biomarker for bone metastasis and bone metabolism compared to a baseline value prior to the administration of the PSMA ADC. In one embodiment, the biomarker is N-telopeptide, bone alkaline phosphatase, osteocalcin, calcitonin, calcium, pyridinoline or deoxypyridinoline.

In still another embodiment of the methods provided, treatment with the PSMA ADC results in increased survival for the subject, wherein the survival is increased in comparison to the median survival time of subjects with PSMA-expressing, taxane-resistant cancer not treated with PSMA ADC. In one embodiment, survival in the subject is increased by four weeks. In another embodiment, survival in the subject is increased by six weeks. In still another embodiment, survival in the subject is increased by two months. In yet another embodiment, survival in the subject is increased by four months. In a further embodiment, survival in the subject is increased by six months. In another embodiment, survival in the subject is increased by eight months. In still another embodiment, survival in the subject is increased by ten months. In yet another embodiment, survival in the subject is increased by twelve months. In still another embodiment, survival in the subject is increased by fourteen months.

In yet another embodiment of the methods provided, treatment with the PSMA ADC results in an improvement in the subject's quality of life as compared to the quality of life of the subject prior to treatment with the PSMA ADC. An improvement in the subject's quality of life may include an alleviation or decrease in pain levels in the subject (e.g., human patient). The pain may be any discomfort or physical suffering. The pain may also be localized pain, but is not necessarily so. The alleviation or decrease in pain levels in a subject is any perceived lessening or elimination of pain by the subject or improvement in the subject's comfort as a result of treatment with a PSMA ADC. The lessening can be determined by assessing the level of pain in the subject at least two time points. The first time point can, in some embodiments, be at baseline, or before the administration of any PSMA ADC, while the second time point is anytime after the administration of a PSMA ADC. In other embodiments, the first time point occurs after the administration of a PSMA ADC, and the second occurs anytime subsequent to the first. In some embodiments, the first time point occurs before a particular dose of PSMA ADC, and the second occurs subsequent to that particular dose of PSMA ADC. The alleviation or decrease in pain levels in a subject can be determined by asking the subject to provide a quantification of their level of pain at one time point and comparing a quantification of their level of pain at a second time point. As an example, a subject's level of pain can be assessed by asking the subject to rate their level of pain according to the Modified Brief Pain Inventory Assessment shown below in Example 10. In some embodiments, the subject's level of pain is alleviated or decreased when the subject's reported quantification of pain for any one of (or combination of) questions 1, 2, 3 and 4 is lower at a second time point as compared to a first time point. Other methods for determining whether or not there is an alleviation or decrease in pain levels in a subject are known to those of ordinary skill in the art. As mentioned elsewhere herein, the pain may be bone pain. Generally, it is thought that bone pain is a result of metastatic prostate cancer in the bone. As used herein, "bone pain" refers to any pain a subject believes emanates from bone in the subject. The bone pain may be perceived to emanate from a particular bone or particular portion of a bone. The bone pain may also, in some embodiments, be perceived to emanate from one or more bones or one or more portions of a bone. The PSMA ADC of the present invention alleviates or decreases pain (e.g., bone pain) such that the subject has an improved quality of life, including improved ambulation.

In a further embodiment of the methods provided, the PSMA-expressing, taxane-resistant cancer cells are resistant to docetaxel or paclitaxel. In still a further embodiment of the methods provided, the PSMA-expressing, taxane-resistant cancer is resistant to docetaxel or paclitaxel.

In another embodiment of the methods provided, the PSMA-expressing, taxane-resistant cancer cells are prostate cancer cells or non-prostate cancer cells. In one embodiment, the non-prostate cancer cells are bladder cancer cells, pancreatic cancer cells, liver cancer cells, lung cancer cells, kidney cancer cells, sarcoma cells, breast cancer cells, brain cancer cells, neuroendocrine carcinoma cells, colon cancer cells, testicular cancer cells or melanoma cells.

In still another embodiment of the methods provided, the PSMA-expressing, taxane-resistant cancer is prostate cancer or non-prostate cancer. In one embodiment, the non-prostate cancer is bladder cancer, pancreatic cancer, liver cancer, lung cancer, kidney cancer, sarcoma, breast cancer, brain cancer, neuroendocrine carcinoma, colon cancer, testicular cancer or melanoma.

In a further embodiment of the methods provided, the PSMA-expressing, taxane-resistant cancer cells are of a tumor. In still a further embodiment of the methods provided, the PSMA-expressing, taxane-resistant cancer is a tumor. In one embodiment, the volume of the tumor is at least 100 mm$^3$ prior to initiation of the method using PSMA ADC. In another embodiment, the volume of the tumor is at least 200 mm$^3$. In still another embodiment, the volume of the tumor is at least 300 mm$^3$. In a further embodiment, the volume of the tumor is at least 400 mm$^3$. In still a further embodiment, the volume of the tumor is at least 500 mm$^3$. In yet another embodiment, the volume of the tumor is at least 600 mm$^3$. In still another embodiment, the volume of the tumor is at least 700 mm$^3$. In a further embodiment, the volume of the tumor is at least 800 mm$^3$. In yet a further embodiment, the volume of the tumor is at least 900 mm$^3$. In another embodiment, the volume of the tumor is at least 1000 mm$^3$. In yet another embodiment, the volume of the tumor is at least 1200 mm$^3$. In still another embodiment, the volume of the tumor is at least 1400 mm$^3$. In yet a further embodiment, the volume of the tumor is at least 1600 mm$^3$.

In another embodiment of the methods provided, treatment or contact with the PSMA ADC results in a reduction of tumor volume by at least 10% compared to the tumor volume prior to the treatment or contact with the PSMA ADC. In yet another embodiment, the volume of the tumor is reduced by at least 20%. In still another embodiment, the volume of the tumor is reduced by at least 30%. In a further embodiment, the volume of the tumor is reduced by at least 40%. In still a further embodiment, the volume of the tumor is reduced by at least 50%. In yet a further embodiment, the volume of the tumor is reduced by at least 60%. In another embodiment, the volume of the tumor is reduced by at least 70%. In still another embodiment, the volume of the tumor is reduced by at least 80%. In yet another embodiment, the volume of the tumor is reduced by at least 90%. In a further embodiment, the volume of the tumor is reduced by at least 95%. In yet a further embodiment, the tumor is eradicated.

In one embodiment, the tumor has a length of at least 5 mm prior to initiation of the method using PSMA ADC. In another embodiment, the tumor has a length of at least 6 mm. In still another embodiment, the tumor has a length of at least 7 mm. In yet another embodiment, the tumor has a length of at least 8 mm. In another embodiment, the tumor has a length of at least 9 mm. In still another embodiment, the tumor has a length of at least 10 mm. In yet another embodiment, the tumor has a length of at least 11 mm. In a further embodiment, the tumor has a length of at least 12 mm. In still a further embodiment, the tumor has a length of at least 13 mm. In still a further embodiment, the tumor has a length of at least 14 mm. In another embodiment, the tumor has a length of at least 15 mm. In yet another embodiment, the tumor has a length of at least 16 mm. In still another embodiment, the tumor has a length of at least 17 mm. In a further embodiment, the tumor has a length of at least 18 mm. In yet a further embodiment, the tumor has a length of at least 19 mm. In still a further embodiment, the tumor has a length of at least 20 mm. In another embodiment, the tumor has a length of at least 21 mm. In still another embodiment, the tumor has a length of at least 22 mm. In yet another embodiment, the tumor has a length of at least 23 mm. In a further embodiment, the tumor has a length of at least 24 mm. In still a further embodiment, the tumor has a length of at least 25 mm. In yet a further embodiment, the tumor has a length of at least 30 mm.

In another embodiment of the methods provided, treatment or contact with the PSMA ADC results in a reduction of tumor length by at least 10% compared to the tumor length prior to the treatment or contact with the PSMA ADC. In yet another embodiment, the length of the tumor is reduced by at least 20%. In still another embodiment, the length of the tumor is reduced by at least 30%. In a further embodiment, the length of the tumor is reduced by at least 40%. In still a further embodiment, the length of the tumor is reduced by at least 50%. In yet a further embodiment, the length of the tumor is reduced by at least 60%. In another embodiment, the length of the tumor is reduced by at least 70%. In still another embodiment, the length of the tumor is reduced by at least 80%. In yet another embodiment, the length of the tumor is reduced by at least 90%. In a further embodiment, the length of the tumor is reduced by at least 95%. In yet a further embodiment, the length of the tumor is reduced by at least 99%.

In a further embodiment of the methods provided, administration of the PSMA ADC to a subject results in the gain of body weight in the subject (as compared to the weight of the subject prior to administration of the PSMA ADC to the subject). The gain in body weight may result from a single administration of the PSMA ADC or a course of treatment with the PSMA ADC (i.e., more than one administration). In one embodiment, the gain is at least a 5% gain in body weight. In another embodiment, the gain is at least a 10% gain. In still another embodiment, the gain is at least a 15% gain. In still a further embodiment, the gain is at least a 20% gain. In yet another embodiment, the gain is at least a 25% gain. In a further embodiment, the gain is at least a 30% gain. In another embodiment, the gain is a 5% gain in body weight. In another embodiment, the gain is a 10% gain. In still another embodiment, the gain is a 15% gain. In still a further embodiment, the gain is a 20% gain. In yet another embodiment, the gain a 25% gain. In a further embodiment, the gain is a 30% gain.

In one embodiment of the methods provided, the PSMA-expressing, taxane-resistant cancer cells are of a metastasis. In another embodiment of the methods provided, the PSMA-expressing, taxane-resistant cancer is metastatic.

In another embodiment of the methods provided, the antibody or antigen-binding fragment thereof is conjugated to at least 2 monomethylauristatin norephedrine or monomethylauristatin phenylalanine molecules. In yet another embodiment of the methods provided, the antibody or antigen-binding fragment thereof is conjugated to at least 3 monomethylauristatin norephedrine or monomethylauristatin phenylalanine molecules. In still another embodiment of the methods provided, the antibody or antigen-binding fragment thereof is conjugated to at least 4 monomethylauristatin norephedrine or monomethylauristatin phenylalanine molecules.

In a further embodiment of the methods provided, the monomethylauristatin norephedrine or monomethylauristatin phenylalanine is conjugated to the antibody or antigen-binding fragment thereof with a compound of the formula $-A_n-Y_m-Z_m-X_n-W_n-$ wherein, A is a carboxylic acyl unit; Y is an amino acid; Z is an amino acid; X and W are each a self-immolative spacer; n is an integer of 0 or 1; and m is an integer of 0 or 1, 2, 3, 4, 5 or 6.

In one embodiment, A is

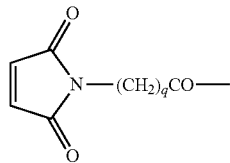

in which q is 1-10. In another embodiment, A is 4-(N-succinimidomethyl)cyclohexane-1-carbonyl, m-succinimidobenzoyl, 4-(p-succinimidophenyl)-butyryl, 4-(2-acetamido)benzoyl, 3-thiopropionyl, 4-(1-thioethyl)-benzoyl, 6-(3-thiopropionylamido)-hexanoyl or maleimide caproyl. In still another embodiment, A is maleimide caproyl.

In another embodiment, Y is alanine, valine, leucine, isoleucine, methionine, phenylalanine, tryptophan or proline. In yet another embodiment, Y is valine.

In a further embodiment, Z is lysine, lysine protected with acetyl or formyl, arginine, arginine protected with tosyl or nitro groups, histidine, ornithine, ornithine protected with acetyl or formyl, or citrulline. In yet a further embodiment, Z is citrulline.

In one embodiment, $Y_m-Z_m$ is valine-citrulline. In another embodiment, $Y_m-Z_m$ is a protein sequence which is selectively cleavable by a protease.

In still another embodiment, X is a compound having the formula

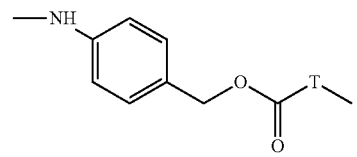

in which T is O, N, or S. In yet another embodiment, X is a compound having the formula $-HN-R^1-COT$ in which $R^1$ is $C_1-C_5$ alkyl, T is O, N or S. In a further embodiment, X is a compound having the formula

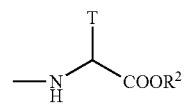

in which T is O, N, or S, $R^2$ is H or $C_1-C_5$ alkyl. In yet a further embodiment, X is p-aminobenzylcarbamoyloxy. In still a further embodiment, X is p-aminobenzylalcohol. In another embodiment, X is p-aminobenzylcarbamate. In still another embodiment, X is p-aminobenzyloxycarbonyl. In yet another embodiment, X is γ-aminobutyric acid; α,α-dimethyl γ-aminobutyric acid or β,β-dimethyl γ-aminobutyric acid.

In one embodiment, W is

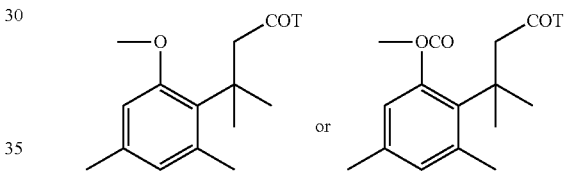

in which T is O, S or N.

In another embodiment, m and n are 0.

In still another embodiment of the methods provided, the antibody-drug conjugate is AB-PG1-XG1-006-maleimide caproyl-valine-citrulline-p-aminobenzyloxycarbonyl-monomethylauristatin norephedrine. In another embodiment of the methods provided, the antibody-drug conjugate is AB-PG1-XG1-006-maleimide caproyl-valine-citrulline-p-aminobenzylcarbamate-monomethylauristatin norephedrine. In yet another embodiment, the antibody-drug conjugate is AB-PG1-XG1-006-maleimide caproyl-valine-citrulline-p-aminobenzyloxycarbonyl-monomethylauristatin phenylalanine. In another embodiment, the antibody-drug conjugate is AB-PG1-XG1-006-maleimide caproyl-valine-citrulline-p-aminobenzylcarbamate-monomethylauristatin phenylalanine. In a further embodiment, the antibody-drug conjugate is AB-PG1-XG1-006-maleimide caproyl-monomethylauristatin phenylalanine. In still a further embodiment, the antibody-drug conjugate is AB-PG1-XG1-026-maleimide caproyl-valine-citrulline-p-aminobenzyloxycarbonyl-monomethylauristatin norephedrine. In another embodiment, the antibody-drug conjugate is AB-PG1-XG1-026-maleimide caproyl-valine-citrulline-p-aminobenzylcarbamate-monomethylauristatin norephedrine. In yet a further embodiment, the antibody-drug conjugate is AB-PG1-XG1-026-maleimide caproyl-valine-citrulline-p-aminobenzyloxycarbonyl-monomethylauristatin phenylalanine. In yet a further embodiment, the antibody-drug conjugate is AB-PG1-XG1-026-maleimide caproyl-valine-citrulline-p-aminobenzylcarbamate-monomethylauristatin phenylalanine. In another embodiment, the antibody-drug conjugate is AB-PG1-XG1-026-maleimide caproyl-monomethylauristatin phenylalanine.

In one embodiment of the methods provided, the monoclonal antibody or antigen-binding fragment thereof specifically binds to an extracellular domain of PSMA. In another embodiment, the monoclonal antibody or antigen-binding fragment thereof specifically binds to a conformational epitope of PSMA. In still another embodiment, the monoclonal antibody or antigen-binding fragment thereof binds live cells. In a further embodiment, the monoclonal antibody or antigen-binding fragment thereof does not require cell lysis to bind PSMA. In still a further embodiment, the monoclonal antibody or antigen-binding fragment thereof binds to cells of the neovasculature of a tumor.

In another embodiment of the methods provided, the antibody or antigen-binding fragment thereof competitively inhibits the specific binding of a second antibody to its target epitope on PSMA, wherein the second antibody is selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, Abgenix 4.152.1 and antibodies comprising (a) a heavy chain encoded by a nucleic acid molecule comprising the coding region or regions of a nucleotide sequence selected from the group consisting of nucleotide sequences set forth as SEQ ID NOs: 2-7, and (b) a light chain encoded by a nucleic acid molecule comprising the coding region or regions of a nucleotide sequence selected from the group consisting of nucleotide sequences set forth as SEQ ID NOs: 8-13, or (c) a heavy chain variable region encoded by a nucleic acid molecule comprising the coding region or regions of a nucleotide sequence selected from the group consisting of nucleotide sequences set forth as SEQ ID NOs: 14, 18, 22, 26 and 30, and d) a light chain variable region encoded by a nucleic acid molecule comprising the coding region or regions of a nucleotide sequence selected from the group consisting of nucleotide sequences set forth as SEQ ID NOs: 16, 20, 24, 28 and 32.

In still another embodiment of the methods provided, the antibody or antigen-binding fragment thereof binds to an epitope on PSMA defined by an antibody selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, Abgenix 4.152.1 and antibodies comprising (a) a heavy chain encoded by a nucleic acid molecule comprising the coding region or regions of a nucleotide sequence selected from the group consisting of nucleotide sequences set forth as SEQ ID NOs: 2-7, and (b) a light chain encoded by a nucleic acid molecule comprising the coding region or regions of a nucleotide sequence selected from the group consisting of nucleotide sequences set forth as SEQ ID NOs: 8-13, or (c) a heavy chain variable region encoded by a nucleic acid molecule comprising the coding region or regions of a nucleotide sequence selected from the group consisting of nucleotide sequences set forth as SEQ ID NOs: 14, 18, 22, 26 and 30, and d) a light chain variable region encoded by a nucleic acid molecule comprising the coding region or regions of a nucleotide sequence selected from the group consisting of nucleotide sequences set forth as SEQ ID NOs: 16, 20, 24, 28 and 32.

In one embodiment, the second antibody is selected from the group consisting of AB-PG1-XG1-006, AB-PG1-XG1-026 and antibodies comprising (a) a heavy chain encoded by a nucleic acid molecule comprising the coding region or regions of a nucleotide sequence selected from the group consisting of nucleotide sequences set forth as SEQ ID NOs: 2 and 3, and (b) a light chain encoded by a nucleic acid molecule comprising the coding region or regions of a nucleotide sequence selected from the group consisting of nucleotide sequences set forth as SEQ ID NOs: 8 and 9, or (c) a heavy chain variable region encoded by a nucleic acid molecule comprising the coding region or regions of a nucleotide sequence selected from the group consisting of nucleotide sequences set forth as SEQ ID NOs: 14 and 18, and d) a light chain variable region encoded by a nucleic acid molecule comprising the coding region or regions of a nucleotide sequence selected from the group consisting of nucleotide sequences set forth as SEQ ID NOs: 16 and 20. In another embodiment, the second antibody comprises (a) a heavy chain encoded by a nucleic acid molecule comprising the coding region or regions of a nucleotide sequence set forth as SEQ ID NO: 2, and (b) a light chain encoded by a nucleic acid molecule comprising the coding region or regions of a nucleotide sequence set forth as SEQ ID NO: 8, or (c) a heavy chain variable region encoded by a nucleic acid molecule comprising the coding region or regions of a nucleotide sequence set forth as SEQ ID NO: 14, and d) a light chain variable region encoded by a nucleic acid molecule comprising the coding region or regions of a nucleotide sequence set forth as SEQ ID NO: 16. In still another embodiment, the second antibody comprises (a) a heavy chain encoded by a nucleic acid molecule comprising the coding region or regions of a nucleotide sequence set forth as SEQ ID NO: 3, and (b) a light chain encoded by a nucleic acid molecule comprising the coding region or regions of a nucleotide sequence set forth as SEQ ID NO: 9, or (c) a heavy chain variable region encoded by a nucleic acid molecule comprising the coding region or regions of the nucleotide sequence set forth as SEQ ID NO: 18, and d) a light chain variable region encoded by a nucleic acid molecule comprising the coding region or regions of the nucleotide sequence set forth as SEQ ID NO: 20.

In a further embodiment of the methods provided, the antibody is encoded by a nucleic acid molecule comprising a nucleotide sequence that is at least 90% identical to a nucleotide sequence encoding an antibody selected from the group consisting of: AB-PG1-XG1-006, AB-PG1-XG1-026 and antibodies comprising (a) a heavy chain encoded by a nucleic acid molecule comprising the coding region or regions of a nucleotide sequence selected from the group consisting of nucleotide sequences set forth as SEQ ID NOs: 2 and 3, and (b) a light chain encoded by a nucleic acid molecule comprising the coding region or regions of a nucleotide sequence selected from the group consisting of nucleotide sequences set forth as SEQ ID NOs: 8 and 9, or (c) a heavy chain variable region encoded by a nucleic acid molecule comprising the coding region or regions of a nucleotide sequence selected from the group consisting of nucleotide sequences set forth as SEQ ID NOs: 14 and 18, and d) a light chain variable region encoded by a nucleic acid molecule comprising the coding region or regions of a nucleotide sequence selected from the group consisting of nucleotide sequences set forth as SEQ ID NOs: 16 and 20. In another embodiment, the antibody is encoded by a nucleic acid molecule comprising a nucleotide sequence that is at least 95% identical. In still another embodiment, the antibody is encoded by a nucleic acid molecule comprising a nucleotide sequence that is at least 97% identical. In yet another embodiment, the antibody is encoded by a nucleic acid molecule comprising a nucleotide sequence that is at least 98% identical. In a further embodiment, the antibody is encoded by a nucleic acid molecule comprising a nucleotide sequence that is at least 99% identical.

In another embodiment of the methods provided, the antibody or antigen-binding fragment thereof is selected from the group consisting of antibodies comprising (a) a heavy chain encoded by a nucleic acid molecule comprising the coding region or regions of a nucleotide sequence selected from the group consisting of nucleotide sequences set forth as SEQ ID NOs: 2 and 3, and (b) a light chain encoded by a nucleic acid molecule comprising the coding region or regions of a nucleotide sequence selected from the group consisting of nucleotide sequences set forth as SEQ ID NOs: 8 and 9, or (c) a heavy chain variable region encoded by a nucleic acid molecule comprising the coding region or regions of a nucleotide sequence selected from the group consisting of nucleotide sequences set forth as SEQ ID NOs: 14 and 18, and d) a light chain variable region encoded by a nucleic acid molecule comprising the coding region or regions of a nucleotide sequence selected from the group consisting of nucleotide sequences set forth as SEQ ID NOs: 16 and 20, and antigen-binding fragments thereof. In still another embodiment, the antibody or antigen-binding fragment thereof comprises (a) a heavy chain encoded by a nucleic acid molecule comprising the coding region or regions of a nucleotide sequence set forth as SEQ ID NO: 2, and (b) a light chain encoded by a nucleic acid molecule comprising the coding region or regions of a nucleotide sequence set forth as SEQ ID NO: 8, or (c) a heavy chain variable region encoded by a nucleic acid molecule comprising the coding region or regions of a nucleotide sequence set forth as SEQ ID NO: 14, and d) a light chain variable region encoded by a nucleic acid molecule comprising the coding region or regions of a nucleotide sequence set forth as SEQ ID NO: 16, and antigen-binding fragments thereof. In yet another embodiment, the antibody or antigen-binding fragment thereof comprises (a) a heavy chain encoded by a nucleic acid molecule comprising the coding region or regions of a nucleotide sequence set forth as SEQ ID NO: 3, and (b) a light chain encoded by a nucleic acid molecule comprising the coding region or regions of a nucleotide sequence set forth as SEQ ID NO: 9, or (c) a heavy chain variable region encoded by a nucleic acid molecule comprising the coding region or regions of the nucleotide sequence set forth as SEQ ID NO: 18, and d) a light chain variable region encoded by a nucleic acid molecule comprising the coding region or regions of the nucleotide sequence set forth as SEQ ID NO: 20, and antigen-binding fragments thereof.

In yet a further embodiment of the methods provided, the antibody or antigen-binding fragment thereof is AB-PG1-XG1-006, AB-PG1-XG1-026 or an antigen-binding fragment thereof.

In still a further embodiment of the methods provided, the human antibody is an IgG1 comprising (a) a heavy chain encoded by a nucleic acid molecule comprising the coding region or regions of a nucleotide sequence set forth as SEQ ID NO: 2, and (b) a light chain encoded by a nucleic acid molecule comprising the coding region or regions of a nucleotide sequence set forth as SEQ ID NO: 8.

In a further aspect, provided is an antibody-drug conjugate comprising an antibody, or antigen-binding fragment thereof, that specifically binds PSMA, conjugated to a dolastatin 10 derivative, for use in a method of treating a PSMA-expressing, taxane-resistant cancer. Preferably, said method involves killing PSMA-expressing, taxane-resistant cancer cells. In another embodiment, the method involves delaying or inhibiting progression of the cancer. In still another embodiment, the method involves increasing survival of the subject as compared to the median survival of subjects not been treated with the PSMA ADC and that have progressive, castration-resistant, metastatic prostate cancer that has progressed after prior taxane therapy. In yet another embodiment, the method involves decreasing a circulating level of circulating tumor cells (CTCs) compared to a baseline level. In a further embodiment, the method involves decreasing or stabilizing a serum level of PSA compared to a baseline level of PSA. It is also preferred that the PSMA-expressing, taxane-resistant cancer cells are killed by the conjugate. The PSMA preferably has the sequence set forth in SEQ ID NO: 1. The conjugate is preferably for treating progressive, castration-resistant, metastatic prostate cancer that has progressed after prior taxane therapy. The dolastatin 10 derivative can be an auristatin, and is preferably MMAE (also referred to herein as monomethylauristatin E or monomethylauristatin norephedrine) or MMAF (also referred to herein as monomethylauristatin F or monomethylauristatin phenylalanine). In preferred embodiments of this further aspect, the conjugate can have any of the features of the conjugate employed in other aspects of the invention defined herein. The method involved in this further aspect, moreover, can involve the administration of an effective amount of the conjugate, as defined with reference to other aspects defined herein. It can also have any of the features of any of the methods for treating a subject that are described herein.

BRIEF DESCRIPTION OF THE FIGURES

FIG. 6 presents a table that demonstrates the potent and specific cytotoxicity of PSMA ADC to PSMA-expressing prostate cancer cells.

DETAILED DESCRIPTION OF THE INVENTION

Figure 1:
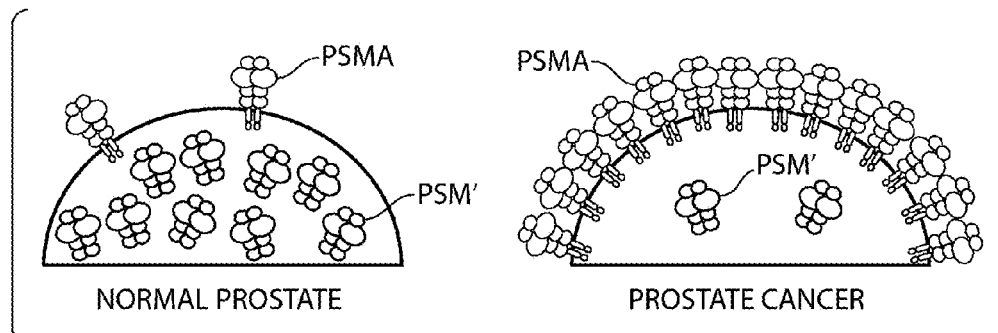
FIG. 1 presents a schematic showing the sub-cellular localization of PSMA in normal prostate versus prostate cancer. PSMA is a 750 residue, type II transmembrane glycoprotein that is highly expressed in prostate cancer cells and has limited expression in normal non-prostatic tissues. In the normal prostate, PSMA is expressed predominantly as a cytoplasmic splice variant (PSM') that is retained in the cytoplasm. In prostate cancer, PSMA is expressed as a membrane-anchored, noncovalently associated homodimer.
Figure 2:
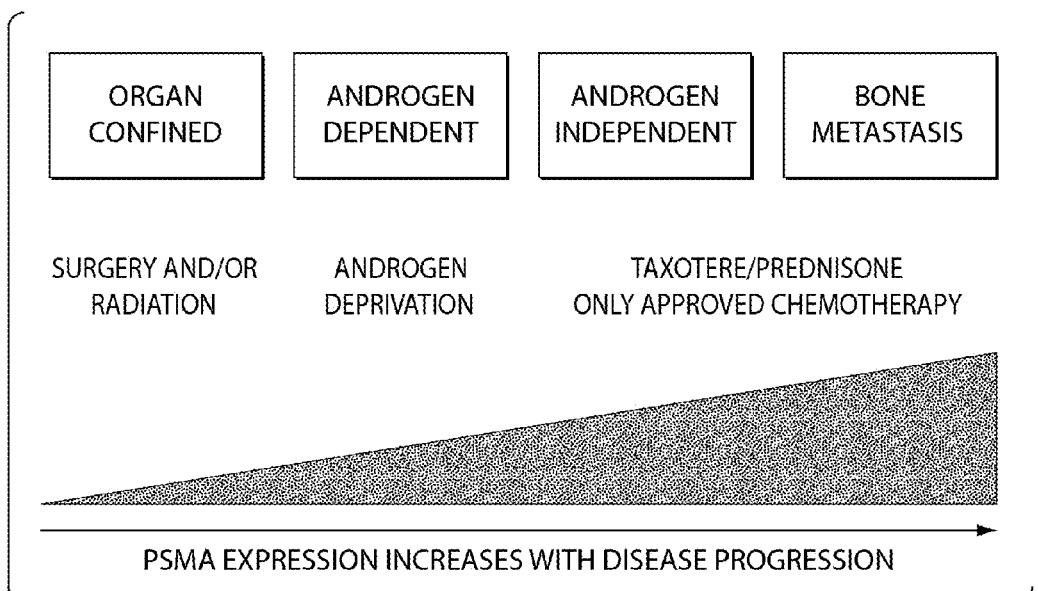
FIG. 2 presents a schematic of a number of prostate cancer treatment options. The approved chemotherapy, docetaxel (Taxotere) in combination with prednisone, for advanced prostate cancer provides a modest increase in survival (2-3 months) with significant side effects.

The present invention relates, in part, to the surprising discovery that antibody-drug conjugates (ADCs) comprising an antibody or antigen-binding fragment thereof that specifically binds PSMA conjugated to a dolastatin 10 derivative, in particular auristatins such as, MMAE (also referred to herein as monomethylauristatin E or monomethylauristatin norephedrine) or MMAF (also referred to herein as monomethylauristatin F or monomethylauristatin phenylalanine) can be used to kill PSMA-expressing, taxane-resistant cancer cells. As described further below, it was unexpectedly found that PSMA expressing cancer cells which had become resistant to the effects of an anti-cancer agent that acts by disrupting the microtubular network in cells, were sensitive to the effects of a second anti-cancer agent that also targets microtubules. Specifically disclosed herein, the auristatin, MMAE, a potent tubulin inhibitor, in the form of an antibody-drug conjugate, when delivered to PSMA-expressing prostate tumors that had become resistant to docetaxel was able to kill the docetaxel resistant cancer cells such that tumor volume was significantly decreased.

As used herein, "PSMA-expressing cancer cells" is intended to refer to cancer cells that express PSMA (e.g., human PSMA). PSMA is a 100 kD Type II membrane glycoprotein expressed in prostate tissues (Horoszewicz et al., 1987, Anticancer Res. 7:927-935; U.S. Pat. No. 5,162,504). PSMA was characterized as a type II transmembrane protein having sequence identity with the transferrin receptor (Israeli et al., 1994, *Cancer Res.* 54:1807-1811) and with NAALA-Dase activity (Carter et al., 1996, *Proc. Natl. Acad. Sci. U.S.A.* 93:749-753). More importantly, PSMA is expressed in increased amounts in prostate cancer, and elevated levels of PSMA are also detectable in the sera of these patients (Horoszewicz et al., 1987; Rochon et al., 1994, *Prostate* 25:219-223; Murphy et al., 1995, *Prostate* 26:164-168; and Murphy et al., 1995, *Anticancer Res.* 15:1473-1479). PSMA expression in cancerous prostate is approximately 10-fold greater than that in normal prostate. Expression in normal prostate is approximately 10-fold greater than that in the brain and is 50- to 100-fold greater than that of the liver or kidney. In most normal tissues, no expression of PSMA is observed. PSMA expression increases with disease progression, becoming highest in metastatic, hormone-refractory disease. In addition, PSMA is also abundantly expressed on the neovasculature of a variety of non-prostate tumors, including bladder, breast, colon, pancreas, sarcoma, melanoma, renal, liver, lung (e.g., non-small cell lung carcinoma), and kidney tumors, but not on normal vasculature. PSMA-expressing cancer cells, therefore, include, for example, prostate cancer cells as well as endothelial cells of the neovasculature of a number of non-prostate cancers.

"Taxane-resistant cancer cells" refers to cancer cells of a cancer that has been treated with a taxane but that has become resistant to treatment with the taxane (i.e., further treatment with the taxane would not slow or halt the progression of the cancer and/or would no longer provide a significant benefit to a subject with the cancer). A "subject with a taxane-resistant cancer" is one that has received prior treatment with a taxane but no longer experiences a significant benefit from further treatment with the taxane (e.g., no longer experiences a significant reduction in the number of cancer cells, in tumor volume, in tumor length, in the number of metastases and/or in other markers of disease progression and/or no longer experiences an improvement in quality of life and/or increased survival as compared to the expected survival time without further treatment with the taxane).

Therefore, in one embodiment the PSMA ADC is administered to a subject with progressive, metastatic, hormone-refractory prostate cancer resistant to taxane following prior taxane chemotherapy. In another embodiment, such subject is a human.

As used herein, "taxanes" are anti-cancer agents that interfere with or disrupt microtubule stability, formation and/or function. Such agents include paclitaxel and docetaxel as well as derivatives thereof, wherein the derivatives function against microtubules by the same mode of action as the taxanes from which they are derived.

The ADC can comprise an antibody or antigen-binding fragment thereof conjugated to the auristatin MMAE or MMAF. Auristatins are synthetic pentapeptide molecules that are structurally related to dolastatin 10, a natural product derived from a marine animal. MMAE and other auristatins act by inhibiting polymerization of tubulins, thereby preventing formation of the mitotic spindle. Apoptotic cell death is triggered when the cell cycle is arrested. The antibody or antigen-binding fragment thereof can be, in some embodiments, conjugated to MMAE or MMAF with a compound of the following formula (Formula 1): $-A_n-Y_m-Z_m-X_n-W_n-$, wherein A is a carboxylic acyl unit; Y is an amino acid; Z is an amino acid; X and W are each a self-immolative spacer; n is an integer of 0 or 1; and m is an integer of 0 or 1, 2, 3, 4, 5 or 6. The ADC, in some embodiments, is represented by the formula (Formula 2): $L-\{A_n-Y_m-Z_m-X_n-W_n-D\}_p$ wherein L is an antibody or antigen-binding fragment thereof that binds PSMA, D is MMAE or MMAF and p is an integer of 1, 2, 3, 4, 5, 6, 7 or 8. The other components are as described above. In one embodiment, the carboxylic unit "$A_n$" is linked to the antibody or antigen-binding fragment via a sulfur atom derived from the antibody or antigen-binding fragment:

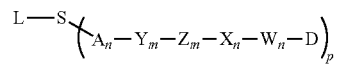

In one embodiment, A is

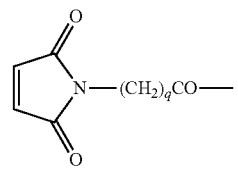

in which q is 1-10. Therefore, in one embodiment, the conjugate is:

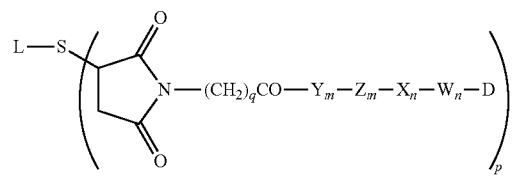

wherein L, Y, Z, X, W, D, n, m, q and p are as previously defined.

In another embodiment, A is 4-(N-succinimidomethyl)cyclohexane-1-carbonyl, m-succinimidobenzoyl, 4-(p-succinimidophenyl)-butyryl, 4-(2-acetamido)benzoyl, 3-thiopropionyl, 4-(1-thioethyl)-benzoyl, 6-(3-thiopropionylamido)-hexanoyl or maleimide caproyl. In a further embodiment, A is maleimide caproyl. Representative examples of various carboxylic acyl units and methods for their synthesis and attachment are described in U.S. Pat. No. 6,214,345, the entire contents of which, but in particular the examples and methods for their synthesis and attachment, are herein incorporated by reference.

In another embodiment, Y is alanine, valine, leucine, isoleucine, methionine, phenylalanine, tryptophan or proline. In yet another embodiment, Y is valine. In a further embodiment, Z is lysine, lysine protected with acetyl or formyl, arginine, arginine protected with tosyl or nitro groups, histidine, ornithine, ornithine protected with acetyl or formyl, or citrulline. In still a further embodiment, Z is citrulline. In one embodiment $Y_m-Z_m$ is valine-citrulline. In another embodiment, $Y_m-Z_m$ is a protein sequence which is selectively cleavable by a protease.

In a further embodiment, X is a compound having the formula

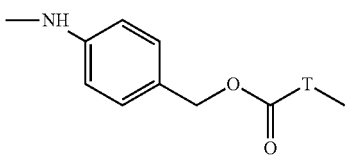

in which T is O, N, or S. In another embodiment, X is a compound having the formula —HN—R¹—COT in which R¹ is $C_1$-$C_5$ alkyl, T is O, N or S. In a further embodiment, X is a compound having the formula

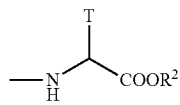

in which T is O, N, or S, $R^2$ is H or $C_1$-$C_5$ alkyl. In one embodiment, X is p-aminobenzylcarbamoyloxy. In another embodiment, X is p-aminobenzylalcohol. In a further embodiment, X is p-aminobenzylcarbamate. In yet a further embodiment, X is p-aminobenzyloxycarbonyl. In another embodiment, X is γ-aminobutyric acid; α,α-dimethyl γ-aminobutyric acid or β,β-dimethyl γ-aminobutyric acid.

In some embodiments, W is

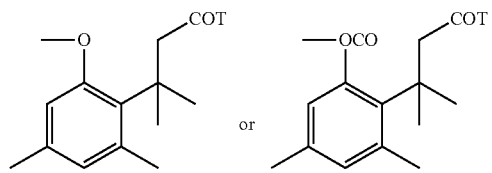

in which T is O, S or N.

In one embodiment, the compound of Formula 1 is maleimidocaproyl. Maleimidocaproyl has been used for conjugation of two specific auristatins to an anti-CD30 mAb (AC10) (Doronina, Svetlana et al. "Novel Linkers for Monoclonal Antibody-Mediated Delivery of Anticancer Agents", AACR, Anaheim, Calif., Abstract No. 1421, Apr. 16-20, 2005). Maleimidocaproyl reacts with thiol groups to form a thioether.

MMAE or MMAF can be conjugated to an antibody or antigen-binding fragment thereof using methods known to those of ordinary skill in the art (e.g., See, Niemeyer, C M, *Bioconjugation Protocols, Strategies and Methods*, Humana Press, 2004) or as described herein. In some embodiments, more than one MMAE or MMAF molecule is conjugated to the antibody or antigen-binding fragment thereof. In other embodiments, 1, 2, 3, 4, 5, 6, 7 or 8 MMAE or MMAF molecules are conjugated to the antibody or antigen-binding fragment thereof. In still other embodiments, at least 2, 3, 4 or 5 MMAE or MMAF molecules are conjugated to the antibody or antigen-binding fragment thereof. In further embodiments, 2, 3, 4 or 5 MMAE or MMAF molecules are conjugated to the antibody or antigen-binding fragment thereof.

The antibodies or antigen-binding fragments thereof of the ADCs are any antibody or antigen-binding fragment thereof that specifically binds PSMA. In one embodiment the antibody or an antigen-binding fragment thereof specifically binds PSMA (e.g., specifically binds an extracellular domain of PSMA, specifically binds a conformational epitope of PSMA, etc.) and can competitively inhibit the specific binding of a second antibody to its target epitope on PSMA, wherein the second antibody is selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, Abgenix 4.152.1 and antibodies comprising (a) a heavy chain encoded by a nucleic acid molecule comprising the coding region or regions of a nucleotide sequence selected from the group consisting of nucleotide sequences set forth as SEQ ID NOs: 2-7, and (b) a light chain encoded by a nucleic acid molecule comprising the coding region or regions of a nucleotide sequence selected from the group consisting of nucleotide sequences set forth as SEQ ID NOs: 8-13. The second antibody, therefore, include any of the antibodies produced by the hybridomas or encoded by the plasmids shown below in Table 1. These hybridomas and plasmids were deposited pursuant to, and in satisfaction of, the requirements of the Budapest Treaty on the International Recognition of the Deposit of Microorganisms for the Purposes of Patent Procedure with the American Type Culture Collection ("ATCC") as an International Depository Authority and given the Patent Deposit Designations shown above and in Table 1.

TABLE 1

| Antibody | Hybridoma/Plasmid | Patent Deposit Designation | Date of Deposit |
|---|---|---|---|
| PSMA 3.7 | PSMA 3.7 | PTA-3257 | Apr. 5, 2001 |
| PSMA 3.9 | PSMA 3.9 | PTA-3258 | Apr. 5, 2001 |
| PSMA 3.11 | PSMA 3.11 | PTA-3269 | Apr. 10, 2001 |
| PSMA 5.4 | PSMA 5.4 | PTA-3268 | Apr. 10, 2001 |
| PSMA 7.1 | PSMA 7.1 | PTA-3292 | Apr. 18, 2001 |
| PSMA 7.3 | PSMA 7.3 | PTA-3293 | Apr. 18, 2001 |
| PSMA 10.3 | PSMA 10.3 | PTA-3347 | May 1, 2001 |
|  | PSMA 10.3 HC in pcDNA (SEQ ID NO: 7) | PTA-4413 | May 29, 2002 |
|  | PSMA 10.3 Kappa in pcDNA (SEQ ID NO: 13) | PTA-4414 | May 29, 2002 |
| PSMA 1.8.3 | PSMA 1.8.3 | PTA-3906 | Dec. 5, 2001 |
| PSMA A3.1.3 | PSMA A3.1.3 | PTA-3904 | Dec. 5, 2001 |
| PSMA A3.3.1 | PSMA A3.3.1 | PTA-3905 | Dec. 5, 2001 |
| Abgenix 4.248.2 | Abgenix 4.248.2 | PTA-4427 | Jun. 4, 2002 |
| Abgenix 4.360.3 | Abgenix 4.360.3 | PTA-4428 | Jun. 4, 2002 |
| Abgenix 4.7.1 | Abgenix 4.7.1 | PTA-4429 | Jun. 4, 2002 |
| Abgenix 4.4.1 | Abgenix 4.4.1 | PTA-4556 | Jul. 18, 2002 |
| Abgenix 4.177.3 | Abgenix 4.177.3 | PTA-4557 | Jul. 18, 2002 |
| Abgenix 4.16.1 | Abgenix 4.16.1 | PTA-4357 | May 16, 2002 |
| Abgenix 4.22.3 | Abgenix 4.22.3 | PTA-4358 | May 16, 2002 |
| Abgenix 4.28.3 | Abgenix 4.28.3 | PTA-4359 | May 16, 2002 |
| Abgenix 4.40.2 | Abgenix 4.40.2 | PTA-4360 | May 16, 2002 |
| Abgenix 4.48.3 | Abgenix 4.48.3 | PTA-4361 | May 16, 2002 |
| Abgenix 4.49.1 | Abgenix 4.49.1 | PTA-4362 | May 16, 2002 |
| Abgenix 4.209.3 | Abgenix 4.209.3 | PTA-4365 | May 16, 2002 |
| Abgenix 4.219.3 | Abgenix 4.219.3 | PTA-4366 | May 16, 2002 |
| Abgenix 4.288.1 | Abgenix 4.288.1 | PTA-4367 | May 16, 2002 |
| Abgenix 4.333.1 | Abgenix 4.333.1 | PTA-4368 | May 16, 2002 |
| Abgenix 4.54.1 | Abgenix 4.54.1 | PTA-4363 | May 16, 2002 |
| Abgenix 4.153.1 | Abgenix 4.153.1 | PTA-4388 | May 23, 2002 |
| Abgenix 4.232.3 | Abgenix 4.232.3 | PTA-4389 | May 23, 2002 |
| Abgenix 4.292.3 | Abgenix 4.292.3 | PTA-4390 | May 23, 2002 |
| Abgenix 4.304.1 | Abgenix 4.304.1 | PTA-4391 | May 23, 2002 |
| AB-PG1-XG1-006 | AB-PG1-XG1-006 Heavy Chain (SEQ ID NO: 2) | PTA-4403 | May 29, 2002 |
|  | AB-PG1-XG1-006 Light Chain (SEQ ID NO: 8) | PTA-4404 |  |

TABLE 1-continued

| Antibody | Hybridoma/Plasmid | Patent Deposit Designation | Date of Deposit |
| --- | --- | --- | --- |
| AB-PG1-XG1-026 | AB-PG1-XG1-026 Heavy Chain (SEQ ID NO: 3) | PTA-4405 | May 29, 2002 |
|  | AB-PG1-XG1-026 Light Chain (SEQ ID NO: 9) | PTA-4406 |  |
| AB-PG1-XG1-051 | AB-PG1-XG1-051 Heavy Chain (SEQ ID NO: 4) | PTA-4407 | May 29, 2002 |
|  | AB-PG1-XG1-051 Light Chain (SEQ ID NO: 10) | PTA-4408 |  |
| AB-PG1-XG1-069 | AB-PG1-XG1-069 Heavy Chain (SEQ ID NO: 5) | PTA-4409 | May 29, 2002 |
|  | AB-PG1-XG1-069 Light Chain (SEQ ID NO: 11) | PTA-4410 |  |
| AB-PG1-XG1-077 | AB-PG1-XG1-077 Heavy Chain (SEQ ID NO: 6) | PTA-4411 | May 29, 2002 |
|  | AB-PG1-XG1-077 Light Chain (SEQ ID NO: 12) | PTA-4412 |  |

To determine competitive inhibition, a variety of assays known to one of ordinary skill in the art can be employed. For example, cross-competition assays can be used to determine if an antibody or antigen-binding fragment thereof competitively inhibits binding to PSMA by another antibody or antigen-binding fragment thereof. These include cell-based methods employing flow cytometry or solid phase binding analysis. Other assays that evaluate the ability of antibodies or antigen-binding fragments thereof to cross-compete for PSMA molecules that are not expressed on the surface of cells, in solid phase or in solution phase, also can be used.

In some embodiments, the antibodies or antigen-binding fragments thereof competitively inhibit the specific binding of a second antibody to its target epitope on PSMA by at least about 10%, 20%, 30%, 40%, 50%, 60%, 70%, 80%, 90%, 95%, or 99%. Inhibition can be assessed at various molar ratios or mass ratios; for example competitive binding experiments can be conducted with a 2-fold, 3-fold, 4-fold, 5-fold, 7-fold, 10-fold or more molar excess of a first antibody or antigen-binding fragment thereof over a second antibody or antigen-binding fragment thereof.

In another embodiment the antibody or an antigen-binding fragment thereof specifically binds to an epitope on PSMA defined by an antibody selected from the group consisting of PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, 4.248.2, 4.360.3, 4.7.1, 4.4.1, 4.177.3, 4.16.1, 4.22.3, 4.28.3, 4.40.2, 4.48.3, 4.49.1, 4.209.3, 4.219.3, 4.288.1, 4.333.1, 4.54.1, 4.153.1, 4.232.3, 4.292.3, 4.304.1, 4.78.1, and 4.152.1. PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, Abgenix 4.152.1 and antibodies comprising (a) a heavy chain encoded by a nucleic acid molecule comprising the coding region or regions of a nucleotide sequence selected from the group consisting of nucleotide sequences set forth as SEQ ID NOs: 2-7, and (b) a light chain encoded by a nucleic acid molecule comprising the coding region or regions of a nucleotide sequence selected from the group consisting of nucleotide sequences set forth as SEQ ID NOs: 8-13. The antibodies or antigen-binding fragments of the ADCs, therefore, include those that specifically bind to an epitope on PSMA defined by the antibodies produced by the hybridomas or encoded by the plasmids provided above in Table 1.

To determine the epitope, one can use standard epitope mapping methods known in the art. For example, fragments (peptides) of PSMA antigen (e.g., synthetic peptides) that bind the antibody can be used to determine whether a candidate antibody or antigen-binding fragment thereof binds the same epitope. For linear epitopes, overlapping peptides of a defined length (e.g., 8 or more amino acids) are synthesized. The peptides can be offset by 1 amino acid, such that a series of peptides covering every 8 amino acid fragment of the PSMA protein sequence are prepared. Fewer peptides can be prepared by using larger offsets, e.g., 2 or 3 amino acids. In addition, longer peptides (e.g., 9-, 10- or 11-mers) can be synthesized. Binding of peptides to antibodies or antigen-binding fragments can be determined using standard methodologies including surface plasmon resonance (BIACORE) and ELISA assays. For examination of conformational epitopes, larger PSMA fragments can be used. Other methods that use mass spectrometry to define conformational epitopes have been described and can be used (see, e.g., Baerga-Ortiz et al., *Protein Science* 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Peptide Combinatorial Libraries") of *Current Protocols in Immunology*, Coligan et al., eds., John Wiley & Sons. Epitopes can be confirmed by introducing point mutations or deletions into a known epitope and then testing binding with one or more antibodies or antigen-binding fragments to determine which mutations reduce binding of the antibodies or antigen-binding fragments.

In particular embodiments, the antibodies of the ADCs, or from which the antigen-binding fragments of the ADCs are derived, are those produced by hybridomas referred to herein as PSMA 3.7, PSMA 3.8, PSMA 3.9, PSMA 3.11, PSMA 5.4, PSMA 7.1, PSMA 7.3, PSMA 10.3, PSMA 1.8.3, PSMA A3.1.3, PSMA A3.3.1, Abgenix 4.248.2, Abgenix 4.360.3, Abgenix 4.7.1, Abgenix 4.4.1, Abgenix 4.177.3, Abgenix 4.16.1, Abgenix 4.22.3, Abgenix 4.28.3, Abgenix 4.40.2, Abgenix 4.48.3, Abgenix 4.49.1, Abgenix 4.209.3, Abgenix 4.219.3, Abgenix 4.288.1, Abgenix 4.333.1, Abgenix 4.54.1, Abgenix 4.153.1, Abgenix 4.232.3, Abgenix 4.292.3, Abgenix 4.304.1, Abgenix 4.78.1, and Abgenix 4.152.1, respectively. In other embodiments, the antibodies are those encoded by the plasmids listed in Table 1. In still other embodiments, the antibodies are those that comprise a heavy chain encoded by a nucleic acid molecule comprising the heavy chain coding region or regions of a nucleotide sequence selected from the group consisting of nucleotide sequences set forth as SEQ ID NOs: 2-7, and a light chain encoded by a nucleic acid molecule comprising the light chain coding region or regions of a nucleotide sequence selected from the group consisting of nucleotide sequences set forth as SEQ ID NOs: 8-13.

As used herein, the names of the deposited hybridomas or plasmids may be used interchangeably with the names of the antibodies. It will be clear to one of ordinary skill in the art when the name is intended to refer to the antibody or when it refers to the plasmids or hybridomas that encode or produce the antibodies, respectively. Additionally, the antibody names may be an abbreviated form of the name shown in Table 1. For instance, antibody AB-PG1-XG1-006 may be referred to as AB-PG1-XG1-006, PG1-XG1-006, XG1-006, 006, etc. In another example, the antibody name PSMA 4.232.3 may be referred to as PSMA 4.232.3, 4.232.1, 4.232, etc. It is intended that all of the variations in the name of the antibody refer to the same antibody and not a different one.

The antibodies of the ADCs, or from which the antigen-binding fragments of the ADCs are derived, include those encoded by particular sets of heavy and light chain sequences. In one embodiment, the antibody (AB-PG1-XG1-006) is encoded by a nucleic acid molecule which comprises the coding region or regions of the nucleic acid sequences set forth as SEQ ID NOs: 2 and 8. In another embodiment, the antibody (AB-PG1-XG1-026) is encoded by a nucleic acid molecule which comprises the coding region or regions of the nucleic acid sequences set forth as SEQ ID NOs: 3 and 9. In still another embodiment, the antibody (AB-PG1-XG1-051) is encoded by a nucleic acid molecule which comprises the coding region or regions of the nucleic acid sequences set forth as SEQ ID NOs: 4 and 10. In yet another embodiment, the antibody (AB-PG1-XG1-069) is encoded by a nucleic acid molecule which comprises the coding region or regions of the nucleic acid sequences set forth as SEQ ID NOs: 5 and 11. In another embodiment, the antibody (AB-PG1-XG1-077) is encoded by a nucleic acid molecule which comprises the coding region or regions of the nucleic acid sequences set forth as SEQ ID NOs: 6 and 12. In yet another embodiment, the antibody (PSMA 10.3) is encoded by a nucleic acid molecule which comprises the coding region or regions of the nucleic acid sequences set forth as SEQ ID NOs: 7 and 13. In other embodiments, the antibodies of the ADCs, or from which the antigen-binding fragments of the ADCs are derived, include a heavy chain variable region encoded by a nucleic acid molecule comprising the coding region or regions of a nucleotide sequence selected from the group consisting of nucleotide sequences set forth as SEQ ID NOs: 14, 18, 22, 26 and 30, and a light chain variable region encoded by a nucleic acid molecule comprising the coding region or regions of a nucleotide sequence selected from the group consisting of nucleotide sequences set forth as SEQ ID NOs: 16, 20, 24, 28 and 32. In one embodiment, the antibody (AB-PG1-XG1-006) includes an immunoglobulin variable sequence encoded by nucleic acid molecules which comprise the coding region or regions of the nucleic acid sequences set forth as SEQ ID NOs: 14 and 16. Likewise, the antibody can be one that includes an immunoglobulin variable sequence which comprises the amino acid sequences set forth as SEQ ID NOs: 15 and 17. In another embodiment, the antibody (AB-PG1-XG1-026) includes an immunoglobulin variable sequence encoded by nucleic acid molecules comprising the coding region or regions of nucleotide sequences set forth as SEQ ID NOs: 18 and 20 or includes an immunoglobulin variable sequence which comprises the amino acid sequences set forth as SEQ ID NOs 19 and 21. In still another embodiment, the antibody (AB-PG1-XG1-051) includes an immunoglobulin variable sequence encoded by the nucleic acid molecules comprising the coding region or regions of nucleotide sequences set forth as SEQ ID NOs: 22 and 24 or includes an immunoglobulin variable sequence which comprises the amino acid sequences set forth as SEQ ID NOs: 23 and 25. In yet another embodiment, the antibody (AB-PG1-XG1-069) includes an immunoglobulin variable sequence encoded by the nucleic acid molecules comprising the coding region or regions of nucleotide sequences set forth as SEQ ID NOs: 26 and 28 or includes an immunoglobulin variable sequence which comprises the amino acid sequences set forth as SEQ ID NOs: 27 and 29. In another embodiment, the antibody (AB-PG1-XG1-077) includes an immunoglobulin variable sequence encoded by the nucleic acid molecules comprising the coding region or regions of nucleotide sequences set forth as SEQ ID NOs: 30 and 32 or includes an immunoglobulin variable sequence which comprises the amino acid sequences set forth as SEQ ID NOs: 31 and 33. In other embodiments, the antibody includes a heavy chain variable region comprising an amino acid sequence selected from the group consisting of amino acid sequences set forth as: SEQ ID NOs: 15, 19, 23, 27 and 31, and a light chain variable region comprising an amino acid sequence selected from the group consisting of amino acid sequences set forth as: SEQ ID NOs: 17, 21, 25, 29 and 33.

As used herein, a "coding region" refers to a region of a nucleotide sequence that encodes a polypeptide sequence. Its use herein is consistent with the recognized meaning known in the art.

In certain embodiments, the antibodies of the ADCs, or from which the antigen-binding fragments of the ADCs are derived, are those that are encoded by nucleic acid molecules that are highly homologous to the foregoing nucleic acids. The homologous nucleic acid molecule can, in some embodiments, comprise a nucleotide sequence that is at least about 90% identical to the nucleotide sequence provided herein. In other embodiments, the nucleotide sequence is at least about 95% identical, at least about 97% identical, at least about 98% identical, or at least about 99% identical to a nucleotide sequence provided herein. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Thus, the antibodies of the ADCs, or from which the antigen-binding fragments of the ADCs are derived, include antibodies having a PSMA-binding property and/or other functional properties described herein, which are encoded by nucleic acid molecules that hybridize under high stringency conditions to the foregoing nucleic acid molecules. Identification of related sequences can also be achieved using polymerase chain reaction (PCR) and other amplification techniques suitable for cloning related nucleic acid sequences. PCR primers can be selected to amplify portions of a nucleic acid sequence of interest, such as a CDR.

The term "high stringency conditions", as used herein, refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. One example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$(pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody as used herein, refers to one or more portions of an antibody that retain the ability to specifically bind to an antigen (i.e., PSMA). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). The CDRs, and in particular the CDR3 regions, and more particularly the heavy chain CDR3 contribute to antibody specificity. Because these CDR regions and in particular the CDR3 region confer antigen specificity on the antibody, these regions may be incorporated into other antibodies or antigen-binding fragments to confer the identical antigen specificity onto that antibody or peptide. Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

The antibodies, or antigen-binding fragments thereof, of the ADCs are, in some embodiments, isolated. "Isolated", as used herein, is intended to refer to an antibody (or antigen-binding fragment thereof), which is substantially free of other antibodies (or antigen-binding fragments) having different antigenic specificities (e.g., an isolated antibody that specifically binds to PSMA is substantially free of antibodies that specifically bind antigens unrelated to PSMA). An isolated antibody that specifically binds to an epitope, isoform or variant of PSMA may, however, have cross-reactivity to other related antigens, e.g., from other species (e.g., PSMA species homologs). For example, PSMA homologs have been found in other species, such as the pig (GenBank Accession Number O77564 (amino acid)) and rat (GenBank Accession Numbers U75973 (mRNA) and AAC53423 (amino acid)). In some embodiments, the antibodies or antigen-binding fragments provided herein specifically bind both human PSMA as well as a PSMA homolog from another species. In other embodiments, the antibodies or antigen-binding fragments thereof specifically bind human PSMA but do not cross-react with PSMA homologs from another species.

Moreover, an isolated antibody (or antigen-binding fragment thereof) may be substantially free of other cellular material and/or chemicals. The term "substantially pure" means that an antibody (or antigen-binding fragment thereof) is essentially free of other substances with which they may be found in nature or in vivo systems to an extent practical and appropriate for their intended use. Substantially pure antibodies or antigen-binding fragments thereof may be produced by techniques well known in the art. Because an isolated antibody (or antigen-binding fragment thereof) may be admixed with a pharmaceutically acceptable carrier in a pharmaceutical preparation, the antibody (or antigen-binding fragment thereof) may comprise only a small percentage by weight of the preparation. The antibody (or antigen-binding fragment thereof) is nonetheless isolated in that it has been separated from the substances with which it may be associated in living systems, i.e. isolated from other proteins.

As used herein, "specific binding" refers to antibody binding to a predetermined antigen, in this case PSMA (e.g., human PSMA). Typically, the antibody binds with an affinity that is at least two-fold greater than its affinity for binding to a non-specific antigen (e.g., BSA, casein), which is an antigen other than PSMA, an isoform or variant of PSMA, or a closely-related antigen.

The antibodies encompass various antibody isotypes, such as IgG1, IgG2, IgG3, IgG4, IgM, IgA1, IgA2, IgAsec, IgD, IgE. As used herein, "isotype" refers to the antibody class (e.g., IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment and a Fv fragment.

The antibodies of the ADCs, or from which the antigen-binding fragments of the ADCs are derived, are, in some embodiments monoclonal. The antibodies can be produced by a variety of techniques well known in the art. Monoclonal antibody production may be effected by techniques which are well known in the art. The term "monoclonal antibody", as used herein, refers to a preparation of antibody molecules of single molecular composition. A monoclonal antibody displays a single binding specificity and affinity for a particular epitope. The process of monoclonal antibody production involves obtaining immune somatic cells with the potential for producing antibody, in particular B lymphocytes, which have been previously immunized with the antigen of interest either in vivo or in vitro and that are suitable for fusion with a B-cell myeloma line.

Mammalian lymphocytes typically are immunized by in vivo immunization of the animal (e.g., a mouse) with the desired protein or polypeptide. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. For example, of the BALB/c mouse. However, other mouse strains, rabbit, hamster, sheep and frog may also be used as hosts for preparing antibody-producing cells. See; Goding (in Monoclonal Antibodies: Principles and Practice, 2d ed., pp. 60-61, Orlando, Fla., Academic Press, 1986). In particular, mouse strains that have human immunoglobulin genes inserted in the genome (and which cannot produce mouse immunoglobulins) can be used. Examples include the HuMAb mouse strains produced by Medarex/GenPharm International, and the XenoMouse strains produced by Abgenix. Such mice produce fully human immunoglobulin molecules in response to immunization. In some embodiments, therefore, the ADCs comprise a fully human monoclonal antibody or an antigen-binding fragment thereof that binds PSMA.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

Alternatively, human somatic cells capable of producing antibody, specifically B lymphocytes, are suitable for fusion with myeloma cell lines. While B lymphocytes from biopsied spleens, tonsils or lymph nodes of an individual may be used, the more easily accessible peripheral blood B lymphocytes can also be used. The lymphocytes may be derived from patients with diagnosed prostate carcinomas or another PSMA-expressing to cancer. In addition, human B cells may be directly immortalized by the Epstein-Barr virus (Cole et al., 1995, Monoclonal Antibodies and Cancer Therapy, Alan R. Liss, Inc., pp. 77-96). Although somatic cell hybridization procedures can be used, in principle, other techniques for producing monoclonal antibodies can be employed such as viral or oncogenic transformation of B lymphocytes.

Myeloma cell lines suited for use in hybridoma-producing fusion procedures can be non-antibody-producing, have high fusion efficiency, and enzyme deficiencies that render them incapable of growing in certain selective media which support the growth of the desired hybridomas. Examples of such myeloma cell lines that may be used for the production of fused cell lines include P3-X63/Ag8, X63-Ag8.653, NS1/1.Ag 4.1, Sp2/0-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elseview, 1984).

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference).

In other embodiments, the antibodies of the ADCs, or from which the antigen-binding fragments of the ADCs are derived, are recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

In yet other embodiments, the antibodies are chimeric or humanized antibodies. As used herein, the term "chimeric antibody" refers to an antibody, that combines the murine variable or hypervariable regions with the human constant region or constant and variable framework regions. As used herein, the term "humanized antibody" refers to an antibody that to retains only the antigen-binding CDRs from the parent antibody in association with human framework regions (see, Waldmann, 1991, *Science* 252:1657). Such chimeric or humanized antibodies retaining binding specificity of the murine antibody are expected to have reduced immunogenicity when administered in vivo as provided herein.

According to an alternative embodiment, the monoclonal antibodies of the ADCs can be in the form of a bispecific antibody or a multispecific antibody. The term "bispecific antibody" is intended to include any agent, e.g., a protein, peptide, or protein or peptide complex, which has two different binding specificities which bind to, or interact with (a) a cell surface antigen and (b) an Fc receptor on the surface of an effector cell. The term "multispecific antibody" is intended to include any agent, e.g., a protein, peptide, or protein or peptide complex, which has more than two different binding specificities which bind to, or interact with (a) a cell surface antigen, (b) an Fc receptor on the surface of an effector cell, and (c) at least one other component. Accordingly, the antibodies include, but are not limited to, bispecific, trispecific, tetraspecific, and other multispecific antibodies which are directed to PSMA and to Fc receptors on effector cells. The term "bispecific antibodies" further includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al. (1993) *Proc. Natl. Acad. Sci. USA* 90:6444-6448; Poijak, R. J., et al. (1994) *Structure* 2:1121-1123).

A bispecific antibody can be formed of an antigen-binding region specific for PSMA and an antigen-binding region specific for an effector cell which has tumoricidal or tumor inhibitory activity. The two antigen-binding regions of the bispecific antibody are either chemically linked or can be expressed by a cell genetically engineered to produce the bispecific antibody. (See generally, Fanger et al., 1995 *Drug News & Perspec.* 8(3):133-137). Suitable effector cells having tumoricidal activity include but are not limited to cytotoxic T-cells (primarily $CD8^+$ cells), natural killer cells, etc. An effective amount of a bispecific antibody can be administered to a subject with cancer, and the bispecific antibody kills and/or inhibits proliferation of the cancer cells after localization at sites of primary or metastatic tumors bearing PSMA.

In certain embodiments, the antibodies of the ADCs, or from which the antigen-binding fragments of the ADCs are derived, are human antibodies. The term "human antibody", as used herein, is intended to include antibodies having variable and constant regions derived from human germline immunoglobulin sequences. The human antibodies can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences (referred to herein as "humanized antibodies"). Human antibodies directed against PSMA can be generated using transgenic mice carrying parts of the human immune system rather than the mouse system. Some examples of which are described elsewhere herein.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals results in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies have human immunoglobulin amino acid sequences and, therefore, will not provoke human anti-mouse antibody (HAMA) responses when administered to humans. In general, but not intended to be limiting, the mice are 6-16 weeks of age upon the first immunization. For example, a purified or enriched preparation of PSMA antigen (e.g., recombinant PSMA or PSMA-expressing cells) can be used to immunize the mice intraperitoneally (IP), although other routes of immunization known to one of ordinary skill in the art are also possible. PSMA antigen can be injected in combination with an adjuvant, such as complete Freund's adjuvant, and, in some embodiments, the initial injection is followed by booster immunizations with antigen in an adjuvant, such as incomplete Freund's adjuvant. The immune response can be monitored over the course of the immunization protocol with plasma samples obtained by, for example, retroorbital bleeds. The plasma can be screened by ELISA, and mice with sufficient titers of anti-PSMA human immunoglobulin can be used for fusions. Mice can be boosted intravenously with antigen 3 days before sacrifice and removal of the spleen.

The antibody or antigen-binding fragment thereof of the ADCs can, in some embodiments, be selected for the ability to bind live PSMA-expressing cells. In order to demonstrate binding to live PSMA-expressing cells, flow cytometry can be used. For example, PSMA-expressing cells lines (grown under standard growth conditions) or prostate cancer cells that express PSMA can be mixed with various concentrations of monoclonal antibodies in PBS containing 0.1% Tween 80 and 20% mouse serum and incubated at 37° C. for 1 hour. After washing, the cells can be reacted with fluorescein-labeled anti-human IgG secondary antibody (if human anti-PSMA antibodies were used) under the same conditions as the primary antibody staining. The samples can be analyzed by a fluorescence activated cell sorter (FACS) instrument using light and side scatter properties to gate on single cells. An alternative assay using fluorescence microscopy can be used (in addition to or instead of) the flow cytometry assay. Cells can be stained and examined by fluorescence microscopy. This method allows visualization of individual cells but may have diminished sensitivity depending on the density of the antigen. It follows, that the ADCs, in some embodiments, bind live cells. The ADCs, in some embodiments, therefore, do not require cell lysis to bind PSMA.

The antibodies can, in some embodiments, promote cytolysis of PSMA-expressing cells. Cytolysis can be complement-mediated or can be mediated by effector cells. In one embodiment, the cytolysis is carried out in a living organism, such as a mammal, and the live cell is a tumor cell. Examples of tumors which can be targeted with the antibodies or antigen-binding fragments thereof include, any tumor that expresses PSMA (this includes tumors with neovasculature expressing PSMA), such as, prostate, bladder, breast, pancreas, liver, lung (e.g., non-small cell lung carcinoma), colon and kidney tumors as well as melanomas and sarcomas. In one embodiment, the tumor cell is a prostate tumor cell.

The testing of cytolytic activity in vitro by chromium release assay can provide an initial screening prior to testing in vivo models. This testing can be carried out using standard chromium release assays. Briefly, polymorphonuclear cells (PMN), or other effector cells, from healthy donors can be purified by Ficoll Hypaque density centrifugation, followed by lysis of contaminating erythrocytes. Washed PMNs can be suspended in RPMI supplemented with 10% heat-inactivated fetal calf serum and mixed with $^{51}$Cr labeled cells expressing PSMA, at various ratios of effector cells to tumor cells (effector cells:tumor cells). Purified anti-PSMA IgGs can then be added at various concentrations. Irrelevant IgG can be used as a negative control. Assays can be carried out for 0-120 minutes at 37° C. Samples can be assayed for cytolysis by measuring $^{51}$Cr release into the culture supernatant. Anti-PSMA monoclonal antibodies and/or ADCs can also be tested in combinations with each other to determine whether cytolysis is enhanced with multiple monoclonal antibodies and/or ADCs. Antibodies that bind to PSMA and/or ADCs also can be tested in an in vivo model (e.g., in mice) to determine their efficacy in mediating cytolysis and killing of cancer cells expressing PSMA, e.g., prostate tumor cells.

The antibodies of the ADCs, or from which the antigen-binding fragments of the ADCs are derived, can be selected, for example, based on the following criteria, which are not intended to be exclusive:
1) binding to live cells expressing PSMA;
2) high affinity of binding to PSMA;
3) binding to a unique epitope on PSMA (i.e., an epitope not recognized by a previously produced antibody);
4) opsonization of cells expressing PSMA;
5) mediation of growth inhibition, phagocytosis and/or killing of cells expressing PSMA in the presence of effector cells;
6) modulation (inhibition or enhancement) of NAALA-Dase, folate hydrolase, dipeptidyl peptidase IV and/or γ-glutamyl hydrolase activities;
7) growth inhibition, cell cycle arrest and/or cytotoxicity in the absence of effector cells;
8) internalization of PSMA;
9) binding to a conformational epitope on PSMA;

10) minimal cross-reactivity with cells or tissues that do not express PSMA; and 11) preferential binding to dimeric forms of PSMA rather than monomeric forms of PSMA.

The antibodies of the ADCs, or from which the antigen-binding fragments of the ADCs are derived, can meet one or more, and possibly all, of these criteria.

In one embodiment, the antibody or antigen-binding fragment thereof binds to a conformational epitope, such as a conformational epitope within the extracellular domain of PSMA. To determine if an anti-PSMA antibody or antigen-binding fragment thereof binds to conformational epitopes, each antibody can be tested in assays using native protein (e.g., non-denaturing immunoprecipitation, flow cytometric analysis of cell surface binding) and denatured protein (e.g., Western blot, immunoprecipitation of denatured proteins). A comparison of the results will indicate whether the antibody or antigen-binding fragment thereof binds a conformational epitope. Antibodies or antigen-binding fragments thereof that bind to native protein but not denatured protein are, in some embodiments, those that bind conformational epitopes. It follows, that the ADCs, in some embodiments, bind conformational epitopes of PSMA.

In another embodiment, the antibody or antigen-binding fragment thereof binds to a dimer-specific epitope on PSMA (i.e., a conformational, dimer-specific epitope unique to the quaternary structure of dimeric PSMA). Generally, antibodies or antigen-binding fragments thereof which bind to a dimer-specific epitope preferentially bind the PSMA dimer rather than the PSMA monomer. To determine if an antibody or antigen-binding fragment thereof binds preferentially (i.e., selectively and/or specifically) to a PSMA dimer, the antibody or antigen-binding fragment thereof can be tested in assays (e.g., immunoprecipitation followed by Western blotting) using native dimeric PSMA protein and dissociated monomeric PSMA protein. A comparison of the results will indicate whether the antibody or antigen-binding fragment thereof binds preferentially to the dimer. In some embodiments, the antibodies or antigen-binding fragments thereof bind to the PSMA dimer but not to the monomeric PSMA protein. It follows, that the ADCs, in some embodiments, bind to a dimer-specific epitope on PSMA.

The ADCs provided include those that selectively bind PSMA multimers. As used herein, particularly with respect to the binding of PSMA multimers by the ADCs, "selectively binds" means that an antibody or antigen-binding fragment thereof of the ADCs preferentially binds to a PSMA protein multimer (e.g., with greater avidity, greater binding affinity) rather than to a PSMA protein monomer. In some embodiments, the ADCs of the invention bind to a PSMA protein multimer with an avidity and/or binding affinity that is 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 7-fold, 10-fold, 20-fold, 30-fold, 40-fold, 50-fold, 70-fold, 100-fold, 200-fold, 300-fold, 500-fold, 1000-fold or more than that exhibited by the ADC for a PSMA protein monomer. The ADC can, in some embodiments, selectively bind a PSMA protein multimer, and not a PSMA protein monomer, i.e., exclusively binds to a PSMA protein multimer. In some embodiments, the ADC selectively binds a PSMA protein dimer.

A PSMA protein multimer, as used herein, is a protein complex of at least two PSMA proteins or fragments thereof. The PSMA protein multimers can be composed of various combinations of full-length PSMA proteins (e.g., SEQ ID NO: 1), recombinant soluble PSMA (rsPSMA, e.g., amino acids 44-750 of SEQ ID NO: 1) and fragments of the foregoing that form multimers (i.e., that retain the protein domain required for forming dimers and/or higher order multimers of PSMA). In some embodiments, at least one of the PSMA proteins forming the multimer is a recombinant, soluble PSMA (rsPSMA) polypeptide. The PSMA protein multimers can be dimers, such as those formed from recombinant soluble PSMA protein. In one embodiment, the dimer is a rsPSMA homodimer. The PSMA protein multimers referred to herein are believed to assume a native conformation and can have such a conformation. The PSMA proteins in certain embodiments are noncovalently bound together to form the PSMA protein multimer. It has been discovered that PSMA protein noncovalently associates to form dimers under non-denaturing conditions. The PSMA protein multimers can retain the activities of PSMA. The PSMA activity may be an enzymatic activity, such as folate hydrolase activity, NAALADase activity, dipeptidyl peptidase IV activity or γ-glutamyl hydrolase activity. Methods for testing the PSMA activity of multimers are well known in the art (reviewed by O'Keefe et al. in: *Prostate Cancer: Biology, Genetics, and the New Therapeutics*, L. W. K. Chung, W. B. Isaacs and J. W. Simons (eds.) Humana Press, Totowa, N.J., 2000, pp. 307-326).

The antibody or antigen-binding fragment thereof of the ADCs can bind to and be internalized with PSMA expressed on cells. The mechanism by which the antibody or antigen-binding fragment thereof is internalized with PSMA is not critical to the practice of the methods provided herein. For example, the antibody or antigen-binding fragment thereof can induce internalization of PSMA. Alternatively, internalization of the antibody or antigen-binding fragment thereof can be the result of routine internalization of PSMA. It follows that the ADC can be internalized with PSMA expressed on cells.

The antibodies or antigen-binding fragments thereof, and, therefore, the ADCs can, in some embodiments, specifically bind cell-surface PSMA and/or rsPSMA with sub-nanomolar affinity. The binding affinities can be about $1\times10^{-9}$M or less, about $1\times10^{-10}$M or less, or about $1\times10^{-11}$M or less. In one embodiment, the binding affinity is less than about $5\times10^{-10}$M.

The antibodies or antigen-binding fragments thereof can, in some embodiments, modulate at least one enzymatic activity of PSMA. The activity can be selected from the group consisting of N-acetylated α-linked acidic dipeptidase (NAALADase), folate hydrolase, dipeptidyl dipeptidase IV, γ-glutamyl hydrolase activity and combinations thereof in vitro or in vivo. The modulation may be enhancement or inhibition of at least one enzymatic activity of PSMA.

Tissue levels of NAALADase activity can be determined by detergent solubilizing homogenizing tissues, pelleting the insoluble material by centrifugation and measuring the NAALADase activity in the remaining supernatant. Likewise, the NAALADase activity in bodily fluids can also be measured by first pelleting the cellular material by centrifugation and performing a typical enzyme assay for NAALADase activity on the supernatant. NAALADase enzyme assays have been described by Frieden, 1959, *J. Biol, Chem.*, 234:2891. In this assay, the reaction product of the NAALADase enzyme is glutamic acid. This is derived from the enzyme catalyzed cleavage of N-acetylaspartylglutamate to yield N-acetylaspartic acid and glutamic acid. Glutamic acid, in a NAD(P)$^+$ requiring step, yields 2-oxoglutarate plus NAD(P)H in a reaction catalyzed by glutamate dehydrogenase. Progress of the reaction can easily and conveniently be measured by the change in absorbance at 340 nm due to the conversion of NAD(P)$^+$ to NAD(P)H.

Folate hydrolase activity of PSMA can be measured by performing enzyme assays as described by Heston and others (e.g., *Clin. Cancer Res.* 2(9):1445-51, 1996; *Urology* 49(3A Suppl):104-12, 1997). Folate hydrolases such as PSMA remove the gamma-linked glutamates from polyglutamated folates. Folate hydrolase activity can be measured using substrates such as methotrexate tri-gamma glutamate (MTX-Glu3), methotrexate di-gamma glutamate (MTXGlu2) or pteroylpentaglutamate (PteGlu5), for example using capillary electrophoresis (see *Clin. Cancer Res.* 2(9):1445-51, 1996). Timed incubations of PSMA with polyglutamated substrates can be followed by separation and detection of hydrolysis products.

As mentioned above, the ADCs provided have surprisingly been found to kill PSMA-expressing, taxane-resistant cancer cells and can be used to treat PSMA-expressing, taxane-resistant cancer. Methods are, therefore, provided wherein an ADC is administered to a subject with a PSMA-expressing, taxane-resistant cancer. The cancer cells of the PSMA-expressing, taxane-resistant cancer, in some embodiments, can be cells of a tumor (e.g., primary malignant tumor) or cells of one or more metastases.

In some embodiments, the methods provided result in the delay or inhibition of progression of the cancer in the subject. As used herein, "delay or inhibition of progression of the cancer" is intended to refer to any slowing or halting of the progression of the cancer in the subject. A slowing or halting of the progression of the cancer includes a reduction or stabilization in the number of cancer cells, the number of tumors, and/or the number of metastases in a subject. A slowing or halting is also intended to include a reduction or stabilization in the size (e.g., length or volume) of tumors and/or size of metastases in a subject. Methods for assessing the progression of cancer in a subject will be apparent to one of ordinary skill in the art. In addition, in some embodiments, the delay or inhibition of progression of the cancer can be demonstrated by a change in at least one biomarker for bone metastasis or bone metabolism compared to a baseline value prior to treatment with the ADC in the subject. In some embodiments the biomarker is N-telopeptide, bone alkaline phosphatase, osteocalcin, calcitonin, calcium, pyridinoline or deoxypyridinoline. In further embodiments, the delay or inhibition of progression of the cancer is demonstrated by radiographic image changes in tumor burden compared to a baseline radiographic image in the subject prior to ADC treatment. Methods for assessing radiographic changes, include, for example, bone scan, computerized axial tomography (CT) scan and magnetic resonance imaging (MRI). Other methods will be well known to those of ordinary skill in the art. In some embodiments, the delay or inhibition of progression is evidenced by a radiographic image change of at least 10%, 20%, 30%, 40%, 50% or 60% or more.

Treatment with the ADCs provided can also result in the increase in survival of subjects with a PSMA-expressing, taxane-resistant cancer. In some embodiments, the survival of such a subject is increased by 4, 6, 8, 10, 12, 14, 16, 18, 20, 24, 28 or 32 weeks or more as compared to the median survival of subjects with the PSMA-expressing, taxane-resistant cancer not administered the ADC. In other embodiments, the survival is increased 4, 6, 8, 10, 12, 14, 16, 18, 20, 24, 28 or 32 weeks or more as compared to the expected survival time for the subject prior to treatment with the ADC. In other embodiments of either of the foregoing, the survival of the subject is increased by 10, 12, 14, 16, 18, 20, 22 or 24 months or more according to either comparison. In one embodiment, the subject treated with an ADC is one that has progressive, castration-resistant, metastatic prostate cancer that has progressed after prior taxane therapy, and the increase in survival of the subject is as compared to the median survival of subjects having progressive, castration-resistant, metastatic prostate cancer that has progressed after prior taxane therapy and not treated with the ADC. In another embodiment, the subject treated with an ADC is one that has progressive, castration-resistant, metastatic prostate cancer that has progressed after prior taxane therapy, and the increase in survival of the subject is as compared to the expected survival time for the subject prior to treatment with the ADC.

In other embodiments, treatment with an ADC as provided results in an increase in the quality of life for the subject as compared to the quality of life experienced by the subject prior to treatment with the ADC. As used herein "an increase in the quality of life" refers to any improvement in the subject's comfort, level of energy and/or ability to function in an activity as a result of the administration of an ADC as provided herein.

In still other embodiments, treatment with an ADC can result in a decrease in the circulating level of circulating tumor cells (CTCs) compared to a baseline level. In further embodiments, treatment with an ADC can result in a decrease or stabilization (no significant increase or decrease) in a serum level of prostate-specific antigen (PSA) compared to a baseline level of PSA. Methods for assessing the circulating level of CTCs or the serum level of PSA are well known to those of ordinary skill in the art.

It was also surprising to discover that in subjects with a PSMA-expressing, taxane-resistant cancer, a reduction in tumor volume for even very large tumors can be achieved with the administration of an ADC. Therefore, in some embodiments, the subject has a tumor with a tumor volume that is at least 100 mm$^3$, 200 mm$^3$, 300 mm$^3$, 400 mm$^3$, 500 mm$^3$, 600 mm$^3$, 700 mm$^3$, 800 mm$^3$, 900 mm$^3$, 1000 mm$^3$, 1100 mm$^3$, 1200 mm$^3$, 1300 mm$^3$, 1400 mm$^3$, 1500 mm$^3$, 1600 mm$^3$, 1700 mm$^3$, 1800 mm$^3$, 1900 mm$^3$ or 2000 mm$^3$. In some embodiments, the subject has a tumor volume that is greater than 700 mm$^3$. In other embodiments, the subject has a tumor with a length of at least 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm or 30 mm or more. In other embodiments, the tumor volume or length is reduced by at least 10%, 20%, 30%, 40%, 50%, 60%, 70%, 80%, 90%, 95%, 97% or 99% as a result of treatment with an ADC as provided herein. In a further embodiment, the tumor is eradicated. Techniques for determining the presence of a tumor and for measuring its size are well known to those of ordinary skill in the art.

In one aspect, a method for alleviating or decreasing pain in a subject (e.g., a human patient) having progressive, castration resistant, taxane-resistant metastatic prostate cancer comprising administering PSMA ADC in an amount effective to alleviate or decrease the level of pain (e.g., bone pain) in the subject, wherein the antibody-drug conjugate comprises a monoclonal antibody or antigen-binding fragment thereof that specifically binds to prostate-specific membrane antigen (PSMA) conjugated to monomethylauristatin norephedrine or monomethylauristatin phenylalanine, and wherein the sequence of PSMA is the sequence set forth in SEQ ID NO: 1, is also provided. In one embodiment, the amount effective to alleviate or decrease the level of pain (e.g., bone pain) in the subject is a dose of PSMA ADC of at least 1.6 mg/kg or greater. In another embodiment, the amount effective is a dose of at least 1.8 mg·kg or greater. In yet another embodiment, the amount effective is a dose of at least 2.0 mg/kg or greater. In one embodiment, the dose is administered at 1, 2, 3 or 4 week intervals or more. In another embodiment, the dose is administered intravenously at 3 week intervals. In still other embodiments, the treatment is effective to reduce pain (e.g., bone pain) and the number of CTC cells in a subject. In yet another embodiment, the treatment is effective to reduce pain (e.g., bone pain) and PSA levels in a subject. In still other embodiments, the treatment is effective to reduce pain (e.g., bone pain), the number of CTC cells and PSA levels in a subject.

The ADCs can be used in various in vitro and in vivo methods for effecting the aforementioned therapeutic endpoints. The methods provided can be used to kill PSMA-expressing, taxane-resistant cancer cells in vitro or in vivo. Methods are also provided for treating any PSMA-expressing, taxane-resistant cancer. Such a cancer is, for example, prostate cancer. Such a cancer can also be, for example, a cancer in which PSMA is expressed on the cells of the tumor neovasculature. An exemplary list of such cancers is provided elsewhere herein.

In some embodiments, two or more different ADCs are used in combination. In another embodiment, one or more unconjugated anti-PSMA antibodies or antigen-binding fragments thereof can be combined with one or more ADCs in a single therapy to achieve a desired therapeutic effect. As an illustration, an unconjugated anti-PSMA antibody that mediates highly effective killing of target cells in the presence of effector cells and/or that inhibits the growth of cells expressing PSMA can be used with one or more ADCs. In yet another embodiment, the ADCs can be combined with one or more additional antitumor agents, such as corticosteroids, such as prednisone or hydrocortisone; immunostimulatory agents; immunomodulators; or some combination thereof.

Antitumor agents include cytotoxic agents, chemotherapeutic agents and agents that act on tumor neovasculature. Cytotoxic agents include cytotoxic radionuclides, chemical toxins and protein toxins. The cytotoxic radionuclide or radiotherapeutic isotope can be an alpha-emitting isotope such as $^{225}$Ac, $^{211}$At, $^{212}$Bi, $^{213}$Bi, $^{212}$Pb, $^{224}$Ra or $^{223}$Ra. Alternatively, the cytotoxic radionuclide can be a beta-emitting isotope such as $^{186}$Rh, $^{188}$Rh, $^{177}$Lu, $^{90}$Y, $^{131}$I, $^{67}$Cu, $^{64}$Cu, $^{153}$Sm or $^{166}$Ho. Further, the cytotoxic radionuclide can emit Auger and low energy electrons and include the isotopes $^{125}$I, $^{123}$I or $^{77}$Br.

Suitable chemical toxins or chemotherapeutic agents include members of the enediyne family of molecules, such as calicheamicin and esperamicin. Chemical toxins can also be taken from the group consisting of methotrexate, doxorubicin, melphalan, chlorambucil, ARA-C, vindesine, mitomycin C, cis-platinum, etoposide, bleomycin and 5-fluorouracil. Other antineoplastic agents include dolastatins (U.S. Pat. Nos. 6,034,065 and 6,239,104) and derivatives thereof. Dolastatins and derivatives thereof include dolastatin 10 (dolavaline-valine-dolaisoleuine-dolaproine-dolaphenine) and the derivatives auristatin PHE (dolavaline-valine-dolaisoleuine-dolaproine-phenylalanine-methyl ester) (Pettit, G. R. et al., *Anticancer Drug Des.* 13(4):243-277, 1998; Woyke, T. et al., *Antimicrob. Agents Chemother.* 45(12):3580-3584, 2001), and aurastatin E and the like. Toxins also include poisonous lectins, plant toxins such as ricin, abrin, modeccin, botulina and diphtheria toxins. Other chemotherapeutic agents are known to those skilled in the art.

Agents that act on the tumor vasculature include tubulin-binding agents such as combrestatin A4 (Griggs et al., *Lancet Oncol.* 2:82, 2001), angiostatin and endostatin (reviewed in Rosen, *Oncologist* 5:20, 2000, incorporated by reference herein) and interferon inducible protein 10 (U.S. Pat. No. 5,994,292). A number of other antiangiogenic agents are also contemplated and include: 2ME2, Angiostatin, Angiozyme, Anti-VEGF RhuMAb, Apra (CT-2584), Avicine, Benefin, BMS275291, Carboxyamidotriazole, CC4047, CC5013, CC7085, CDC801, CGP-41251 (PKC 412), CM101, Combretastatin A-4 Prodrug, EMD 121974, Endostatin, Flavopiridol, Genistein (GCP), Green Tea Extract, IM-862, ImmTher, Interferon alpha, Interleukin-12, Iressa (ZD1839), Marimastat, Metastat (Col-3), Neovastat, Octreotide, Paclitaxel, Penicillamine, Photofrin, Photopoint, PI-88, Prinomastat (AG-3340), PTK787 (ZK22584), RO317453, Solimastat, Squalamine, SU 101, SU 5416, SU-6668, Suradista (FCE 26644), Suramin (Metaret), Tetrathiomolybdate, Thalidomide, TNP-470 and Vitaxin. Additional antiangiogenic agents are described by Kerbel, J. Clin. Oncol. 19(18s):45s-51s, 2001, which is incorporated by reference herein.

The ADCs can be administered with one or more immunostimulatory agents to induce or enhance an immune response, such as IL-2 and immunostimulatory oligonucleotides (e.g., those containing CpG motifs). Immunostimulatory agents can, in some embodiments, stimulate specific arms of the immune system, such as natural killer (NK) cells that mediate antibody-dependent cell cytotoxicity (ADCC). Immunostimulatory agents include interleukin-2, α-interferon, γ-interferon, tumor necrosis factor alpha (TNFα), immunostimulatory oligonucleotides or a combination thereof. Immunomodulators include cytokines, chemokines, adjuvants or a combination thereof. Chemokines useful in increasing immune responses include but are not limited to SLC, ELC, MIP3α, MIP3β, IP-10, MIG, and combinations thereof.

The other therapeutic agent can also be a vaccine. In some embodiments, the vaccine immunizes a subject against PSMA. Such vaccines, in some embodiments, include antigens, such as PSMA dimers, with, optionally, one or more adjuvants to induce or enhance an immune response. An adjuvant is a substance which potentiates the immune response. Adjuvants of many kinds are well known in the art. Specific examples of adjuvants include monophosphoryl lipid A (MPL, SmithKline Beecham); saponins including QS21 (SmithKline Beecham); immunostimulatory oligonucleotides (e.g., CpG oligonucleotides described by Kreig et al., *Nature* 374:546-9, 1995); incomplete Freund's adjuvant; complete Freund's adjuvant; montanide; vitamin E and various water-in-oil emulsions prepared from biodegradable oils such as squalene and/or tocopherol, Quil A, Ribi Detox, CRL-1005, L-121, and combinations thereof. Formulations, such as those described in U.S. application Ser. No. 10/976,352, are also contemplated for use as vaccines in the methods provided herein. The disclosure of such formulations are incorporated herein by reference.

The vaccines can, in some embodiments, include one or more of the isolated PSMA protein multimers described herein, such as the PSMA protein dimer. In some embodiments, a PSMA protein multimer composition contains at least about 10% PSMA protein multimer (of the total amount of PSMA protein in the composition). In other embodiments, the PSMA protein multimer composition contains at least about 20%, 30%, 40%, 50%, 60%, 70%, 75%, 80%, 85%, 90%, 95%, 99% or 99.5% PSMA protein multimer. In one embodiment, the PSMA protein multimer composition contains substantially pure PSMA protein multimer, with substantially no PSMA protein monomer. It is understood that the list of specific percentages includes by inference all of the unnamed percentages between the recited percentages.

Cytokines can also be used in vaccination protocols as a result of their lymphocyte regulatory properties. Many cytokines useful for such purposes will be known to one of ordinary skill in the art, including interleukin-2 (IL-2); IL-4; IL-5;

IL-12, which has been shown to enhance the protective effects of vaccines (see, e.g., *Science* 268: 1432-1434, 1995); GM-CSF; IL-15; IL-18; combinations thereof, and the like. Thus cytokines can be administered in conjunction with antigen, chemokines and/or adjuvants to increase an immune response.

The other therapeutic agents can be used in the methods provided in unconjugated form or in conjugated form, such as conjugated to an anti-PSMA antibody or antigen-binding fragment thereof. Coupling of one or more toxin molecules to the anti-PSMA antibody or antigen-binding fragment thereof can include many chemical mechanisms, for instance covalent binding, affinity binding, intercalation, coordinate binding and complexation.

The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In some embodiments, it is contemplated that one may wish to first derivatize the antibody, and then attach the therapeutic agent to the derivatized product. Suitable cross-linking agents for use in this manner include, for example, SPDP (N-succinimidyl-3-(2-pyridyldithio)propionate), and SMPT, 4-succinimidyl-oxycarbonyl-methyl-(2-pyridyldithio)toluene.

In addition, protein toxins can be fused to the anti-PSMA antibody or antigen-binding fragment thereof by genetic methods to form a hybrid immunotoxin fusion protein. The fusion proteins can include additional peptide sequences, such as peptide spacers which operatively attach, for example, the anti-PSMA antibody and toxin, as long as such additional sequences do not appreciably affect the targeting or toxin activities of the fusion protein. The proteins can be attached by a peptide linker or spacer, such as a glycine-serine spacer peptide, or a peptide hinge, as is well known in the art. Thus, for example, the C-terminus of an anti-PSMA antibody or antigen-binding fragment thereof can be fused to the N-terminus of the protein toxin molecule to form an immunotoxin that retains the binding properties of the anti-PSMA antibody. Other fusion arrangements will be known to one of ordinary skill in the art. To express the fusion immunotoxin, the nucleic acid encoding the fusion protein is inserted into an expression vector in accordance with standard methods, for stable expression of the fusion protein, such as in mammalian cells, such as CHO cells. The fusion protein can be isolated and purified from the cells or culture supernatant using standard methodology, such as a PSMA affinity column.

Radionuclides typically are coupled to an antibody or antigen-binding fragment thereof by chelation. For example, in the case of metallic radionuclides, a bifunctional chelator is commonly used to link the isotope to the antibody or other protein of interest. Typically, the chelator is first attached to the antibody, and the chelator-antibody conjugate is contacted with the metallic radioisotope. A number of bifunctional chelators have been developed for this purpose, including the diethylenetriamine pentaacetic acid (DTPA) series of amino acids described in U.S. Pat. Nos. 5,124,471, 5,286,850 and 5,434,287, which are incorporated herein by reference. As another example, hydroxamic acid-based bifunctional chelating agents are described in U.S. Pat. No. 5,756,825, the contents of which are incorporated herein. Another example is the chelating agent termed p-SCN-Bz-HEHA (1,4,7,10,13,16-hexaazacyclo-octadecane-N,N',N'',N''',N'''',N'''''-hexaacetic acid) (Deal et al., *J. Med. Chem.* 42:2988, 1999), which is an effective chelator of radiometals such as $^{225}$Ac. Yet another example is DOTA (1,4,7,10-tetraazacyclododecane N,N',N'',N'''-tetraacetic acid), which is a bifunctional chelating agent (see McDevitt et al., Science 294:1537-1540, 2001) that can be used in a two-step method for labeling followed by conjugation.

Other therapeutic agents also include replication-selective viruses. Replication-competent virus such as the p53 pathway targeting adenovirus mutant d11520, ONYX-015, kills tumor cells selectively (Biederer, C. et al., J. Mol. Med. 80(3): 163-175, 2002). The virus can, in some embodiments, be conjugated to PSMA antibodies or antigen-binding fragments thereof.

The methods provided can further comprise the use of other therapeutic treatment modalities. Such other treatments include surgery, radiation, cryosurgery, thermotherapy, hormone treatment, chemotherapy, vaccines and other immunotherapies.

The ADCs of the invention, such as through their antibody or antigen-binding fragment thereof, can be linked to a label. Labels include, for example, fluorescent labels, enzyme labels, radioactive labels, nuclear magnetic resonance active labels, luminescent labels or chromophore labels.

The compositions provided can include a physiologically or pharmaceutically acceptable carrier, excipient or stabilizer mixed with the ADC. In some embodiments, when a composition comprises two or more different ADCs, each of the antibodies or antigen-binding fragments thereof of the ADCs binds to a distinct conformational epitope of PSMA.

Pharmaceutical compositions can be administered in combination therapy, i.e., combined with other agents. For example, the combination therapy can include an ADC with at least one anti-tumor agent, immunomodulator, immunostimulatory agent or other conventional therapy. The other agent can be conjugated to or formed as a recombinant fusion molecule with a PSMA antibody or antigen-binding fragment thereof for directed targeting of the agent to PSMA-expressing cells. In another embodiment the other therapeutic agent can be unconjugated. Additional therapeutic agents can be administered or contacted with the PSMA-expressing cells through co-administration. "Co-administering," as used herein, refers to administering two or more therapeutic agents simultaneously as an admixture in a single composition, or sequentially, and close enough in time so that the compounds may exert an additive or even synergistic effect. In still other embodiments, an additional therapeutic agent can be administered before, during or after the administration of one or more ADCs or compositions thereof.

As used herein, "pharmaceutically acceptable carrier" or "physiologically acceptable carrier" includes any and all salts, solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). Depending on the route of administration, the active compound, can be coated in a material to protect the compound from the action of acids and other natural conditions that may inactivate the compound.

When administered, the pharmaceutical compositions are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents, such as supplementary immune potentiating agents including adjuvants, chemokines and cytokines. When used in medicine, the salts should be pharmaceutically acceptable, but non-pharmaceutically acceptable salts may conveniently be used to prepare pharmaceutically-acceptable salts thereof and are not excluded from the scope of the invention.

A salt retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

An ADC can be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; and parabens.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of the compounds, which is, in some embodiments, isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administration can be found in *Remington's Pharmaceutical Sciences*, Mack Publishing Co., Easton, Pa.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The therapeutics of the invention can be administered by any conventional route, including injection or by gradual infusion over time (e.g., the ADC in saline infused over 90 minutes). The administration may, for example, be oral, intravenous, intraperitoneal, intramuscular, intracavity, intratumor, or transdermal. When compounds containing antibodies are used therapeutically, routes of administration include intravenous and by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp. 1694-1712; incorporated by reference). Those of skill in the art can readily determine the various parameters and conditions for producing antibody aerosols without resorting to undue experimentation.

The compositions of the invention are administered in effective amounts. An "effective amount" is that amount of any of the ADCs provided herein that alone, or together with further doses and/or other therapeutic agents, produces the desired response. This can involve any of the therapeutic endpoints mentioned herein. In one embodiment, this involves only slowing the progression of the disease temporarily, although in some embodiments, it involves halting the progression of the disease permanently. In other embodiments, it involves eradicating the disease altogether. The desired therapeutic endpoint can be monitored by routine methods known to those of ordinary skill in the art. An amount that is effective can be the amount of an ADC alone which produces the desired therapeutic endpoint. An amount that is effective is also the amount of an ADC in combination with another agent that produces the desired result.

Such amounts will depend, of course, on the particular cancer being treated, the severity of the cancer, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the methods can be sterile and contain an effective amount of an ADC, alone or in combination with another agent, for producing the desired response in a unit of weight or volume suitable for administration to a patient. The response can, for example, be measured by determining the physiological effects of the ADC composition, such as a reduction in tumor volume, reduction in the size or number of metastases, an increase in survival, an improvement in quality of life and/or reduction of cancer symptoms, etc. Other assays will be known to one of ordinary skill in the art and can be employed for measuring the level of the response.

The doses of ADCs administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses can range from about 10 µg/kg to about 100,000 µg/kg. In some embodiments, the doses can range from about 0.1 mg/kg to about 20 mg/kg. In still other embodiments, the doses range from about 0.1 mg/kg to 5 mg/kg, 0.1 mg/kg to 10 mg/kg or 0.1 mg/kg to 15 mg/kg. In yet other embodiments, the doses range from about 1 mg/kg to 5 mg/kg, 5 mg/kg to 10 mg/kg, 10 mg/kg to 15 mg/kg or 15 mg/kg to 20 mg/kg. In further embodiments, the dose is about 0.1 mg/kg, 0.5 mg/kg, 1 mg/kg, 2 mg/kg, 3 mg/kg, 5 mg/kg, 7 mg/kg, 10 mg/kg, 12 mg/kg, 15 mg/kg, 17 mg/kg, 20 mg/kg, 25 mg/kg or 30 mg/kg. In a further embodiment, the dose is about 0.4 mg/kg, 0.7 mg/kg. 1.1 mg/kg, 1.6 mg/kg, 1.8 mg/kg, 2.4 mg/kg, 2.9 mg/kg, 3.0 mg/kg, 3.5 mg/kg or 4.0 mg/kg. In a further embodiment, the dose is about 0.6 mg/kg, 0.9 mg/kg, 1.2 mg/kg or 1.5 mg/kg. In another embodiment, the dose is about 1 mg/kg, 3 mg/kg, 5 mg/kg or 6 mg/kg. Based upon the composition, the dose can be delivered continuously, such as by continuous pump, or at periodic intervals. In some embodiments, when the ADC is administered intravenously, the dose is between 0.1 and 20 mg/kg or any value in between. Desired time intervals of multiple doses of a particular composition can be determined without undue experimentation by one skilled in the art. Other protocols for the administration of the compositions provided will be known to one of ordinary skill in the art, in which the dose amount, schedule of administration, site(s) of administration, mode of administration and the like vary from the foregoing. In some embodiments, subjects are administered the ADC with a dose regimen of q4d×3 or q4d×6. In one embodiment, the dose is administered intravenously. In another embodiment, the dose regimen is a single intravenous dose.

Administration of an ADC or a composition comprising an ADC to mammals other than humans, e.g., for testing purposes or veterinary therapeutic purposes, etc. is carried out under substantially the same conditions as described above.

The compositions of the present invention have in vitro and in vivo therapeutic utilities. For example, these molecules can be administered to cells in culture, e.g. in vitro or ex vivo, or in a subject, e.g., in vivo, to treat a variety of cancers as provided herein. As used herein, the term "subject" is intended to include humans and non-human animals. Non-human animals include, e.g., dogs, cats, horses, cows, pigs, mice and rats. Subjects include a human patient having a PSMA-expressing, taxane-resistant cancer. The subject, in one embodiment, has progressive, castration-resistant, metastatic prostate cancer that has been treated with taxane but has progressed. In another embodiment, the subject is one that meets the entry criteria as defined in the Examples below (e.g., Examples 5, 7 and 9).

Use of the methods provided has a number of benefits. Since the ADCs preferentially target PSMA e.g., on prostate cancer cells, other tissue can be spared. As a result, treatment with such biological agents is safer, particularly for elderly patients. Treatment according to the present invention is expected to be particularly effective, in some embodiments, because it can direct high levels of ADCs to the bone marrow and lymph nodes where cancer metastases, such as prostate cancer metastases, can predominate. Treatment in accordance with the present invention can be effectively monitored with clinical parameters such as serum prostate specific antigen and/or pathological features of a patient's cancer, including stage, Gleason score, extracapsular, seminal, vesicle or perineural invasion, positive margins, involved lymph nodes, etc. Alternatively, these parameters can be used to indicate when such treatment should be employed.

The compositions for use in the methods provided herein can be in lyophilized form or provided in an aqueous medium.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference. However, the citation of any reference is not intended to be admission that said reference is prior art.

EXAMPLES

Example 1

Potent and Specific Cytotoxicity to PSMA-Expressing Prostate Cancer Cells

Figure 5:
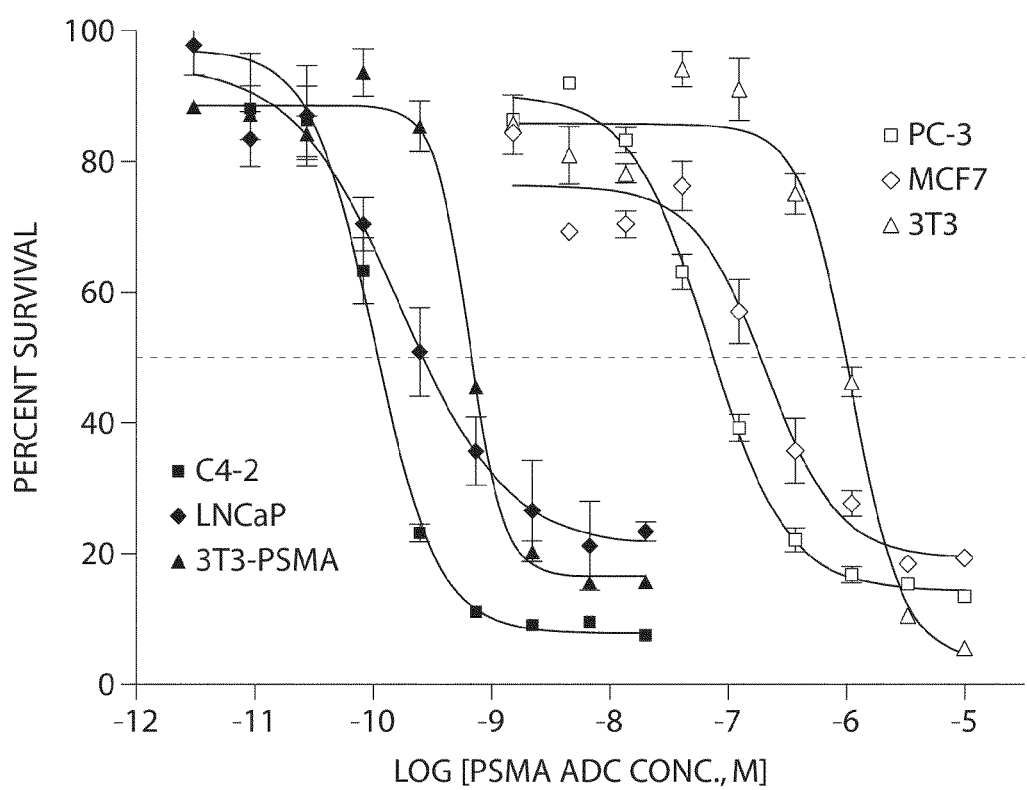
FIG. 5 demonstrates the potent and specific cytotoxicity of PSMA ADC to PSMA-expressing prostate cancer cells. PSMA-positive and PSMA-negative cells were exposed to PSMA ADC in 96-well microplates at various concentrations. After 96-hours, percent cell survival (compared to cells in medium) was assayed using fluorescent Alamar Blue.

PSMA-positive and PSMA-negative cells were exposed to PSMA ADC in 96-well microplates at various concentrations. After 96-hours, percent cell survival (compared to cells in medium) was assayed using fluorescent Alamar Blue (FIG. 5).

FIG. 6 presents a table showing cytotoxicity to PSMA-expressing prostate cancer cell lines following exposure to PSMA ADC.

Example 2

PSMA ADC is Effective to Treat Large Tumors and to Treat Docetaxel-Resistant Tumors The in vivo therapeutic efficacy of PSMA ADC in a subcutaneous xenograft model of human prostate cancer was assessed. Male athymic nude mice, 6-8 weeks old, obtained from Charles River Laboratories, Inc. (Wilmington, Mass.) were implanted subcutaneously with 5 million C4-2 cells (provided by Warren D. W. Heston of The Cleveland Clinic, Cleveland, Ohio). C4-2 is an androgen-independent human prostate cancer cell line. At day 11, the tumor size of each mouse was measured, by length and width in millimeters, using a caliper (Mitutoyo, Aurora, Ill.). The tumor volume was calculated using the following formula:

$$\text{Volume}(mm^3) = [(\text{Length}) \times (\text{Width})^2]/2$$

Animals with a tumor volume between 80-140 mm$^3$ were randomized according to tumor volume into two groups for treatment with either PBS buffer (vehicle control, n=15) or PSMA ADC (n=15). The mean tumor size was 108.9 and 108.7 mm³ with a p-value of 0.452 (student t-test) for the PBS and PSMA ADC groups, respectively, at randomization. All animals then received intravenous injections of PBS or PSMA ADC (Progenics, Tarrytown, N.Y., toxicology lot P10306) at 6 mg/kg via tail vein in a volume of 0.1 mL on day 12 through 29 twice per week for three weeks. Tumor sizes were measured twice per week or weekly for 100 days after tumor implantation, and the mean tumor volume for the two groups was plotted over time post tumor implantation (FIG. 7).

Tumor size reduction was observed in PSMA ADC treated animals. The first animal was sacrificed at day 33 in the vehicle control group due to the large size of tumor (>2000 mm³); mean tumor volume for the vehicle group and the PSMA ADC treated group were 925.7 mm³ and 92.5 mm³ (p=0.00005, student t-test), respectively. The experiment was followed for 100 days, and all mice were sacrificed except 4 animals in the PSMA ADC treated group.

Figure 7:
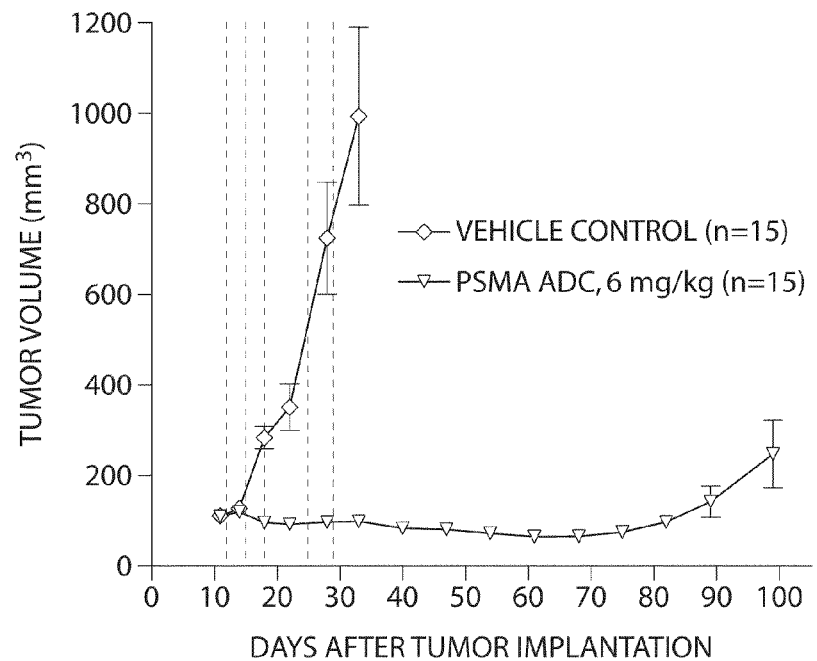
FIG. 7 shows tumor volume over time in nude mice treated with PSMA ADC versus control. Nude mice bearing human prostate cancer tumors were randomized at day 11 into two groups, PBS vehicle control (filled diamond, n=15, 108.9 mm³) and PSMA ADC (filled triangle, n=15, 108.7 mm³), according to tumor volume. The animals received intravenous injections of PBS or PSMA ADC at 6 mg/kg on day 12, 15, 18, 22, 25 and 29. The mean tumor volume was plotted for the PBS vehicle control group until the first animal was sacrificed at day 33 due to tumor size limitation (>2000 mm³).
Figure 8:
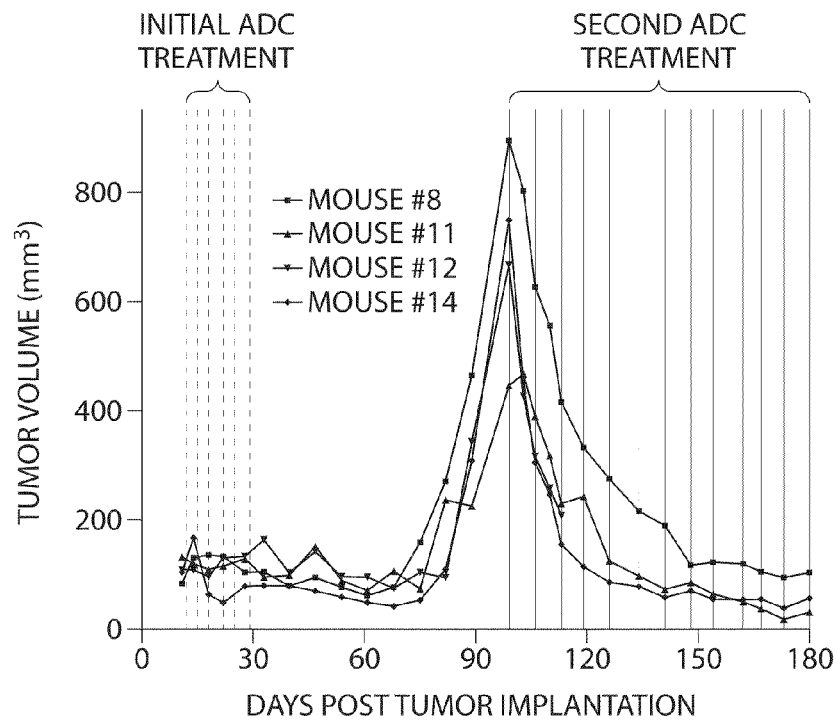
FIG. 8 shows the effect of PSMA ADC treatment on tumor volume with an initial and second PSMA ADC treatment. Tumors of four mice from the PSMA ADC treatment group were grown back and were treated with PSMA ADC at the same dose level of 6 mg/kg. PSMA ADC effectively reduced the tumor volume to <100 mm³ from large tumor of 894 mm³. The dotted lines indicate initial PSMA ADC treatment (6 dosings twice per week), and the solid lines show second PSMA ADC treatment (13 weekly dosings).
Figure 9:
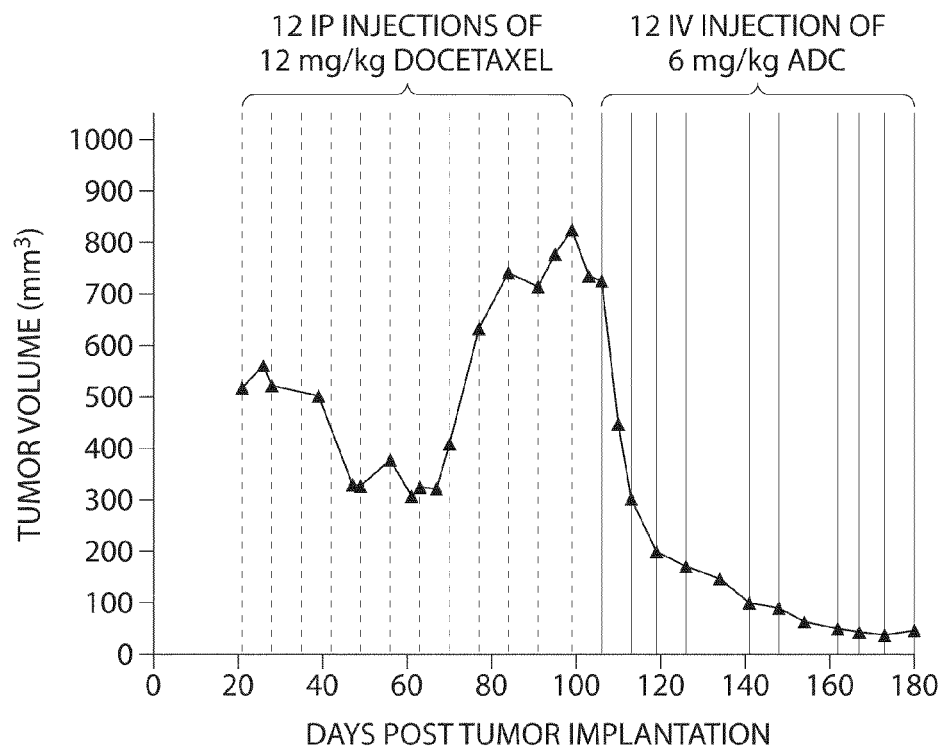
FIG. 9 demonstrates the effects in a nude mouse having a tumor size of ~500 mm³ and treated with 12 doses of docetaxel given intraperitoneally (IP) at 12 mg/kg weekly as indicated by dotted lines. The tumor responded to the docetaxel initially and then relapsed. Starting at day 100 with tumor volume of 800 mm³, PSMA ADC was given intravenously (IV) at 6 mg/kg for an additional 12 doses weekly (solid lines). PSMA ADC reduced the tumor volume from 800 mm³ to 50 mm³.

Among the 15 animals in the PSMA ADC treated group with a mean tumor size of 72.5 mm³ at day 75 as shown in FIG. 7, there were 4 mice (mouse #8, 11, 12 and 14) with tumors that started to grow at day 75 (FIG. 8). On day 99, the average tumor volume was 688.7 mm³ (893.8, 445.3, 666.7, 749.0 mm³) for the 4 mice. The animals were treated again with PSMA ADC at 6 mg/kg from day 99, once a week for 13 weeks. FIG. 8 shows the tumor volume over 180 days for the 4 mice. The dotted lines indicate initial PSMA ADC treatment, and the solid lines indicate second PSMA ADC treatment. Tumor size reduction was observed immediately in all 4 mice after the second PSMA ADC treatment, and the tumor volume continued to shrink while dosing. At day 180, the tumor volume was reduced to <100 mm³ with a mean volume of 50 mm³.

These results show that PSMA ADC is effective to treat large-sized tumors (~900 mm³) and also can be used to treat relapsed tumors using the same dose level from an initial PSMA ADC treatment.

Figure 3:
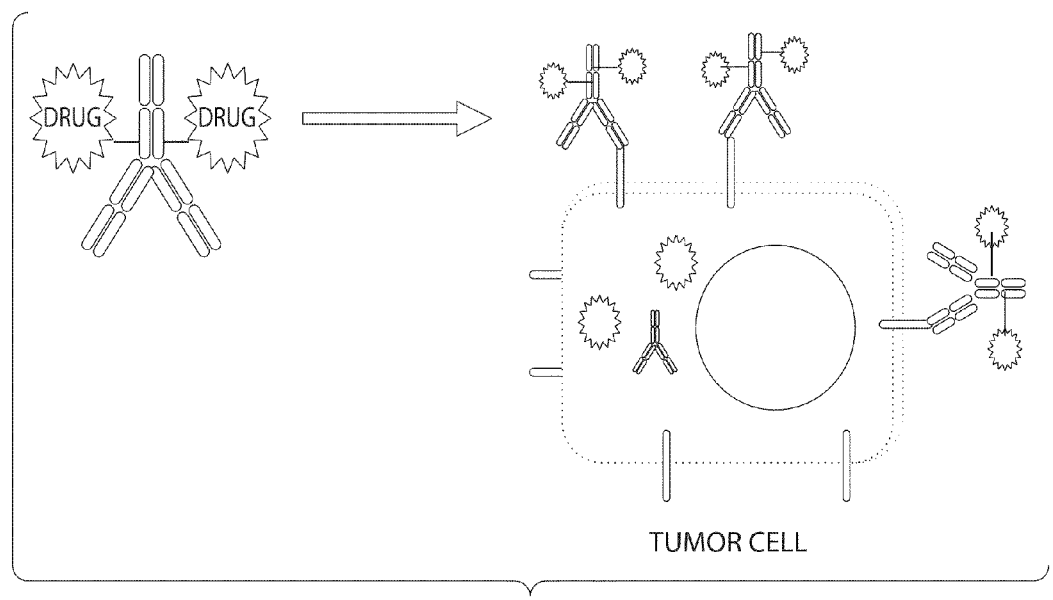
FIG. 3 presents a schematic showing antibody-drug conjugate (ADC) targeted therapy.
Figure 4:
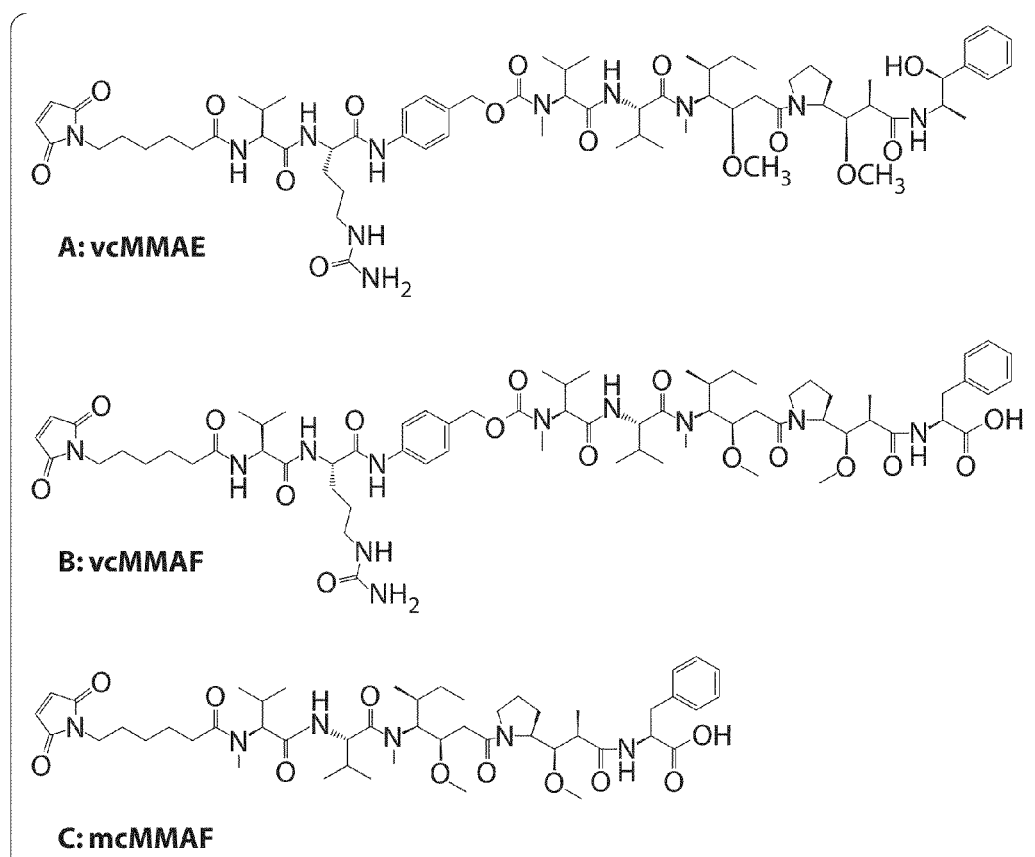
FIG. 4 provides the chemical structures of three examples of drug linkers that can be conjugated to an antibody or antigen-binding fragment thereof that specifically binds PSMA and form an antibody-drug conjugate.

One mouse that was not included in the PSMA ADC experiment described above had a tumor size of ~500 mm³ at day 21. It was given 12 doses of docetaxel, IP, at 12 mg/kg weekly. As shown in FIG. 3 and Table 2, the animal initially responded to the docetaxel treatment, the tumor volume was reduced to ~300 mm³ at day 60, but then it progressed to ~800 mm³ at day 100. The treatment of docetaxel was stopped, and PSMA ADC was given IV at 6 mg/kg for an additional 12 doses, weekly. The tumor volume was drastically reduced from 800 mm³ to ~50 mm³ at day 180 when PSMA ADC was given. PSMA ADC can treat tumors that fail docetaxel treatment.

TABLE 2

Measurement of tumor over time in an animal treated with 12 doses of 12 mg/kg docetaxel followed by 12 doses of 6 mg/kg PSMA ADC. The tumor responded to docetaxel treatment initially and then relapsed. The treatment was switched to PSMA ADC and then significant tumor volume reduction was observed.

| Days post tumor implantation | Tumor Length (mm) | Width (mm) | Volume (mm³) |
|---|---|---|---|
| 21 | 12.22 | 9.22 | 519.4 |
| 26 | 13.07 | 9.27 | 561.6 |
| 28 | 12.61 | 9.11 | 523.3 |
| 39 | 12.06 | 9.14 | 503.7 |
| 47 | 10.89 | 7.80 | 331.3 |
| 49 | 11.17 | 7.67 | 328.6 |
| 56 | 11.10 | 8.26 | 378.7 |
| 61 | 11.16 | 7.44 | 308.9 |
| 63 | 10.59 | 7.84 | 325.5 |
| 67 | 11.67 | 7.46 | 324.7 |
| 70 | 12.48 | 8.12 | 411.4 |
| 77 | 13.30 | 9.77 | 634.8 |
| 84 | 13.77 | 10.39 | 743.3 |
| 91 | 14.09 | 10.08 | 715.8 |
| 95 | 14.70 | 10.30 | 779.8 |
| 99 | 14.51 | 10.67 | 826.0 |
| 103 | 13.62 | 10.40 | 736.6 |
| 106 | 14.13 | 10.14 | 726.4 |
| 110 | 12.70 | 8.42 | 450.2 |
| 113 | 9.61 | 7.96 | 304.5 |
| 119 | 8.78 | 6.77 | 201.2 |
| 126 | 8.67 | 6.33 | 173.7 |
| 134 | 7.12 | 6.46 | 148.6 |
| 141 | 6.20 | 5.70 | 100.7 |
| 148 | 6.46 | 5.32 | 91.4 |
| 154 | 5.65 | 4.78 | 64.5 |
| 162 | 5.60 | 4.30 | 51.8 |
| 167 | 5.70 | 4.00 | 45.6 |
| 173 | 5.50 | 3.80 | 39.7 |
| 180 | 5.60 | 4.15 | 48.2 |

Example 3

Figure 10:
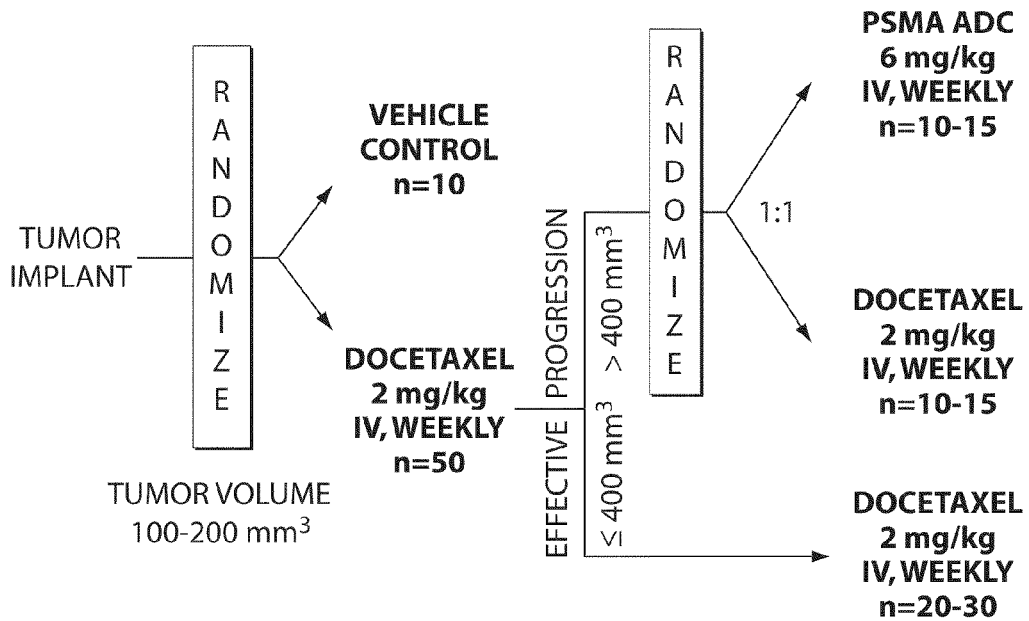
FIG. 10 shows a scheme of randomization for testing PSMA ADC effectiveness after docetaxel treatment failure. At the first randomization, the animals were assigned to vehicle control group or docetaxel treatment group. If tumor volume exceeded 400 mm³ in the docetaxel treated group, the animals were randomized (the second randomization) at a 1:1 ratio to two subgroups: continued docetaxel treatment or PSMA ADC treatment. The tumor volumes of the animals were measured over time.

PSMA ADC is Effective to Treat Tumors in Animals Which Failed Docetaxel Treatment An experiment (FIG. 10) was designed to evaluate PSMA ADC effectiveness after docetaxel treatment failure. Male athymic nude mice, 6-8 weeks old, obtained from Charles River Laboratories, Inc. were implanted subcutaneously with 5 million C4-2 cells. At day 14, animals having a tumor volume between 100-200 mm³ were randomized (randomization #1) into two treatment arms: (1) vehicle control (PBS buffer, n=10); (2) docetaxel at 2 mg/kg/IV weekly (n=50) according to tumor volume. The mean tumor volume was 138.0 and 138.1 mm$^3$ for the vehicle control and docetaxel treatment groups, respectively, at randomization.

Figure 11:
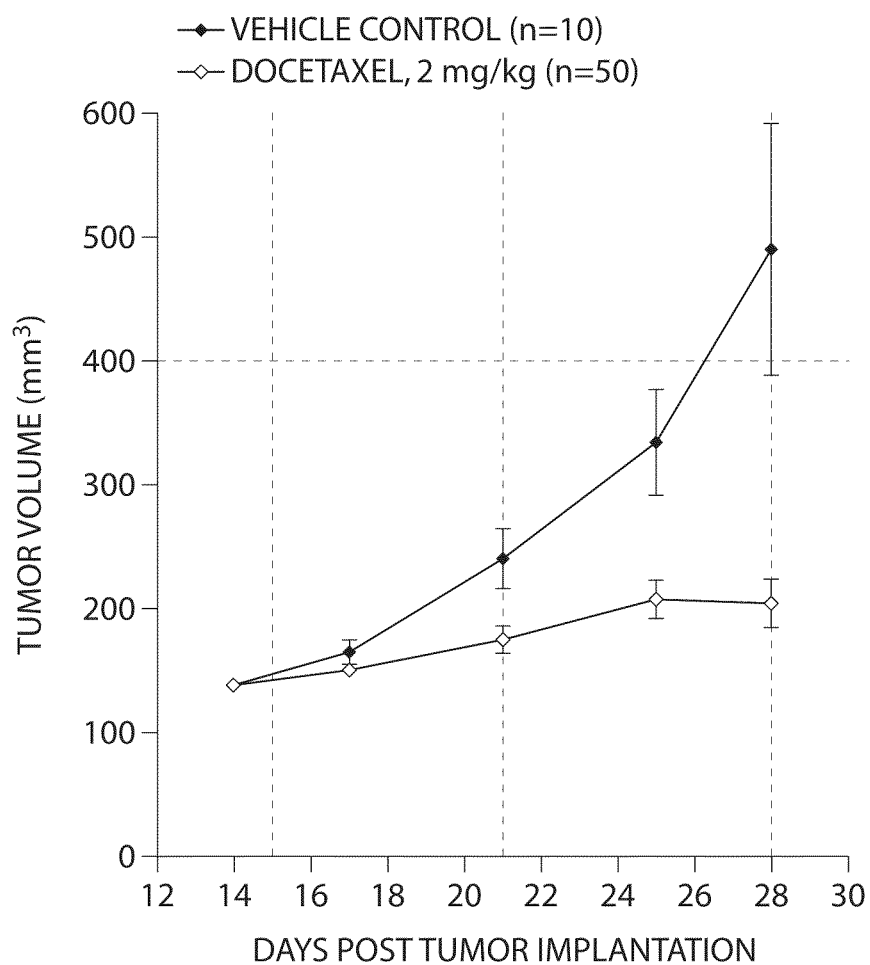
FIG. 11 shows the tumor volume over time in nude mice treated with docetaxel versus control. Nude mice bearing human prostate cancer tumors were randomized at day 14 according to tumor volume into two groups, vehicle control (filled diamond, n=10) and docetaxel (filled circle, n=50). The animals received intravenous injections of PBS or docetaxel at 2 mg/kg/IV weekly. The average tumor volume for the two groups was plotted until the second randomization was initiated. Docetaxel treatment reduced tumor growth compared to control at least by day 21 (p=0.025) and beyond.

All animals then received intravenous injections of PBS or docetaxel (Sigma, St. Louis, Mo.) at 2 mg/kg via tail vein in a volume of 0.1 mL. Tumor sizes were measured twice per week after tumor implantation, and the average tumor volume for the two groups before the second randomization was initiated were plotted (FIG. 11). Overall, docetaxel treatment reduced tumor growth compared to control.

When the tumor volume of an animal in the docetaxel treatment group exceeded 400 mm$^3$, this animal was randomized, at a 1:1 ratio, into one of the two treatment subgroups: one group continued to receive docetaxel at 2 mg/kg, and the second group was switched to PSMA ADC treatment at 6 mg/kg/IV weekly. Animals were randomized into these two treatment subgroups continuously over the period of 28 days to 70 days post tumor implantation. By the end of day 70, there were 28 mice whose tumor volume had exceeded 400 mm$^3$, with 14 mice randomized into the PSMA ADC treatment subgroup (mean tumor volume of 695 mm$^3$ and 14 mice randomized into the continued docetaxel treatment subgroup (mean tumor volume of 642 mm$^3$ with a p-value of 0.28 (student t-test)).

Figure 12:
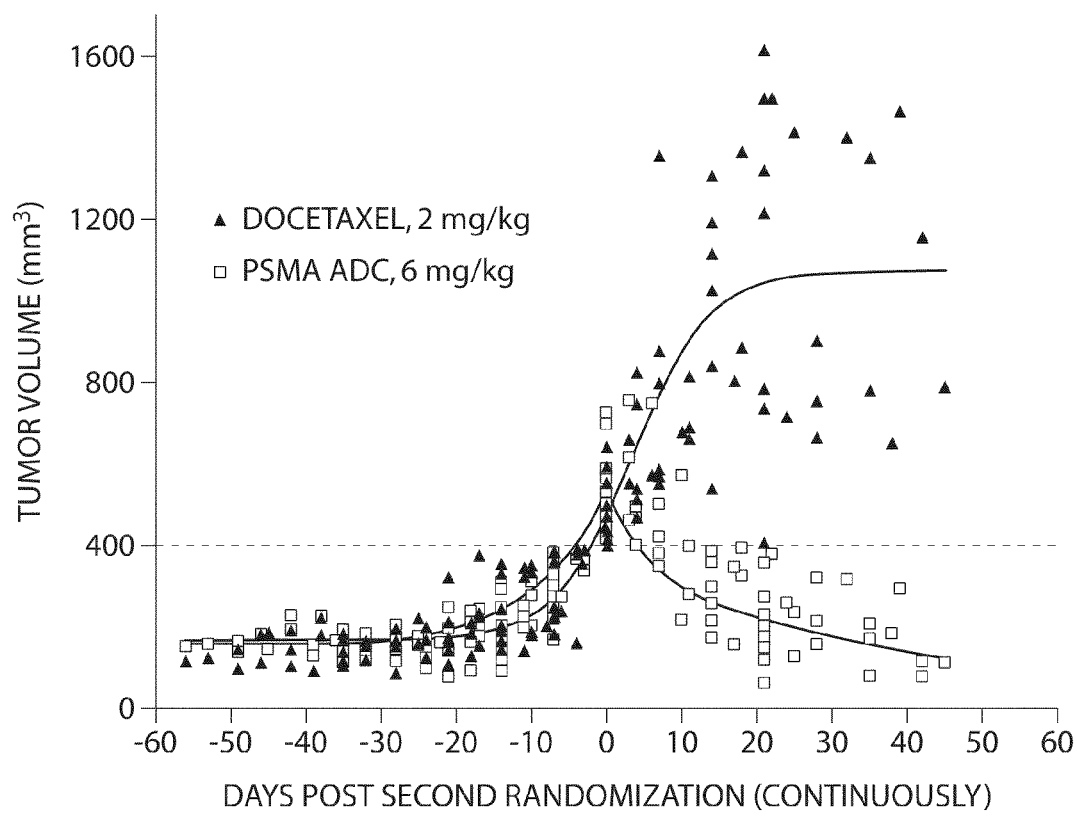
FIG. 12 shows the comparison of tumor volume in two subgroups after failure of initial docetaxel treatment: (1) continued docetaxel treatment, filled triangle, (2) PSMA ADC treatment, 6 mg/kg, filled squares. Since the mice were assigned to different groups at different times, time of treatment (days post second randomization) was aligned at day 0 (initiation of PSMA ADC or continuation of docetaxel post second randomization).

The effect of PSMA ADC treatment on tumor growth after docetaxel failure was assessed by comparing tumor reduction after the second randomization. The tumor volumes of animals in the two subgroups were plotted (FIG. 12). The results show that tumors grew continuously while on docetaxel treatment. However, the tumor volume was significantly reduced when PSMA ADC treatment was initiated. Therefore, PSMA ADC is effective in treating animals with tumors which failed docetaxel treatment.

Example 4

In Vivo Study Design

Figure 13:
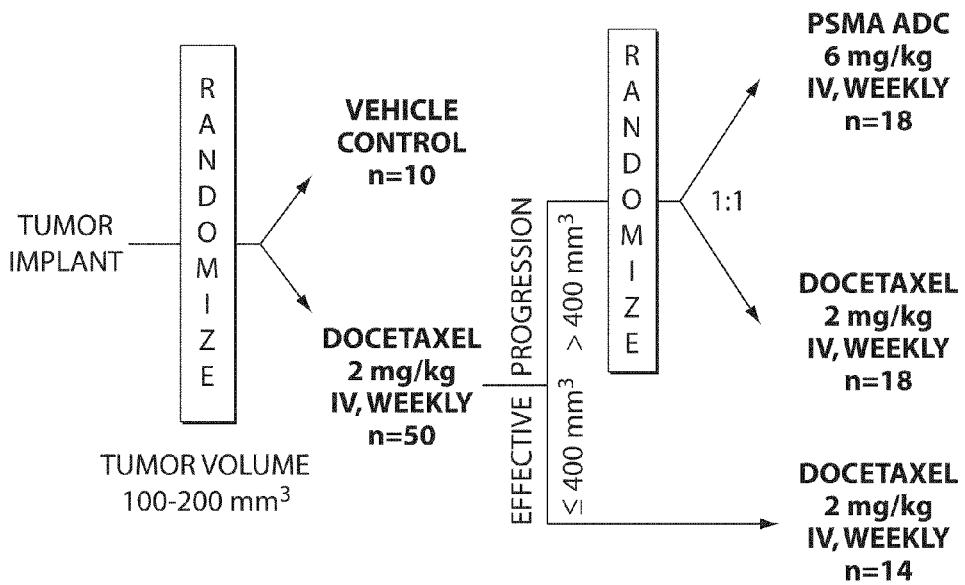
FIG. 13 shows a schematic of the design of an in vivo study.

The study design is shown in FIG. 13. Male athymic nude mice, 6-8 weeks old, obtained from Charles River Laboratories, Inc., were implanted with Matrigel subcutaneously into the right flank of each mouse with 5 million C4-2 cells (androgen-independent human prostate cancer cell line). At day 14, tumor size was measured by length and width in mm (millimeter). The volume was calculated using the formula: volume (mm$^3$)=[(length)×(width)$^2$]/2. The animals were randomized into two groups with similar tumor volume (approximately 138 mm$^3$): vehicle control and docetaxel at 2 mg/kg. Animals were dosed weekly through the tail vein.

When the tumor volume of an animal in the docetaxel treatment group exceeded 400 mm$^3$, this animal was randomized, at a 1:1 ratio, into one of the two treatment subgroups: one group continued to receive docetaxel at 2 mg/kg weekly (n=18), and the second group was switched to PSMA ADC treatment at 6 mg/kg/IV weekly (n=18). Mice whose tumors durably responded to docetaxel (≤400 mm$^3$) continued to receive docetaxel at 2 mg/kg/IV weekly. Treatment effects were assessed by measuring tumor volume and overall survival. Animal body weight was also measured. Animals with tumor size ≥2000 mm$^3$ were sacrificed.

Figure 14:
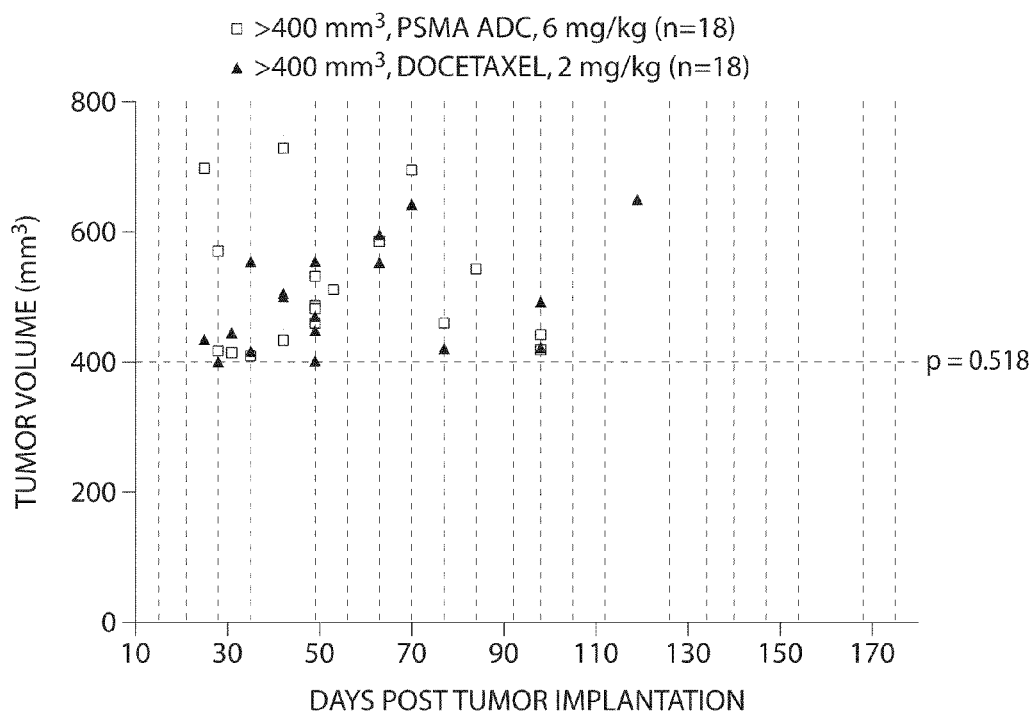
FIG. 14 shows the tumor volume of each animal. When the tumor volume of an animal in the docetaxel-treated group exceeded 400 mm³, the animal was randomized at a 1:1 ratio into two subgroups: 1) switched to PSMA ADC treatment at 6 mg/kg/IV weekly (solid squares, mean: 515±103 mm³, range 410-727 mm³) and 2) continued treatment with docetaxel at 2 mg/kg (filled triangles, mean: 495±80 mm³, range: 401-650 mm³) The tumor size of each animal and time of randomization are shown. Tumor volumes at the second randomization were not significantly different between the two groups (p=0.518, t-test).
Figure 15A:
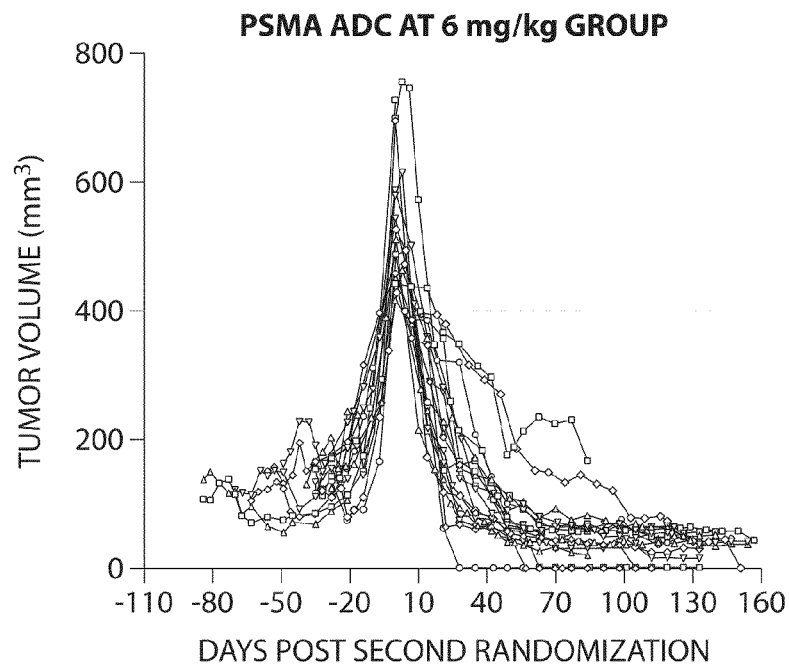
FIG. 15 shows the tumor size for each individual animal in two groups after second randomization. The tumor volumes of animals with PSMA ADC treatment (panel A) and continued docetaxel treatment (panel B) were plotted as a function of time following the second randomization (day 0). The tumors shrank when PSMA ADC treatment was initiated (panel A). However, even with continued docetaxel treatment, tumors continued to progress except in one animal (panel B).
Figure 15B:
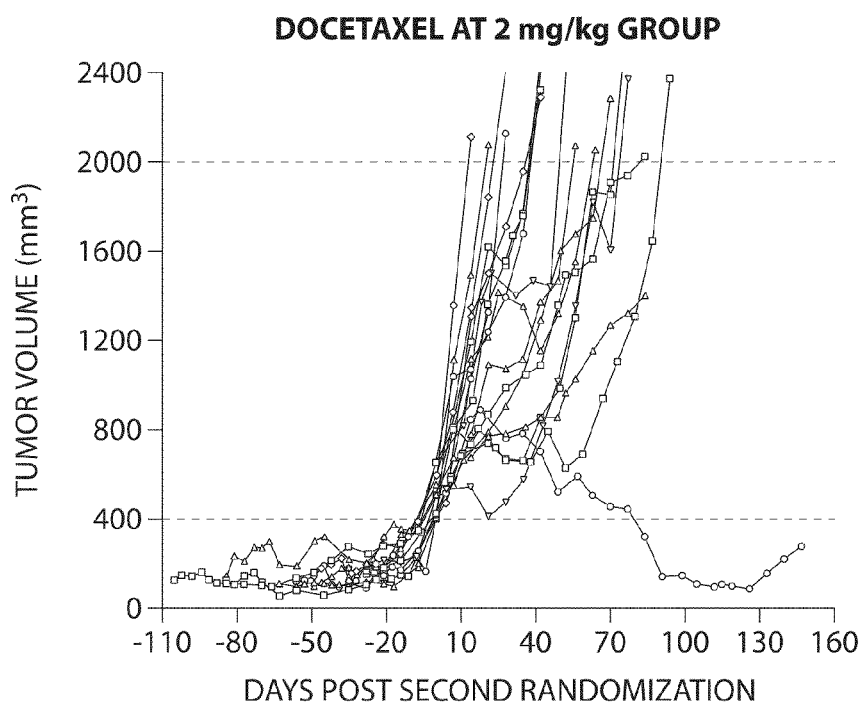
Figure 16:
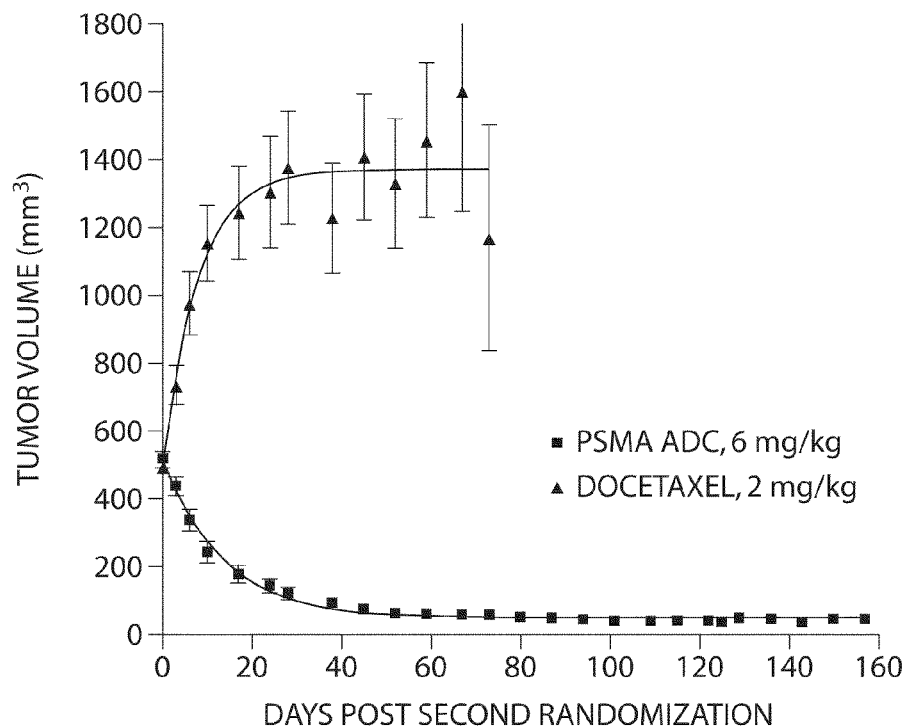
FIG. 16 shows a comparison of the mean tumor volumes in animals receiving PSMA ADC treatment (filled squares) and in animals receiving continued docetaxel treatment (filled triangles). Mean tumor volume was compared as a function of time following the second randomization (day 0). Tumor sizes of the two groups were significantly different (p<0.007).
Figure 17:
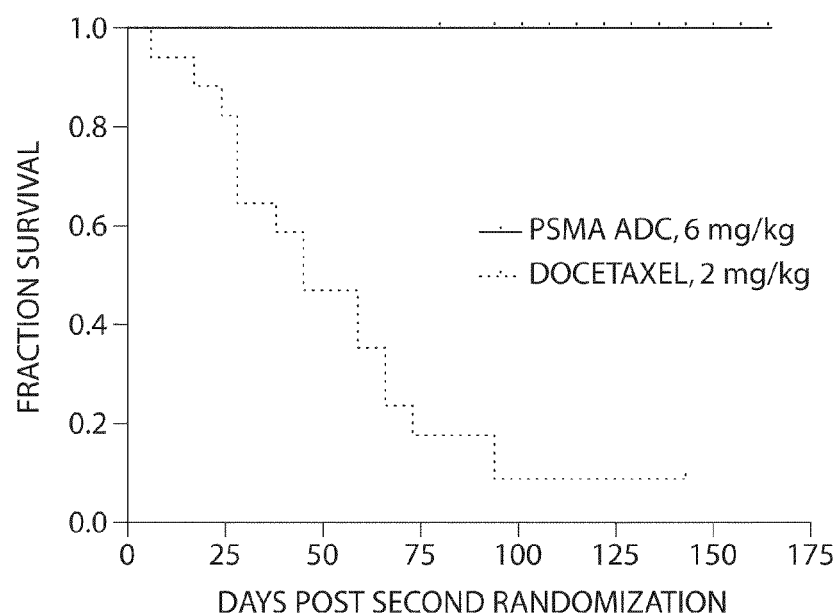
FIG. 17 shows a comparison of the survival of animals over time post second randomization for animals receiving PSMA ADC treatment (solid line) and animals receiving continued docetaxel treatment (dotted line). At day 157 post second randomization, all 18 animals in the PSMA ADC treatment group were still alive. However, 16 of 18 animals in the continued docetaxel treatment group were sacrificed due to their large tumors (>2,000 mm³) with a median survival of 45 days. PSMA ADC significantly increased the overall survival (p<0.0001).
Figure 18:
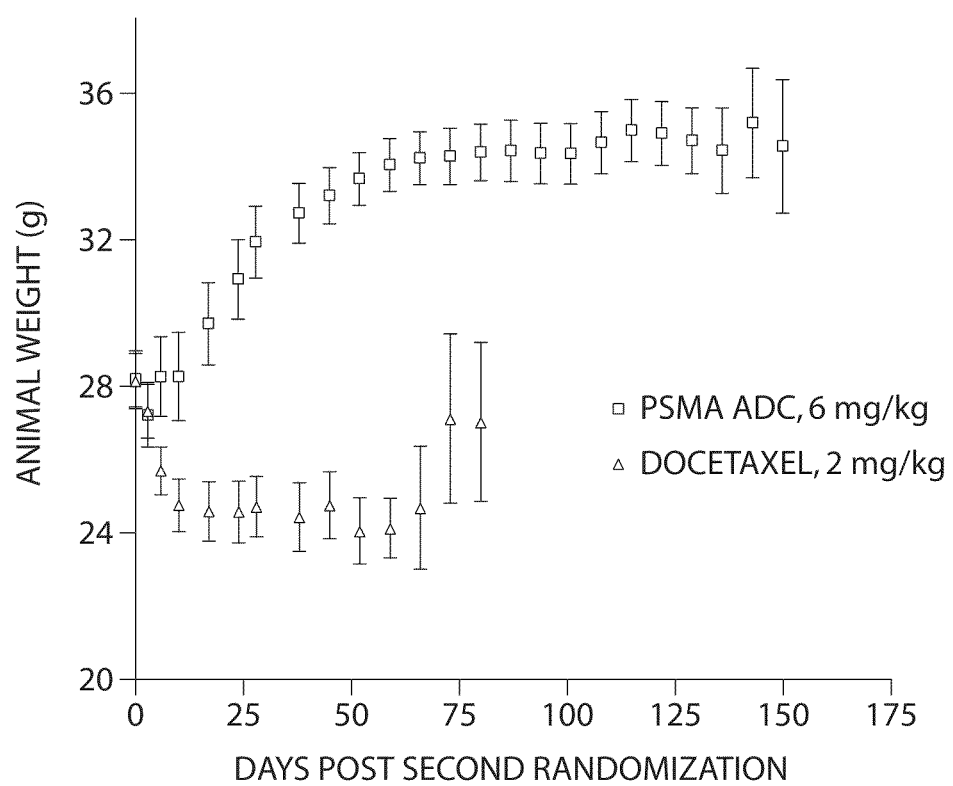
FIG. 18 shows a comparison of the average body weights post second randomization in animals receiving PSMA ADC treatment (solid squares) and animals receiving continued docetaxel treatment (solid triangles). Overall, animals gained weight in the PSMA ADC treatment group, while animals lost weight in the continued docetaxel treatment group. The body weight change was significantly different (p<0.001) between these two groups.

Mean tumor volumes were 515±103 mm$^3$ and 495±80 mm$^3$ for the PSMA ADC and continued docetaxel treatment groups, respectively, at the second randomization (p=0.518) (FIG. 14). At end of the experiment, the survival rate was 100% for animals in the PSMA ADC treatment group (FIG. 17); 94% of these mice had tumor sizes <100 mm$^3$ (FIG. 16). In contrast, the survival rate was 11% in the continued docetaxel treatment group. Therefore, PSMA ADC treatment significantly shrank tumors and increased overall survival of animals compared to continued docetaxel treatment (p<0.0001). PSMA ADC was generally well tolerated in the animal (FIG. 18). PSMA ADC demonstrated potent antitumor activity against large prostate tumors that had progressed following docetaxel treatment. Treatment with PSMA ADC significantly extended survival.

Example 5

A Phase 1 Dose-Escalation Study of PSMA ADC in Subjects with Progressive, Castration-Resistant, Metastatic Prostate Cancer An open-label, dose-escalation phase 1 study of PSMA ADC IV in subjects with progressive, castration-resistant, metastatic prostate cancer that has progressed after prior taxane therapy is initiated. Subjects will receive either 0.4 mg/kg, 0.7 mg/kg, 1.1 mg/kg, 1.8 mg/kg or 2.9 mg/kg by constant-rate 90-minute IV infusion of PSMA ADC in saline (at weeks 0, 3, 6 and 9). Additional subjects who meet the inclusion/exclusion criteria of the study will be entered into the maximum tolerated dose (MTD) cohort until it is filled per the criteria below. The maximum duration of the treatment for each subject will be 12 weeks.

The dose-limiting toxicity (DLT) is defined as any National Cancer Institute (NCI) Common Terminology Criteria for Adverse Events (CTCAE, Version 3.0) toxicity grade ≥3 as well as grade 2 allergic/immunologic toxicity (except isolated fever) for which a causal relationship to the study drug cannot be excluded. In this study, DLT will be determined after the first dose of each cohort. A dose-escalation scheme, based on the DLT, will be employed. Once an MTD is determined or the highest dose cohort is shown safe, additional subjects will be treated. These subjects will be chosen using the same inclusion/exclusion criteria employed for the study. If two or more subjects in the lowest dose cohort experience a DLT, a cohort will be enrolled at 0.2 mg/kg of PSMA ADC.

Radiologic imaging will be obtained at screening and week 12. Blood samples (5 mL) for drug concentrations will be obtained prior to infusion initiation and at 90 minutes and 4, 6, 24, 48, 96, 168, 336 and 504 hours after infusion initiation at weeks 0 and 6. Serum concentrations of study drug (ADC) and total antibody (PSMA–mAb+ADC) will be measured by a fully-validated ELISA method and serum concentrations of free toxin (MMAE) will be measured by a fully-validated liquid chromatography/mass spectrometry/mass spectrometry (LC/MS/MS) method Immunogenicity will be assessed by a fully validated ELISA method for day 1 (predose) and week 12 time points.

All subjects who have completed the 12-week study, and who, in the opinion of the investigator, are likely to benefit from continued treatment with PSMA ADC, will be offered enrollment into an extension study.

Diagnosis and Inclusion Criteria:
1. Males, age ≥18 years (or minimum adult age as determined by local regulatory authorities)
2. Eastern Cooperative Oncology Group (ECOG) status of 0 or 1
3. Histologic confirmation of prostate cancer
4. A diagnosis of progressive, castration-resistant, metastatic prostate cancer based on evidence of metastatic disease on bone scan, CT scan, or MRI at any time following the initial diagnosis of prostate cancer 5. Prior androgen-deprivation therapy consisting of either orchiectomy or luteinizing hormone-releasing hormone (LHRH) agonists, with or without an antiandrogen and a castrate level of serum testosterone (<50 ng/mL)
6. Prior therapy with taxane
7. Lab requirements:
   White blood count (WBC)≥3000/mm$^3$
   Absolute neutrophil count (ANC)≥1000/mm$^3$
   Platelets (Plt)≥100,000 mm$^3$
   Hemoglobin (Hgb)≥10 g/dL
   Total bilirubin ≤2.0 mg/dL
   Serum alanine transferase/serum aspartate transaminase (ALT/AST)≤2× the upper limit of normal
   Serum creatinine≤2.0 mg/dL and a calculated glomerular filtration rate (GFR) of >60 mL/min Exclusion Criteria:
1. Nonprostate primary malignant neoplasm except for nonmelanoma skin cancer or low-grade papillary transitional cell carcinoma of the bladder within previous five years
2. Clinically significant cardiac disease (New York Heart Association Class III/IV) or severe debilitating pulmonary disease
3. Radiation therapy or cytotoxic chemotherapy within previous four weeks
4. Active central nervous system (CNS) or epidural metastatic disease
5. An infection requiring antibiotic treatment within seven days prior to screening and/or antibiotic treatment initiated up to the time of the first dose
6. Peripheral neuropathy of grade 2 or higher with any association to taxane therapy at the start of the study
7. Any prior treatment with any other therapy targeting PSMA
8. Subjects must not have participated in any other research study within 30 days
9. Prior therapy with investigational or approved mAbs or Ig fusion proteins
10. Subjects with QTc≥500 msec
11. Weight >225 pounds Example 6

Two-Stage Clinical Study Design

A phase 1, open-label, dose-escalation clinical trial will include men with progressive, hormone-refractory prostate cancer, and who had prior therapy with taxane chemotherapy drugs. The study will investigate the duration of clinical benefit derived from PSMA ADC treatment while also assessing the investigational drug's safety and tolerability. The initial 12-week period will evaluate up to five intravenous doses of PSMA ADC, individually administered at three-week intervals. The study will include evaluations of pharmacodynamics, radiographic changes in tumor burden, and changes in prostate-specific antigen (PSA) and circulating tumor cell (CTC) values compared to baseline.

Following the 12-week period, patients will be offered, at their physician's discretion, the option to continue treatment for an additional 39 weeks with the same dose of PSMA ADC as administered in their initial cohort. Qualified subjects will receive up to 13 additional doses of PSMA ADC at three-week intervals.

Example 7

A Phase 1 Dose-Escalation Study of PSMA ADC in Subjects with Progressive, Castration-Resistant, Metastatic Prostate Cancer An open-label, dose-escalation phase 1 study of PSMA ADC IV in subjects with progressive, castration-resistant, metastatic prostate cancer that has progressed after prior taxane therapy was initiated. Subjects received either 0.4 mg/kg, 0.7 mg/kg, 1.1 mg/kg or 1.8 mg/kg or will receive either 2.4 mg/kg, 3.0 mg/kg, 3.5 mg/kg or 4.0 mg/kg by constant-rate IV infusion of PSMA ADC in saline administered over approximately 90 minutes (at weeks 0, 3, 6 and 9). Additional subjects who meet the inclusion/exclusion criteria of the study will be entered into the maximum tolerated dose (MTD) cohort until it is filled per the criteria below. The maximum duration of the treatment for each subject was/will be 12 weeks.

The dose-limiting toxicity (DLT) can be defined as any National Cancer Institute (NCI) Common Terminology Criteria for Adverse Events (CTCAE, Version 3.0) toxicity grade ≥3 with the following exception: an absolute neutrophil count (ANC)<500 mm$^3$ determined eight days following the first infusion of PSMA ADC. Under this circumstance, a DLT can be defined as a neutrophil count <500 mm$^3$ found on both study days 8 and 15 following the first infusion of PSMA ADC. A DLT can also be defined as grade ≥2 allergic/immunologic toxicity (except isolated fever) for which a causal relationship to the study drug cannot be excluded. In this study, DLT was/will be determined after the first dose of each cohort. A dose-escalation scheme, based on the DLT, was/will be employed. Once an MTD is determined or the highest dose cohort is shown safe, additional subjects will be treated. These subjects will be chosen using the same inclusion/exclusion criteria employed for the study. If two or more subjects in the lowest dose cohort experience a DLT, a cohort will be enrolled at 0.2 mg/kg of PSMA ADC.

Radiologic imaging was/will be obtained prior to infusion and within seven days prior to the week 12 visit. Blood samples (5 mL) for drug concentrations was/will be obtained at designated time points in weeks 0, 3, 6, 9 and 12 (at week 12, sampling is at study day 85±one day). At week 0, samples were/are collected prior to infusion initiation, immediately at the end of infusion, and at four and six hours after the infusion. Samples collected at 24, 48, 96, 168, 336 and 504 hours after infusion initiation may be collected within ±two hours of the designated time point. At weeks 3, 6 and 9 only predose samples were/are collected. Serum concentrations of study drug (ADC) and total antibody (PSMA–mAb+ADC) were/will be measured by a fully-validated ELISA method and serum concentrations of free toxin (MMAE) were/will be measured by a fully-validated liquid chromatography/mass spectrometry/mass spectrometry (LC/MS/MS) method. Immunogenicity was/will be assessed by a fully validated ELISA method for day 1 (predose) and week 12 time points.

All subjects who have completed the 12-week study, and who, in the opinion of the investigator, are likely to benefit from continued treatment with PSMA ADC, will be offered enrollment into an extension study.

Diagnosis and Inclusion Criteria:
1. Males, age ≥18 years (or minimum adult age as determined by local regulatory authorities)

2. Eastern Cooperative Oncology Group (ECOG) status of 0 or 1
3. Histologic confirmation of prostate cancer
4. A diagnosis of progressive, castration-resistant, metastatic prostate cancer based on evidence of metastatic disease on bone scan, CT scan, or MRI at any time following the initial diagnosis of prostate cancer
5. Prior androgen-deprivation therapy consisting of either orchiectomy or luteinizing hormone-releasing hormone (LHRH) agonists, with or without an antiandrogen and a castrate level of serum testosterone (<50 ng/dL)
6. Prior therapy with taxane
7. Lab requirements:
    White blood count (WBC)≥3000/mm$^3$
    Absolute neutrophil count (ANC)≥1000/mm$^3$
    Platelets (Plt)≥100,000 mm$^3$
    Hemoglobin (Hgb)≥9.0 g/dL
    Total bilirubin ≤2.0 mg/dL
    Serum alanine transferase/serum aspartate transaminase (ALT/AST)≤2× the upper limit of normal (ULN)
    Serum creatinine≤2.0 mg/dL and a calculated glomerular filtration rate (GFR) of >60 mL/min Exclusion Criteria:
1. Nonprostate primary malignant neoplasm except for nonmelanoma skin cancer or low-grade papillary transitional cell carcinoma of the bladder within previous five years
2. Clinically significant cardiac disease (New York Heart Association Class III/IV) or severe debilitating pulmonary disease
3. Radiation therapy or cytotoxic chemotherapy within previous six weeks
4. Active central nervous system (CNS) or epidural metastatic disease
5. Evidence of an active infection requiring ongoing antibiotic therapy
6. Peripheral neuropathy of grade 2 or higher with any association to taxane therapy at the start of the study
7. Any prior treatment with any other therapy targeting PSMA
8. Subjects must not have participated in any other research study within 30 days
9. Prior therapy with investigational or approved mAbs or Ig fusion proteins
10. Subjects with QTc≥500 msec
11. History of pancreatitis or surgical procedures to the pancreas
12. History of drug and/or alcohol abuse
13. Any medical condition that in the opinion of the investigator may interfere with a subject's participation in or compliance with the study Example 8

Two-Stage Clinical Study Design

A phase 1, open-label, dose-escalation clinical trial included men with progressive, hormone-refractory prostate cancer, and who had prior therapy with taxane chemotherapy drugs. The study investigates the duration of clinical benefit derived from PSMA ADC treatment and assesses the investigational drug's safety and tolerability. PSMA ADC was individually administered at three-week intervals during a 12-week period for the evaluation of at least four intravenous doses of PSMA ADC. The study includes evaluations of pharmacodynamics, radiographic changes in tumor burden, and changes in prostate-specific antigen (PSA) and circulating tumor cell (CTC) values compared to baseline.

Following the 12-week period, patients will be offered, at their physician's discretion, the option to continue treatment for an additional 39 weeks with the same dose of PSMA ADC as administered in their initial cohort. Qualified subjects will receive up to 13 additional doses of PSMA ADC at three-week intervals.

Example 9

Dosage Regimen and Mode of Administration of PSMA ADC

An open-label, dose-escalation phase 1 study of PSMA ADC administered IV in subjects with progressive, castration-resistant, metastatic prostate cancer that has progressed after prior taxane therapy is initiated. Intravenous (IV) infusions of PSMA ADC will be administered to subjects in four cycles. In cohorts 1-8, IV infusions of PSMA ADC will be administered once at the start of a cycle (duration 3 weeks or Q3W; weeks 1, 4, 7 and 10) for a total of 4 doses (4 cycles) as eight progressively enrolled treatment groups: 0.4 mg/kg, 0.7 mg/kg, 1.1 mg/kg, 1.8 mg/kg, 2.4 mg/kg, 3.0 mg/kg, 3.5 mg/kg or 4.0 mg/kg. In cohorts 9-12, IV infusions of PSMA ADC will be administered to subjects once every week for the first three weeks of a four week cycle for a total of 12 doses (4 cycles or 4QW with a dose during week 1, 2 and 3 in cycle 1; weeks, 5, 6 and 7 in cycle 2; weeks 9, 10 and 11 in cycle 3; and weeks 13, 14 and 15 in cycle 4; no doses will be administered during weeks 4, 8, 12 and 16 in cycles 1, 2, 3 and 4, respectively) as four progressively enrolled treatment groups: 0.6 mg/kg, 0.9 mg/kg, 1.2 mg/kg and 1.5 mg/kg. For all treatments, PSMA ADC will be administered in saline over approximately 90 minutes. Additional subjects who meet the inclusion/exclusion criteria of the study will be entered into the MTD for each dosing regimen until it is filled as per the criteria below. The maximum duration of the treatment for subjects in cohorts 1-8 will be 13 weeks and for subjects in cohorts 9-12, 17 weeks.

The dose-limiting toxicity (DLT) will be defined as any National Cancer Institute (NCI) Common Terminology Criteria for Adverse Events (CTCAE, Version 3.0) toxicity grade ≥3 with the following exception: an absolute neutrophil count (ANC)<500 mm$^3$. For all cohorts, a DLT will be defined as a neutrophil count <500 mm$^3$ that persist upon repeat determination 3 to 7 days following final PSMA ADC administration within the first cycle. For cohorts 9-12 an ANC<500 mm$^3$ prior to any dose in the first cycle is a DLT. A DLT is also defined as grade ≥2 allergic/immunologic toxicity (except isolated fever) for which a causal relationship to the study drug cannot be excluded. In this study, DLT will be determined after the first cycle of each cohort. A dose-escalation scheme, based on the DLT, will be employed. Determinations of DLT will occur as a separate consideration for cohorts 1-8 and 9-12. A DLT determination for cohort 1-8 will not influence enrollment in cohorts 9-12. Once an MTD is determined or the highest dose cohort is shown safe, additional subjects will be treated. These subjects will be chosen using the same inclusion/exclusion criteria employed for the study.

For subjects in cohorts 1-8, radiologic imaging will be obtained prior to infusion and within seven days prior to the week 13 visit. Blood samples (5 mL) for drug concentrations will be obtained at time points in weeks 0, 1, 4, 7, 10 and 13 (at week 13, sampling is at study day 85±one day). At week 1, samples are collected prior to infusion initiation, immediately at the end of infusion, and at four and six hours after the infusion. Samples collected at 24, 48, 96, 168, 336 and 504 hours after infusion initiation may be collected within ±two hours of the designated time point. At weeks 4, 7 and 10 only predose samples are collected. For subjects in cohorts 9-12, radiologic imaging will be obtained prior to the first infusion (week 1) and within seven days prior to the week 17 visit. Blood samples (5 mL) for drug concentrations will be obtained at designated time points: for week 1 (cycle 1) immediately prior to infusion initiation, immediately at the end of the infusion, and at four and at six hours after the infusion. Samples collected at 24, 48 and 96 hours after infusion initiation may be collected within ±two hours of the designated time point. Samples collected at weeks 2, 3 and 5 are collected prior to infusion. Samples are also to be obtained at week 4. Serum concentrations of study drug (ADC) and total antibody (PSMA–mAb+ADC) will be measured by a fully-validated ELISA method and serum concentrations of free toxin (MMAE) will be measured by a fully-validated liquid chromatography/mass spectrometry/mass spectrometry (LC/MS/MS) method. Immunogenicity will be assessed by a fully validated ELISA method for day 1 (predose) and week 13 time points for cohorts 1-8 and study day 1 (predose) and week 17 for cohorts 9-12.

All subjects who have completed the 12-week study, and who, in the opinion of the investigator, are likely to benefit from continued treatment with PSMA ADC, will be offered enrollment into an extension study.

Diagnosis and Inclusion Criteria:
1. Males, age ≥18 years (or minimum adult age as determined by local regulatory authorities)
2. Eastern Cooperative Oncology Group (ECOG) status of 0 or 1
3. Histologic confirmation of prostate cancer
4. A diagnosis of progressive, castration-resistant, metastatic prostate cancer based on evidence of metastatic disease on bone scan, CT scan, or MRI at any time following the initial diagnosis of prostate cancer
5. Prior androgen-deprivation therapy consisting of either orchiectomy or luteinizing hormone-releasing hormone (LHRH) agonists, with or without an antiandrogen and a castrate level of serum testosterone (<50 ng/dL)
6. Prior therapy with taxane
7. Lab requirements:
    White blood count (WBC)≥3000/mm$^3$
    Absolute neutrophil count (ANC)≥1000/mm$^3$
    Platelets (Plt)≥100,000 mm$^3$
    Hemoglobin (Hgb)≥9.0 g/dL
    Total bilirubin ≤2.0 mg/dL
    Serum alanine transferase/serum aspartate transaminase (ALT/AST)≤2× the upper limit of normal (ULN)
    Serum creatinine≤2.0 mg/dL and a calculated glomerular filtration rate (GFR) of >60 mL/min Exclusion Criteria:
1. Nonprostate primary malignant neoplasm except for nonmelanoma skin cancer or low-grade papillary transitional cell carcinoma of the bladder within previous five years
2. Clinically significant cardiac disease (New York Heart Association Class III/IV) or severe debilitating pulmonary disease
3. Radiation therapy or cytotoxic chemotherapy within previous six weeks
4. Active central nervous system (CNS) or epidural metastatic disease
5. Evidence of an active infection requiring ongoing antibiotic therapy
6. Peripheral neuropathy of grade 2 or higher with any association to taxane therapy at the start of the study
7. Any prior treatment with any other therapy targeting PSMA
8. Subjects must not have participated in any other research study within 30 days
9. Prior therapy with investigational or approved mAbs or Ig fusion proteins
10. Subjects with QTc≥500 msec
11. History of pancreatitis or surgical procedures to the pancreas
12. History of drug and/or alcohol abuse
13. Any medical condition that in the opinion of the investigator may interfere with a subject's participation in or compliance with the study.

Example 10

Phase 1 Dose-Escalation Study of PSMA ADC in Patients with Taxane Refractory Metastatic Prostate Cancer An open-label, dose-escalation phase 1 study of PSMA ADC (comprising MMAE) in patients with taxane refractory metastatic prostate cancer (metCRPC) was initiated. The objectives of the study were to (1) determine a maximum tolerated dose (MTD) for PSMA ADC administered once every 3 weeks; (2) assess the safety, tolerability, pharmacokinetics (PK) and pharmacodynamics (PD) of PSMA ADC across the dose-escalation range; (3) assess immunogenicity; and (4) assess antitumor activity. PSMA ADC in saline was administered by IV infusion Q3W for up to 4 cycles. Subjects received either 0.4 mg/kg, 0.7 mg/kg, 1.1 mg/kg, or 1.8 mg/kg or will receive 2.0 mg/kg (at weeks 1, 4, 7 and 10).

Figure 19:
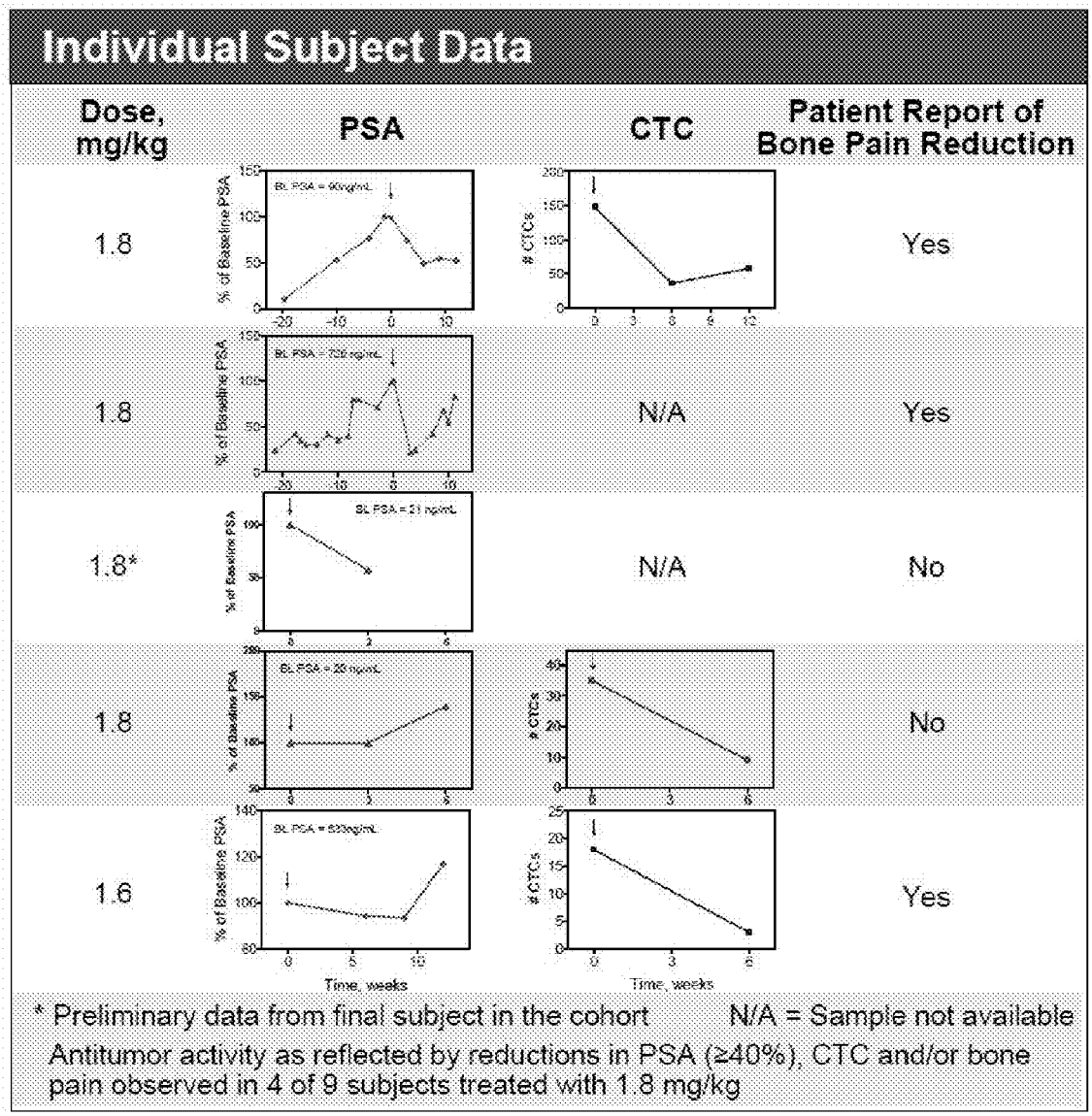
FIG. 19 illustrates antitumor activity in 4 of 9 subjects as reflected by reductions in PSA, CTC and/or bone pain.
Figure 20:
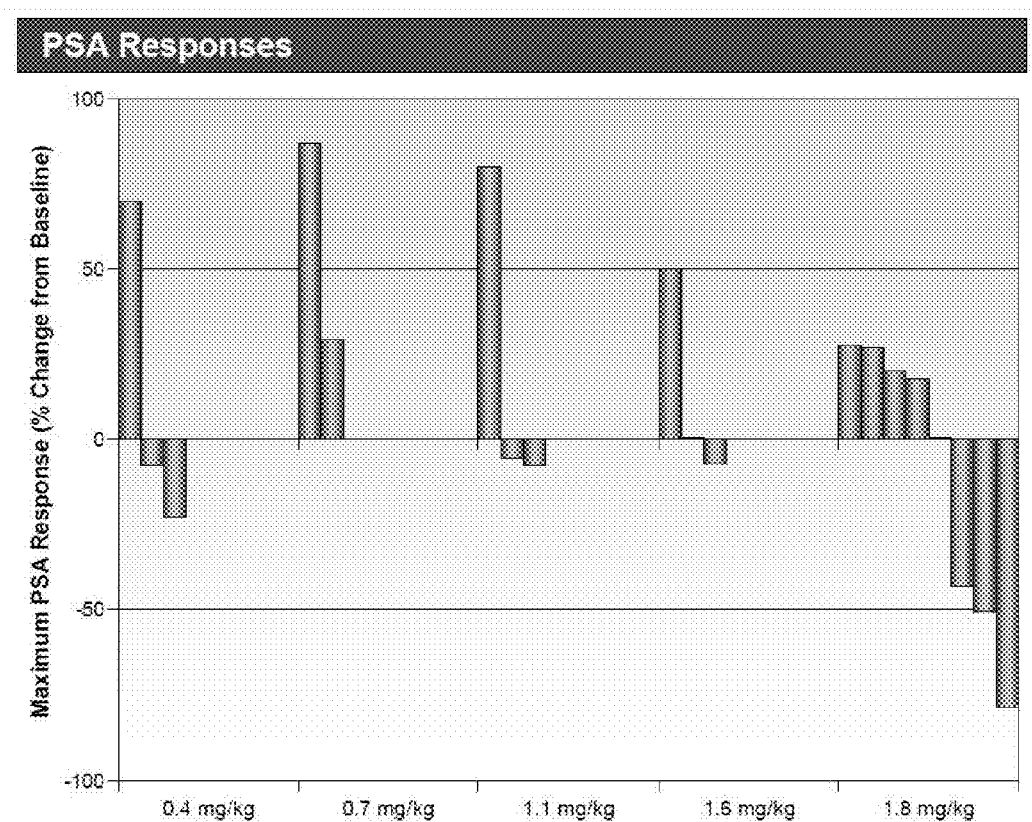
FIG. 20 illustrates the maximum PSA response by dose.
Figure 21:
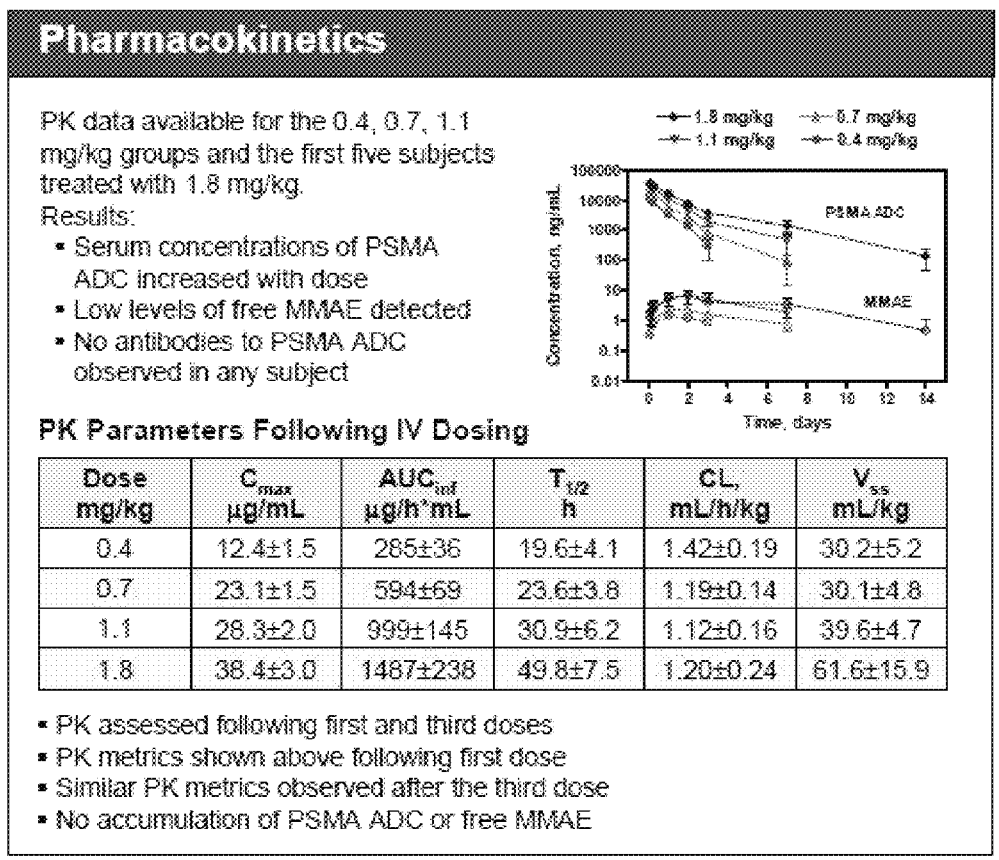
FIG. 21 provides pharmacokinetic data following IV dosing.

Adverse events, PK, PSA, circulating tumor cells, clinical disease progression and immunogenic response to PSMA ADC continued to be assessed (FIGS. 19-21). Serum concentrations of PSMA ADC and total antibody were measured by an enzyme-linked immunosorbent assay (ELISA) method, and free MMAE was measured by liquid chromatography/mass spectrometry/mass spectrometry (LC/MS/MS) method. Individual patients report bone pain reduction as described below.

The demographics of 15 subjects enrolled in the four dosing cohorts (0.4, 0.7, 1.1 and 1.8 mg/kg) were similar. Treatment has been generally well tolerated and the most common laboratory abnormalities were reversible changes in liver and hematological parameters. Exposure to PSMA ADC and serum half life (t½) increased in a dose-proportional manner Similar PK metrics were observed after the first and third doses. Exposure to free MMAE was also dose proportional and approximately <0.1% of PSMA ADC.

PSMA ADC has been generally well-tolerated at doses ≤1.8 mg/kg, and antitumor activity was observed at 1.8 mg/kg. PSMA ADC appears to exhibit dose-proportional PK and limited release of free MMAE.

Diagnosis and Inclusion Criteria:
1. Males, age ≥18 years (or minimum adult age as determined by local regulatory authorities)
2. Eastern Cooperative Oncology Group (ECOG) status of 0 or 1
3. Histological, pathological and/or cytological confirmation of prostate cancer
4. Diagnosis of progressive, castration-resistant, metastatic prostate cancer based on evidence of metastatic disease
5. Prior and/or ongoing androgen-deprivation therapy and a castrate level of serum testosterone (<50 ng/dL)

6. Prior chemotherapy regimens at least one of which contains taxane
7. Adequate organ function
Exclusion Criteria:
1. Radiation therapy or cytotoxic therapy within previous 6 weeks
Study Endpoints:
Safety and Tolerability of PSMA ADC
Hematology, blood chemistry, and urine values; periodic measurements of vital signs and electrocardiograms (ECGs); and the findings of physical examinations
Pharmacokinetic Assessments
Concentrations of PSMA ADC and its components
Antibodies to PSMA ADC
Assessments for Antitumor Activity
Changes in serum prostate-specific antigen (PSA)
Changes in the number of circulating tumor cells (CTC) from baseline
Change from baseline in radiographic imaging of metastasis (bone scan, computed tomography (CT) scan, magnetic resonance imaging (MRI))
Assessment of Pain
A modification of the Brief Pain Inventory (BPI) assessment developed by MD Anderson Cancer Center was administered (shown below) at baseline, prior to the second dose (week four), and at week 13/End of Study Visit. All subjects who received at least one dose of PSMA ADC was included in the analyses.
Modified Brief Pain Inventory (BPI) Assessment:
1. Please rate your pain by circling the one number that best describes your pain at its worst in the last 24 hours:
0 1 2 3 4 5 6 7 8 9 10 (0 for No Pain, 10 for Pain as bad as you can imagine)
2. Please rate your pain by circling the one number that best describes your pain at its least in the last 24 hours.
0 1 2 3 4 5 6 7 8 9 10 (0 for No Pain, 10 for Pain as bad as you can imagine)
3. Please rate your pain by circling the one number that best describes your pain on the average.
0 1 2 3 4 5 6 7 8 9 10 (0 for No Pain, 10 for Pain as bad as you can imagine)
4. Please rate your pain by circling the one number that tells how much pain you have right now.
0 1 2 3 4 5 6 7 8 9 10 (0 for No Pain, 10 for Pain as bad as you can imagine)

TABLE 3

| Dose, mg/kg | 0.4 | 0.7 | 1.1 | 1.6 | 1.8 | 2.0 |
| --- | --- | --- | --- | --- | --- | --- |
| Number of subjects in main study | 3 | 3 | 3 | 3 | 9 | Enrolling |
| Number of subjects entered into extension study | 1 | 1 | 0 | 1 | 2 | |

Each of the foregoing patents, patent applications and references that are recited in this application are herein incorporated in their entirety by reference. However, such recitation is not intended to be an admission that any of the foregoing patents, patent applications and references is a prior art reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method of treating a subject having progressive, castration-resistant, metastatic prostate cancer that has progressed after prior taxane therapy, the method comprising:
   selecting a subject having progressive, castration-resistant, metastatic prostate cancer that has progressed after prior taxane therapy, and
   administering an effective amount of a prostate-specific membrane antigen antibody drug conjugate (PSMA ADC) to the subject, wherein the PSMA ADC comprises a human monoclonal antibody to PSMA conjugated to monomethylauristatin norephedrine (MMAE) or monomethylauristatin phenylalanine (MMAF), and wherein the effective amount is sufficient to 1) delay or inhibit progression of the cancer, 2) increase survival of the subject as compared to the median survival of subjects who have not been treated with the PSMA ADC and who have progressive, castration-resistant, metastatic prostate cancer that has progressed after prior taxane therapy, 3) decrease a circulating level of circulating tumor cells (CTCs) compared to a baseline level, or 4) decrease or stabilize a serum level of PSA compared to a baseline level of PSA.

2. The method of claim 1, wherein the effective amount is sufficient to delay or inhibit progression of the cancer.

3. The method of claim 1, wherein the effective amount is sufficient to increase survival of the subject as compared to the median survival of subjects who have not been treated with the PSMA ADC and who have progressive, castration-resistant, metastatic prostate cancer that has progressed after prior taxane therapy.

4. The method of claim 1, wherein the effective amount is sufficient to decrease the circulating level of CTCs as compared to the baseline level.

5. The method of claim 1, wherein the effective amount is sufficient to decrease or stabilize the serum level of PSA compared to the baseline level of PSA.

6. The method of claim 1, wherein the human antibody to PSMA is conjugated to MMAE or MMAF via a valine-citrulline linker.

7. The method of claim 1, wherein the taxane is docetaxel.

8. The method of claim 1, wherein the taxane is paclitaxel.

9. The method of claim 1, wherein the human antibody is an IgG1 comprising (a) a heavy chain encoded by a nucleic acid molecule comprising the coding region or regions of a nucleotide sequence set forth as SEQ ID NO: 2, and (b) a light chain encoded by a nucleic acid molecule comprising the coding region or regions of a nucleotide sequence set forth as SEQ ID NO: 8.

10. The method of claim 1, wherein the delay or inhibition of progression of the cancer is demonstrated by radiographic image changes in tumor burden compared to a baseline radiographic image in the subject prior to the administration of the PSMA ADC.

11. The method of claim 10, wherein the radiographic image change is a change of at least 10%.

12. The method of claim 11, wherein the radiographic image change is a change of at least 20%.

13. The method of claim 12, wherein the radiographic image change is a change of at least 30%.

14. The method of claim 13, wherein the radiographic image change is a change of at least 40%.

15. The method of claim 14, wherein the radiographic image change is a change of at least 50%.

16. The method of claim 15, wherein the radiographic image change is a change of at least 60%.

17. The method of claim 1, wherein the effective amount of the PSMA ADC is a dose of 0.1 mg/kg to 5 mg/kg.

18. The method of claim 17, wherein the effective amount of the PSMA ADC is a dose of 0.2 mg/kg, 0.4 mg/kg, 0.5 mg/kg, 0.6 mg/kg, 0.7 mg/kg, 0.9 mg/kg, 1 mg/kg, 1.1 mg/kg, 1.2 mg/kg, 1.5 mg/kg, 1.6 mg/kg, 1.8 mg/kg, 2 mg/kg, 2.4 mg/kg or 2.9 mg/kg.

19. The method of claim 17, wherein the subject is administered a total of 4 doses.

20. The method of claim 17, wherein the subject is administered a total of 12 doses.

21. The method of claim 17, wherein the subject is administered a total of 17 doses.

22. The method of claim 17, wherein the subject is administered a total of 18 doses.

23. The method of claim 17, wherein the dose is administered at 1, 2, 3 or 4 week intervals.

24. The method of claim 23, wherein the dose is administered at 3 week intervals.

25. The method of claim 17, wherein the subject is administered the dose of PSMA ADC once every week for the first three weeks of a four week cycle for a total of 4 cycles.

26. The method of claim 17, wherein the subject is administered 4 doses at 3-week intervals.

27. The method of claim 17, wherein the subject is administered 5 doses at 3-week intervals.

28. The method of claim 26, wherein the subject is administered an additional 13 doses at 3-week intervals.

29. The method of claim 27, wherein the subject is administered an additional 13 doses at 3-week intervals.

30. The method of claim 17, wherein the subject is administered the PSMA ADC with a dose regimen of q4d×3.

31. The method of claim 17, wherein the subject is administered the PSMA ADC with a dose regimen of q4d×6.

32. The method of claim 17, wherein the dose is administered intravenously.

* * * * *